United States Patent
Bazinet et al.

(10) Patent No.: US 9,492,506 B2
(45) Date of Patent: *Nov. 15, 2016

(54) OLIGONUCLEOTIDE CHELATE COMPLEX—POLYPEPTIDE COMPOSITIONS AND METHODS

(71) Applicant: Replicor Inc., Montreal (CA)

(72) Inventors: Michel Bazinet, Montreal (CA); Andrew Vaillant, Roxboro (CA)

(73) Assignee: REPLICOR INC., Montreal (CA)

( * ) Notice: Subject to any disclaimer, the term of this patent is extended or adjusted under 35 U.S.C. 154(b) by 324 days.

This patent is subject to a terminal disclaimer.

(21) Appl. No.: 13/896,510

(22) Filed: May 17, 2013

(65) Prior Publication Data

US 2013/0309201 A1    Nov. 21, 2013

Related U.S. Application Data

(60) Provisional application No. 61/695,035, filed on Aug. 30, 2012, provisional application No. 61/648,711, filed on May 18, 2012.

(51) Int. Cl.
| | | |
|---|---|---|
| *A61K 31/7088* | (2006.01) | |
| *A61K 38/22* | (2006.01) | |
| *A61K 38/21* | (2006.01) | |
| *A61K 9/00* | (2006.01) | |

(52) U.S. Cl.
CPC ......... *A61K 38/2292* (2013.01); *A61K 9/0019* (2013.01); *A61K 31/7088* (2013.01); *A61K 38/21* (2013.01); *A61K 38/212* (2013.01); *A61K 38/215* (2013.01); *A61K 38/217* (2013.01)

(58) Field of Classification Search
CPC ................................................ A61K 31/7088
See application file for complete search history.

(56) References Cited

U.S. PATENT DOCUMENTS

| | | | | |
|---|---|---|---|---|
| 7,358,068 B2* | 4/2008 | Vaillant | ............. | A61K 31/7088 435/6.16 |
| 8,513,211 B2* | 8/2013 | Vaillant | ............. | A61K 31/7088 424/1.53 |
| 2010/0015090 A1* | 1/2010 | Tung | ................... | A61K 31/496 424/85.4 |

FOREIGN PATENT DOCUMENTS

| WO | 03037272 | 5/2003 |
|---|---|---|
| WO | 2004076474 | 9/2004 |
| WO | 2006042418 | 4/2006 |
| WO | 2007022642 | 3/2007 |
| WO | 2007036016 | 4/2007 |
| WO | WO 2009065181 A1 * | 5/2009 |
| WO | 2009076679 | 6/2009 |
| WO | 2009109665 | 9/2009 |
| WO | 2012021985 | 2/2012 |
| WO | 2014/032176 | 3/2014 |

OTHER PUBLICATIONS

Muir, A.J. et al. Phase 1b study of pegyland interferon lambda 1 with or without ribavirin in patients with chronic genotype 1 hepatitis C virus infection. Hepatology issue of Sep. 2010, vol. 52, No. 3, pp. 822-832, ISSN 1527-3350.
You et al, "Efficacy of thymosin alpha-1 and interferon alpha in treatment of chronic viral hepatitis B: A randomized controlled study", 2006 12, 41, 6715-6721.
M. Al-Mahtab et al. "REP9AC is a potent HBSAG release inhibitor which clears serum HBSG and elicits SVRS in patients with chronic Hepatitis B" Journal of Hepatology, vol. 54, 75, Mar. 1, 2011.

* cited by examiner

*Primary Examiner* — Jon E Angell
(74) *Attorney, Agent, or Firm* — Norton Rose Fulbright Canada LLP

(57) ABSTRACT

It is disclosed a pharmaceutical composition containing an oligonuclelotide chelate complex and at least one polypeptide or pegylated polypeptide. The present disclosure also describes additional pharmaceutical compositions and methods for the treatment of diseases including viral infections.

46 Claims, 46 Drawing Sheets

SEQUENCE LISTING

<160> NUMBER OF SEQ ID NOS: 18

<210> SEQ ID NO 1
<211> LENGTH: 40
<212> TYPE: DNA
<213> ORGANISM: Artificial Sequence
<220> FEATURE:
<223> OTHER INFORMATION: REP 2031, fully phosphorothioated

<400> SEQUENCE: 1 cccccccc cccccccc cccccccc cccccccc                40

<210> SEQ ID NO 2
<211> LENGTH: 40

```
<212> TYPE: DNA
<213> ORGANISM: Artificial Sequence
<220> FEATURE:
<223> OTHER INFORMATION: REP 2055, fully phosphorothioated

<400> SEQUENCE: 2
acacacacac acacacacac acacacacac acacacacac                              40

<210> SEQ ID NO 3
<211> LENGTH: 40
<212> TYPE: DNA
<213> ORGANISM: Artificial Sequence
<220> FEATURE:
<223> OTHER INFORMATION: REP 2057, fully phosphorothioated

<400> SEQUENCE: 3
agagagagag agagagagag agagagagag agagagagag                              40

<210> SEQ ID NO 4
<211> LENGTH: 40
<212> TYPE: RNA
<213> ORGANISM: Artificial Sequence
<220> FEATURE:
<223> OTHER INFORMATION: full phosphorothioated, full 2' O methylribose,
      each cytosine 5' methylated

<400> SEQUENCE: 4
cacacacaca cacacacaca cacacacaca cacacacaca                              40

<210> SEQ ID NO 5
<211> LENGTH: 40
<212> TYPE: DNA
<213> ORGANISM: Artificial Sequence
<220> FEATURE:
<223> OTHER INFORMATION: REP 2056, full phosphorothioated

<400> SEQUENCE: 5
tctctctctc tctctctctc tctctctctc tctctctctc                              40

<210> SEQ ID NO 6
<211> LENGTH: 40
<212> TYPE: DNA
<213> ORGANISM: Artificial Sequence
<220> FEATURE:
<223> OTHER INFORMATION: REP 2133, full phosphorothioated

<400> SEQUENCE: 6
tgtgtgtgtg tgtgtgtgtg tgtgtgtgtg tgtgtgtgtg                              40

<210> SEQ ID NO 7
<211> LENGTH: 16
<212> TYPE: DNA
<213> ORGANISM: Artificial Sequence
<220> FEATURE:
<223> OTHER INFORMATION: miRNA, LNA/DNA, full phosphorothioated
<220> FEATURE:
<221> NAME/KEY: misc_feature
<222> LOCATION: 3, 6,  9, 12, 15
<223> OTHER INFORMATION: LNA
<220> FEATURE:
<221> NAME/KEY: modified_base
<222> LOCATION: 12, 15
<223> OTHER INFORMATION: m5c

<400> SEQUENCE: 7
ccattgtcac actcca                                                        16
```

```
<210> SEQ ID NO 8
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: 21, 22
<223> OTHER INFORMATION: deoxythymidine
<220> FEATURE:
<221> NAME/KEY: misc_feature
<222> LOCATION: 1-18
<223> OTHER INFORMATION: ribonucleotide

<400> SEQUENCE: 8
ggcuccuuag caaagucaag tt                                              22

<210> SEQ ID NO 9
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: 20, 21
<223> OTHER INFORMATION: deoxythymidine
<220> FEATURE:
<221> NAME/KEY: misc_feature
<222> LOCATION: 1-18
<223> OTHER INFORMATION: ribonucleotide

<400> SEQUENCE: 9
cuugacuuug cuaagagcct t                                               21

<210> SEQ ID NO 10
<211> LENGTH: 40
<212> TYPE: DNA
<213> ORGANISM: Artificial Sequence
<220> FEATURE:
<223> OTHER INFORMATION: full phosphorothioate

<400> SEQUENCE: 10
cacacacaca cacacacaca cacacacaca cacacacaca                           40

<210> SEQ ID NO 11
<211> LENGTH: 40
<212> TYPE: DNA
<213> ORGANISM: Artificial Sequence
<220> FEATURE:
<223> OTHER INFORMATION: REP 2148, full phosphorothioate, C = 5'
     methylcytidine

<400> SEQUENCE: 11
acacacacac acacacacac acacacacac acacacacac                           40

<210> SEQ ID NO 12
<211> LENGTH: 40
<212> TYPE: DNA
<213> ORGANISM: Artificial Sequence
<220> FEATURE:
<223> OTHER INFORMATION: full phosphorothioate, C = 5' methylcytidine

<400> SEQUENCE: 12
cacacacaca cacacacaca cacacacaca cacacacaca                           40

<210> SEQ ID NO 13
<211> LENGTH: 40
```

```
<212> TYPE: RNA
<213> ORGANISM: Artificial Sequence
<220> FEATURE:
<223> OTHER INFORMATION: full phosphorothioate, full 2' O methyl ribose

<400> SEQUENCE: 13
acacacacac acacacacac acacacacac acacacacac                      40

<210> SEQ ID NO 14
<211> LENGTH: 40
<212> TYPE: RNA
<213> ORGANISM: Artificial Sequence
<220> FEATURE:
<223> OTHER INFORMATION: full phosphorothioate, full 2' O methyl ribose

<400> SEQUENCE: 14
cacacacaca cacacacaca cacacacaca cacacacaca                      40

<210> SEQ ID NO 15
<211> LENGTH: 40
<212> TYPE: DNA
<213> ORGANISM: Artificial Sequence
<220> FEATURE:
<223> OTHER INFORMATION: full phosphorothioate

<400> SEQUENCE: 15
gagagagaga gagagagaga gagagagaga gagagagaga                      40

<210> SEQ ID NO 16
<211> LENGTH: 40
<212> TYPE: DNA
<213> ORGANISM: Artificial Sequence
<220> FEATURE:
<223> OTHER INFORMATION: full phosphorothioate

<400> SEQUENCE: 16
ctctctctct ctctctctct ctctctctct ctctctctct                      40

<210> SEQ ID NO 17
<211> LENGTH: 40
<212> TYPE: DNA
<213> ORGANISM: Artificial Sequence
<220> FEATURE:
<223> OTHER INFORMATION: full phosphorothioate

<400> SEQUENCE: 17
gtgtgtgtgt gtgtgtgtgt gtgtgtgtgt gtgtgtgtgt                      40

<210> SEQ ID NO 18
<211> LENGTH: 40
<212> TYPE: RNA
<213> ORGANISM: Artificial Sequence
<220> FEATURE:
<223> OTHER INFORMATION: REP 2139, full phosphorothioate, full 2'
     O methyl ribose, C = 5' methylcytidine

<400> SEQUENCE: 18
acacacacac acacacacac acacacacac acacacacac                      40
```

US 9,492,506 B2

OLIGONUCLEOTIDE CHELATE COMPLEX—POLYPEPTIDE COMPOSITIONS AND METHODS

CROSS REFERENCE TO RELATED APPLICATION

This application claims priority from U.S. Provisional Application Ser. No. 61/695,035, filed Aug. 30, 2012, and from U.S. Provisional Application Ser. No. 61/648,711 filed May 18, 2012, the entire content of which are incorporated herein by reference.

TECHNICAL FIELD

The present description relates to compositions comprising an oligonucleotide (ON) chelate complex and one or more different polypeptides or pegylated polypeptides, methods for the preparation of compositions containing an ON chelate complex and one or more different polypeptides or pegylated polypeptides and the methods of treating different diseases with said compositions.

BACKGROUND ART

Oligonucleotide (ON) chelate complexes are two or more ONs linked intermolecularly by a divalent or other multivalent metal cation. ON chelate complexes neutralize the inherent chelation properties of ONs which can contribute to administration-related side effects with these compounds. The administration of ON chelate complexes is a novel method of administering an ON to a subject where administration-related side effects associated with un-chelated ONs are mitigated. These side effects may include shivering, fever and chills with intravenous infusion or induration, inflammation and pain at the injection site with subcutaneous administration. Moreover, by preparing ONs as chelated complexes, their pharmacokinetic behavior may be improved, providing for increased therapeutic performance with similar dosing compared to unchelated ONs. The characterization and properties of ON chelate complexes were previously described in International application publication no. WO 2012/021985 and U.S. application publication no. 2012/0046348, which are incorporated herein by reference in their entirety.

ON chelate complexes provide for an improved method of administering ONs with reduced side effects without affecting the biochemical activity of the ON when administered as a simple sodium salt.

ON chelate complexes comprising an ON which acts by a sequence dependent or sequence independent mechanism can have a therapeutic effect in a disease state which may not provide for an optimal therapeutic result in the diseased subject undergoing treatment with the ON chelate complex.

Accordingly, there is a need in the art to provide for an improved novel composition which comprises an ON chelate complex such as in a combination formulation.

Antiviral ON chelate complexes comprising an antiviral ON which acts by sequence dependent or sequence independent mechanisms can have an antiviral effect against different viral infections. These antiviral effects may not provide for an optimal therapeutic result in the subject with an existing viral infection undergoing treatment with the ON chelate. A further improved therapeutic result may be achieved by the simultaneous use of an antiviral ON chelate complex and a polypeptide-based immunotherapy with known antiviral activity.

Accordingly, there is a need in the art to provide for a novel composition which comprises an antiviral ON chelate complex and an antiviral polypeptide or pegylated polypeptide in combination. Ideally the antiviral polypeptide would also have activity against the viral infection in question, either by affecting the same target/biochemical pathway as the antiviral ON chelate in question or by affecting a target/biochemical pathway distinct from that affected by the antiviral ON chelate complex.

SUMMARY

In accordance with the present description there is now provided a pharmaceutical composition comprising an ON chelate complex and one or more different polypeptides.

In accordance with the present description there is now provided an antiviral pharmaceutical composition comprising an antiviral ON chelate complex and one or more antiviral polypeptides or pegylated polypeptides.

There is disclosed a method of treating a disease state comprising the step of administering a pharmaceutical composition comprising an ON chelate complex and a polypeptide to a subject in need of treatment.

There is disclosed a method of treating a disease state comprising the step of administering by the same or different routes of administration separate pharmaceutical compositions, the first composition comprising the ON chelate complex and the second the polypeptide to a subject in need of treatment.

There is disclosed a method of treating a viral infection comprising the step of administering the pharmaceutical composition comprising an antiviral ON chelate and an antiviral polypeptide to a subject in need of treatment.

There is disclosed a method of treating a viral infection comprising the step of administering by the same or different routes separate pharmaceutical compositions, one comprising the antiviral ON chelate complex and the other the antiviral polypeptide to a subject in need of treatment.

There is disclosed a method of treating a viral infection comprising the step of administering the antiviral ON chelate complex and antiviral polypeptide either in the same pharmaceutical composition or in different pharmaceutical compositions using the same or different routes of administration.

There is disclosed the use of a pharmaceutical composition comprising an ON chelate complex and a polypeptide for treating a disease.

There is disclosed the use of a pharmaceutical composition comprising an ON chelate complex and a polypeptide in the manufacture of a medicament for treating a disease.

There is disclosed the use of a first pharmaceutical composition comprising an ON chelate complex and a second pharmaceutical composition comprising a polypeptide for treating a disease state, the compositions being formulated for the same or different routes of administration.

There is disclosed the use of a pharmaceutical composition comprising an antiviral ON chelate and an antiviral polypeptide for treating a viral infection.

There is disclosed the use of a pharmaceutical composition comprising an antiviral ON chelate and an antiviral polypeptide in the manufacture of a medicament for treating a viral infection.

There is disclosed the use of pharmaceutical compositions, one comprising the antiviral ON chelate complex and the other the antiviral polypeptide, formulated for an administration by the same or different routes separately, for treating a viral infection.

There is disclosed the use of an antiviral ON chelate complex and antiviral polypeptide, formulated either in the same pharmaceutical composition or in different pharmaceutical compositions for the same or different routes of administration, for treating a viral infection.

There is provided pharmaceutical composition comprising an oligonucleotide (ON) chelate complex, consisting of two or more ONs linked intermolecularly by a divalent cation, and at least one polypeptide.

There is provided a pharmaceutical composition comprising an antiviral ON chelate complex, consisting of two or more antiviral ONs linked intermolecularly by a divalent cation, and at least one antiviral polypeptide.

In an embodiment, the antiviral polypeptide is further pegylated.

In another embodiment, the divalent cation is an alkali earth metal with a 2+ charge state.

In another embodiment, the divalent metal cation is a transition metal with a 2+ charge state.

In another embodiment, the divalent metal cation is a lanthanide metal with a 2+ charge state.

In another embodiment, the divalent metal cation is a post-transition metal with a 2+ charge state.

In another embodiment, the divalent metal cation is calcium.

In another embodiment, the divalent metal cation is magnesium.

In another embodiment, the divalent metal cation is iron (2+), manganese, copper or zinc.

In another embodiment, the divalent cation is comprised of two or more different divalent metal cations.

In another embodiment, the divalent cation is comprised of calcium and magnesium.

In another embodiment, the ON chelate complex comprises at least one double stranded ON.

In another embodiment, the ON chelate complex comprises at least one ON with at least one phosphorothioate linkage.

In another embodiment, the ON chelate complex comprises at least one fully phosphorothioated ON.

In another embodiment, the ON chelate complex comprises at least one ON with one 2' modified ribose.

In another embodiment, the ON chelate complex comprises at least one ON which has each ribose 2' O-methylated.

In another embodiment, the ON chelate complex comprises at least one ON comprising at least one 5' methylcytosine.

In another embodiment, the ON chelate complex comprises at least one ON in which each cytosine is further 5' methylcytosine.

In another embodiment, the ON chelate complex comprises an oligonucleotide selected from SEQ ID NOs: 1-6 and 10-18.

In another embodiment, the ON chelate complex comprises an oligonucleotide selected from SEQ ID NOs: 7-9.

In another embodiment, the polypeptide is at least one of:
Thymosin α1;
Any α-interferon or pegylated derivatives thereof;
Any β-interferon or pegylated derivatives thereof;
Any γ-interferon or pegylated derivatives thereof;
Any λ-interferon or pegylated derivatives thereof;
Interferon α-2a or α-2b or α-N3;
Interferon β-1a or β-1b;
Interferon γ-1b;
Interferon λ1 or λ2 or λ3;
Pegylated interferon α-2a or α-2b or λ1 or λ2 or λ3;
Myrcludex B;
Any antiviral cytokine or pegylated derivatives thereof;
Thymic protein A; and
Any polypeptide shown to have antiviral activity or immunostimulatory activity.

In another embodiment, the pharmaceutical composition is formulated for subcutaneous administration.

In another embodiment, the pharmaceutical composition is formulated for intravenous infusion.

In another embodiment, the pharmaceutical composition is formulated for at least one of the following routes of administration: aerosol inhalation, intraocular, oral ingestion, enteric, intramuscular injection, intraperitoneal injection, intrathecal injection, intrathecal infusion, intratracheal, intravenous injection and topically.

In another embodiment, the ON chelate complex comprises at least one ON consisting of SEQ ID NO: 2.

In another embodiment, the ON chelate complex comprises at least one ON consisting of SEQ ID NO: 11.

In another embodiment, the ON chelate complex comprises at least one ON consisting of SEQ ID NO: 18.

In another embodiment, the pharmaceutical composition further comprises one or more of the following: entecavir, tenofovir disoproxil fumarate, telbuvidine, adefovir dipivoxil, lamivudine, ribavirin, telaprevir, boceprevir, GS-7977, tegobuvir, zanamivir, oseltamivir, ganciclovir, foscarnet, acyclovir, zidovudine, abacavir, lopinavir, ritonavir or efavirenz.

In another embodiment, the pharmaceutical composition further comprises a carrier.

There is provided a pharmaceutical composition comprising an ON chelate complex comprising an oligonucleotide consisting of SEQ ID NO: 3, and pegylated interferon α-2a.

There is provided a pharmaceutical composition comprising an ON chelate complex comprising an oligonucleotide consisting of SEQ ID NO: 18, and pegylated interferon α-2a.

There is provided a pharmaceutical composition comprising an ON chelate complex comprising an oligonucleotide consisting of SEQ ID NO: 11, and pegylated interferon α-2a.

There is provided a pharmaceutical composition comprising an ON chelate complex comprising an oligonucleotide consisting of SEQ ID NO: 3, and thymosin α1.

There is provided a pharmaceutical composition comprising an ON chelate complex comprising an oligonucleotide consisting of SEQ ID NO: 18, and thymosin α1.

There is provided a pharmaceutical composition comprising an ON chelate complex comprising an oligonucleotide consisting of SEQ ID NO: 11, and thymosin α1.

There is provided a pharmaceutical composition comprising an ON chelate complex comprising an oligonucleotide consisting of SEQ ID NO: 3, and interferon α-2b.

There is provided a pharmaceutical composition comprising an ON chelate complex comprising an oligonucleotide consisting of SEQ ID NO: 18, and interferon α-2b.

There is provided a pharmaceutical composition comprising an ON chelate complex comprising an oligonucleotide consisting of SEQ ID NO: 11, and interferon α-2b.

There is provided a pharmaceutical composition comprising an ON chelate complex comprising an oligonucleotide consisting of SEQ ID NO: 3, and pegylated thymosin α1.

There is a pharmaceutical composition comprising an ON chelate complex comprising an oligonucleotide consisting of SEQ ID NO: 18, and pegylated thymosin α1.

There is provided a pharmaceutical composition comprising an ON chelate complex comprising an oligonucleotide consisting of SEQ ID NO: 11, and pegylated thymosin α1.

There is provided a pharmaceutical composition comprising an ON chelate complex comprising an oligonucleotide consisting of SEQ ID NO: 3, and pegylated interferon α-2b.

There is a pharmaceutical composition comprising an ON chelate complex comprising an oligonucleotide consisting of SEQ ID NO: 18, and pegylated interferon α-2b.

There is a pharmaceutical composition comprising an ON chelate complex comprising an oligonucleotide consisting of SEQ ID NO: 11, and pegylated interferon α-2b.

There is provided a pharmaceutical composition comprising an ON chelate complex comprising an oligonucleotide consisting of SEQ ID NO: 3, and interferon λ1.

There is a pharmaceutical composition comprising an ON chelate complex comprising an oligonucleotide consisting of SEQ ID NO: 18, and interferon λ1.

There is a pharmaceutical composition comprising an ON chelate complex comprising an oligonucleotide consisting of SEQ ID NO: 11, and interferon λ1.

There is a pharmaceutical composition comprising an ON chelate complex comprising an oligonucleotide consisting of SEQ ID NO: 3, and pegylated interferon λ1.

There is provided a pharmaceutical composition comprising an ON chelate complex comprising an oligonucleotide consisting of SEQ ID NO: 18, and pegylated interferon λ1.

There is provided a pharmaceutical composition comprising an ON chelate complex comprising an oligonucleotide consisting of SEQ ID NO: 11, and pegylated interferon λ1.

There is provided a method for the preparation of the pharmaceutical composition as described herein, the method comprising:
 a. dissolving at least one oligonucleotide (ON) sodium salt in a pharmaceutically acceptable aqueous excipient;
 b. gradually adding a pharmaceutically acceptable divalent metal salt solution to the dissolved ON such that the ON chelate complex remains soluble;
 c. dissolving one or more antiviral polypetides in a compatible, pharmaceutically acceptable aqueous excipient; and
 d. gradually mixing the antiviral polypeptide solution with the ON chelate complex solution such that the solubility of said ON chelate complex and antiviral polypeptide is preserved.

There is also provided a method for the preparation of the pharmaceutical composition as described herein, the method comprising:
 a. dissolving at least one oligonucleotide (ON) sodium salt in a pharmaceutically acceptable aqueous excipient;
 b. gradually adding at least one of a pharmaceutically acceptable calcium and/or magnesium salt solution to the dissolved ON such that the ON chelate complex remains soluble;
 c. dissolving one or more antiviral polypetides in a compatible, pharmaceutically acceptable aqueous excipient; and
 d. gradually mixing the antiviral polypeptide solution with the ON chelate complex solution such that the solubility of said ON chelate complex and antiviral polypeptide is preserved.

In an embodiment, the ON chelate complex solution and the polypeptide solution are combined just prior to the administration of the pharmaceutical composition.

In another embodiment, the ratio of divalent metal salt added to the dissolved ON is 0.1-50 mg per 100 mg of oligonucleotide.

In another embodiment, the final ON concentration is 0.1-200 mg/ml.

In another embodiment, the divalent metal salt is at least one of a chloride salt, a gluconate salt, a citrate salt, a lactate salt, a malate salt, an aspartate salt, a fumarate salt, an ascorbate salt, a benzoate salt, an erythorbate salt, a propionate salt, a sulfate salt or a bicarbonate salt.

In another embodiment, the divalent metal salt solution contains at least one of calcium, magnesium, iron (2+), manganese, copper or zinc.

There is provided a kit comprising the pharmaceutical composition as described herein.

In an embodiment, the ON chelate complex and the at least one polypeptide are formulated separately.

In another embodiment, the ON chelate complex and the at least one polypeptide are formulated for a co-administration by the same or different routes of administration.

BRIEF DESCRIPTION OF THE DRAWINGS

Reference will now be made to the accompanying drawings.

DETAILED DESCRIPTION

Figure 2:
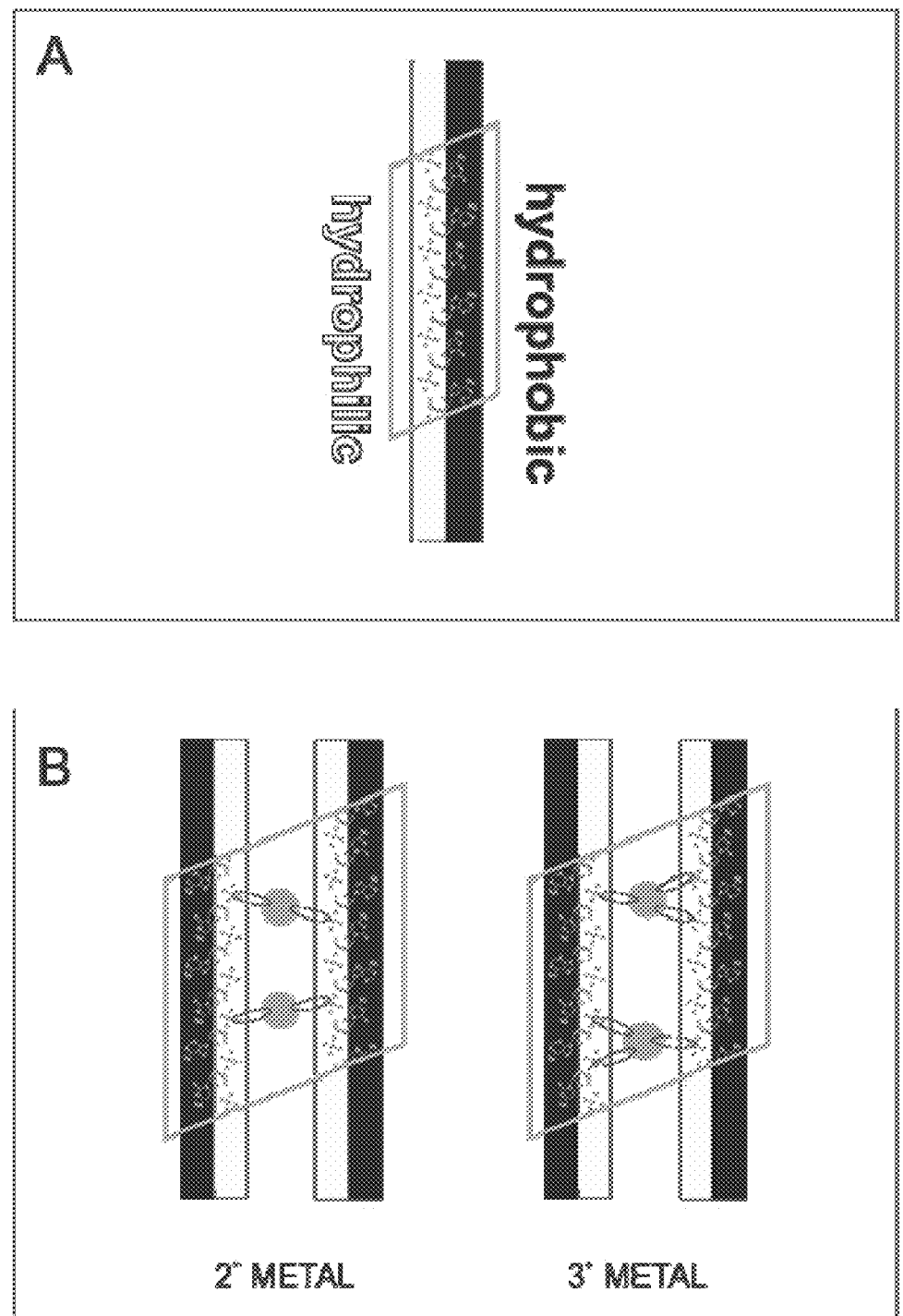
FIG. 2A illustrates the general chemical features of ONs which are not dependent on ON sequence. Regardless of the sequence, any ON exists as a polymer which has both hydrophobic and hydrophilic activities. Phosphorothioation (depicted in the chemical structure in this figure) serves to increase the hydrophobicity of the ON polymer but does not affect the hydrophilicity.
FIG. 2B conceptualizes the nature of ON chelation of divalent and trivalent metal cations. Metal cations (represented by grey solid circles) link the hydrophilic surfaces of ON polymers via metal ion bridges (represented by ellipses) between two or three non-bridging oxygen or sulfur atoms in the phosphodiester linkages.

As described in International application publication no. WO 2012/021995 and U.S. application publication no, 2012/0046348, the content of which is incorporated herein by reference in its entirety, ONs in aqueous solutions containing any simple metal cation that is divalent (such as for example but not limited to, $Ca^{2+}$, $Mg^{2+}$ and $Fe^{2+}$) do not exist as salts but rather as chelated complexes of ONs. These complexes are comprised of ON dimers or higher order molecular organizations in which ONs are linked intermolecularly at their phosphodiester or phosphorothioate backbones via divalent metal ion bridges (see FIG. 2B). At specific ON and metal cation concentrations, these chelated complexes are stable and soluble in aqueous solution and effectively sequester divalent cations in the ON chelate complexes from solution interaction. This chelate complex formation is also likely to occur with simple metal cations with a 3+ charge or greater (as depicted in FIG. 2B). Thus ONs function as multivalent metal cation chelaters and do not form salts with multivalent metal cations.

ON chelate complexes may contain diverse multivalent metal cations including calcium, magnesium, cobalt, iron, manganese, barium, nickel, copper, zinc, cadmium, mercury and lead. It is further demonstrated that chelation of these multivalent metal cations results in the formation of ON chelate complexes comprised of two or more ONs linked via metal cations and occur with ONs greater than 6 nucleotides in length, and in the presence of ONs with either phosphodiester or phosphorothioate linkages. ONs can optionally have each linkage phosphorothioated. Chelation also occurs with ONs containing 2' modifications (such as 2' O methyl) at the ribose or containing modified bases such as 5' methylcytosine or 4-thiouracil. These 2' modifications can be present on one or more or all riboses and modified bases can be present on one or more bases or be universally present on each base (i.e. all cytosines are present as 5' methylcytosine). Additionally, the ON chelate complexes can comprise ONs which contain multiple modifications such as each linkage phosphorothioated, each ribose 2' modified and each base modified. ON modifications compatible with ON chelate complex formation are further defined below. Moreover, the chelation of the metal cations is not dependent on the sequence of nucleotides present but instead relies on the physiochemical features common to all ONs (see FIG. 2A).

While the formation of ON chelate complexes can be achieved with any divalent metal cation, ON chelate complexes intended for use as medications should preferably contain only calcium and/or magnesium but could also contain iron, manganese, copper or zinc in trace amounts and should not include cobalt, barium, nickel, cadmium, mercury, lead or any other divalent metal not listed here.

Importantly, the formation of ON chelate complexes does not occur with monovalent cations such as $Na^+$, $K^+$ or $NH_4^+$ and is thus unlikely to occur with any monovalent cation. Thus, the term "ON salt" is more correctly limited only to ON salts with monovalent cations or with cations which do not form chelate complexes with ONs.

At least a portion of the known transient interaction of ONs with protein components in the blood is likely mediated by the interaction of ONs with calcium binding proteins such as albumin and proteins of the calcium-dependent coagulation cascade. Thus the administration of ONs as chelated complexes (which significantly reduce or eliminate their propensity to interact with calcium-bound proteins) will mitigate these protein interactions in the blood and result in fewer side effects with ON administration (such as transient anti-coagulation) and may also increase the fraction of ON dose reaching the target organs (e.g. the liver, lungs or spleen) compared to unchelated ONs.

Fluorescence polarization is a common methodology used to examine intermolecular interactions. In this technique, the bait (i.e. any ON) is labeled with a fluorescent tag (e.g. FITC). In solution, the bait molecule tumbles freely in solution due to Brownian motion which results in poorly polarized fluorescence emission when the bait is subjected to excitation with the correct wavelength of light. With a ligand of sufficient molecular weight (at least the same size as the bait), the interaction between the bait and the ligand introduces a substantial inhibition of the tumbling of the complex in solution. As a result of this inhibited tumbling in solution, fluorescence emission becomes significantly polarized upon excitation. Thus with this technique, interactions can be measured in solution with no physical constraints on either binding partner. Fluorescence polarization is reported as the dimensionless mP, which is directly proportional to the fraction of bound bait molecules in the reaction. For example, if a very small fraction of bait molecules were bound by a particular ligand, there would be very little fluorescence polarization and consequently small mP values. At the other end of the spectrum, if a large proportion of bait molecules were bound by a particular ligand (or with a higher concentration of ligand), there would be substantial fluorescence polarization and consequently large mP values. In this fashion, binding isotherms for particular bait-ligand interactions can be generated by varying concentrations of ligand in the presence of a fixed amount of fluorescently tagged bait.

Herein diverse fluorescently labeled ONs are employed to examine their complex formation in the presence of multivalent metal cations. Although the monitoring of complex formation by fluorescence polarization requires these ONs to be fluorescently labeled, this label is affixed to the ON at the 3' end so as not to interfere with either the nitrogenous base or the phosphodiester backbone of the ON is question. Moreover the fluorescent tag is held away from the ON by a rigid 3 carbon linker to further exclude any perturbation of normal ON behavior in solution. Thus any ON complex formation observed herein using fluorescence polarization with a fluorescently labeled ON is an accurate representation of the solution behavior of unlabeled ONs (whether complexed or not).

The standard in the art clearly teaches the practice of administration of ONs to subjects in need of treatment with ON sodium salts. This is exemplified by the administration of numerous ONs in clinical trials as sodium salts which include Fomivirisen (ISIS 2922), Mipomersen (ISIS 301012), Trecovirsen (GEM 91), Custirsen (OGX-011/ISIS 112989), Genasense (G3139), Aprinocarsen (ISIS 3531/LY 900003), PRO-51 (GSK 2402968) and ALN-RSV01 (Geary et al., 2002, Clin. Pharmacokinetics, 41: 255-260; Yu et al., 2009, Clin. Pharmacokinetics, 48: 39-50; Sereni et al., 1999, J. Clin. Pharmacol., 39: 47-54; Chi et al., 2005, J. Nat. Canc. Inst., 97: 1287-1296; Marshall et al., 2004, Ann. Oncol., 15: 1274-1283; Grossman et al., 2004, Neuro-Oncol, 6: 32-40; Goemans et al., 2011 NEJM 364: 1513-1522). There is no currently published data teaching the formulation of oligonucleotides for parenteral administration with the use of calcium, magnesium or other divalent metals.

Many of the side effects associated with the administration of sodium salt ONs can be attributable to their chelation effects. The anti-coagulation of blood by ONs is at least in part caused by chelation of serum calcium by ONs thus impairing the calcium dependent coagulation cascade. This chelation of serum calcium and the underlying serum hypocalcemia it can cause is also consistent with the side-effects observed with the administration of ONs by IV administration which includes fever, shivering, weakness and lowering of arterial blood pressure (the latter with rapid IV infusion or injection). Injection site reactions observed with subcutaneous injections of ONs (induration, inflammation, tenderness and pain) is due at least in part to local chelation of calcium and possibly other divalent or multivalent cations such as magnesium at the injection site by ONs. The administration of ONs as chelated complexes has been shown to mitigate many of these side effects.

Moreover, because ON chelate complexes will form with divalent metals in solution with any ON, the teaching of the formation and compatibility of various polypeptides and pegylated polypeptides in solution with any ON chelate complex will be adequately demonstrated to any skilled in the art by the use of the degenerate ON REP 2006 and an exemplary oligonucleotide sequence [in the examples below $(AG)_{20}$ and $(AC)_{20}$] with diverse ON modifications. The stable formation of compositions containing the above ON species as chelates with diverse polypeptides or pegylated polypeptides will demonstrate that any ON chelate complex (regardless of its specific functionality) will form a stable solution with various polypeptides or pegylated polypeptides which would be desirable in the art for the treatment of a specific disease indication (e.g. pegylated interferons for the treatment of hepatitis B or hepatitis C or myrcludex B for the treatment of hepatitis B).

The term oligonucleotide (ON) refers to an oligomer or polymer of ribonucleic acid (RNA) and/or deoxyribonucleic acid (DNA). This term includes ONs composed of modified nucleobases (including 5'methylcytosine and 4'thiouracil), sugars and covalent internucleoside (backbone) linkages as well as ONs having non-naturally-occurring portions which function similarly. Such modified or substituted ONs may be preferable over native forms because of desirable properties such as, for example, reduced immunoreactivity, enhanced cellular uptake, enhanced affinity for nucleic acid target and increased stability in the presence of nucleases. ONs can also be double stranded.

ONs in this disclosure can include various modifications, e.g., stabilizing modifications, and thus can include at least one modification in the phosphodiester linkage and/or on the sugar, and/or on the base. For example, the ON can include, without restriction, one or more modifications, or be fully modified so as to contain all linkages or sugars or bases with the recited modifications, Modified linkages can include phosphorothioate linkages, phosphorodithioate linkages, and/or methylphosphonate linkages. While modified linkages are useful, the ONs can include phosphodiester linkages. Additional useful modifications include, without restriction, modifications at the 2'-position of the sugar including 2'-O-alkyl modifications such as 2'-O-methyl modifications, 2' O-methoxyethyl (2' MOE), 2'-amino modifications, 2'-halo modifications such as 2'-fluoro; acyclic nucleotide analogs. Other 2' modifications are also known in the art and can be used such as locked nucleic acids. In particular, the ON has modified linkages throughout or has every linkage modified, e.g., phosphorothioate; has a 3'- and/or 5'-cap; includes a terminal 3'-5' linkage; the ON is or includes a concatemer consisting of two or more ON sequences joined by a linker(s). Base modifications can include 5'methylation of the cytosine base (5' methylcytosine or in the context of a nucleotide, 5'methylcytidine) and/or 4'thioation of the uracil base (4'thiouracil or in the context of a nucleotide, 4'thiouridine). Different chemically compatible modified linkages can be combined where the synthesis conditions are chemically compatible such as having an oligonucleotide with phosphorothioate linkages, a 2' ribose modification (such as 2'O-methylation) and a modified base (such as 5'methylcytosine). The ON can further be completely modified with all of these different modifications (e.g. each linkage phosphorothioated, each ribose 2' O methyl modified and each cytosine base having additionally the 5' methyl modification (5'methylcytosine)).

In the present description, the term "antiviral ON" refers to any ON which by virtue of its specific biochemical activity (whether sequence dependent or sequence independent) has the ability to directly or indirectly inhibit some aspect of viral replication or to directly or indirectly enhance the host's ability to clear the infections by immunological or other mechanisms.

In the present disclosure, the term "ON chelate complex" refers to a complex of two or more ONs in solution linked intermolecularly by a multivalent metal cation.

In the present disclosure, the term "antiviral ON chelate complex" refers to a complex of two or more antiviral ONs in solution linked intermolecularly by a multivalent metal cation. The antiviral ON chelate complex can be comprised of a single species of antiviral ON or two or more different species of antiviral ON which can have the same or different mechanisms of action (e.g. two or more antisense ONs, at least one antisense ON and at least one aptamer, at least one antisense ON and at least one siRNA).

In the present disclosure, the term "antiviral polypeptide" refers to a polypeptide which by virtue of its specific biochemical activity (whether sequence dependent or sequence independent) has the ability to directly or indirectly inhibit some aspect of viral replication or to directly or indirectly enhance the host's ability to clear the infections by immunological or other mechanisms. The polypeptide can be naturally derived or recombinant. The polypeptide can be recombinantly derived from a portion of the naturally occurring polypeptide. The polypeptide can be pegylated or not pegylated.

In the present disclosure, the term "degenerate ON" is intended to mean a single stranded ON having a wobble (N) at every position, such as NNNNNNNNNN. Each base is synthesized as a wobble such that this ON actually exists as a population of different randomly generated sequences of the same length and physiochemical properties. For example, for an ON degenerate 40 bases in length, any particular sequence in the population would theoretically represent only $1/4^{40}$ or $8.3 \times 10^{-25}$ of the total fraction. Given that 1 mole=$6.022 \times 10^{23}$ molecules, and the fact that 1 mole of a 40mer ON would mass approximately 12-14 kg (depending on sequence and modifications present), any ON with a specific sequence effectively does not exist more than once in any preparation. Thus any chelate formation or biological activity observed in such a preparation must be due to the non-sequence dependent (or independent of the sequence) physiochemical properties of ONs since any particular ON of a defined sequence, being unique in the preparation, cannot be expected to contribute any meaningful activity derived from its specific nucleotide sequence.

Figure 1A:
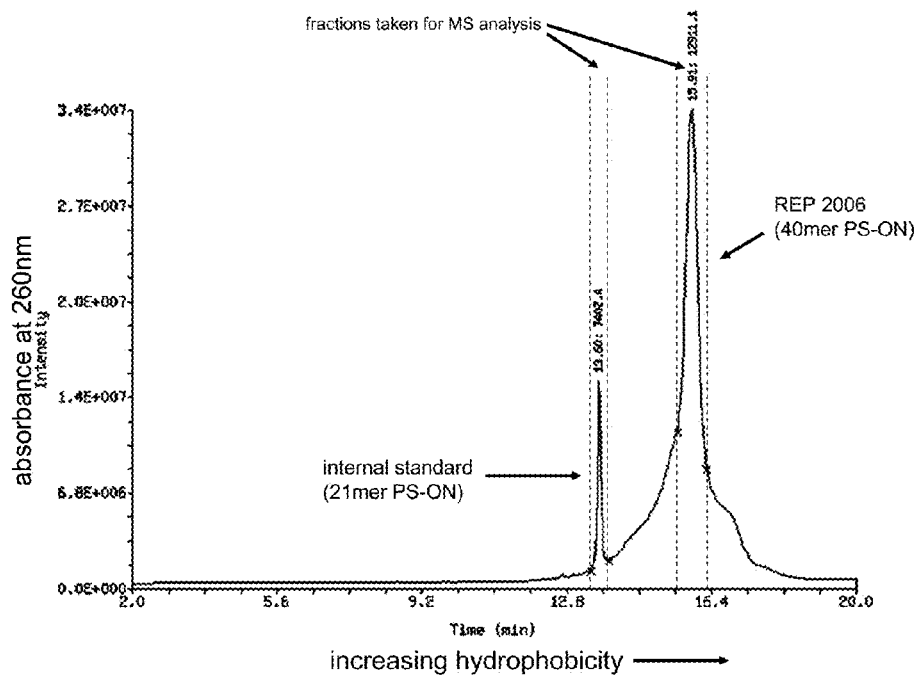
FIG. 1 illustrates the common physiochemical features of ONs. A) Co-separation of REP 2006 and a 21mer phosphorothioate ON with a defined sequence by high performance liquid chromatography. B) Identification of species in the 21mer ON by mass spectroscopy. C) Identification of species in the REP 20060N by mass spectroscopy.
Figure 1B:
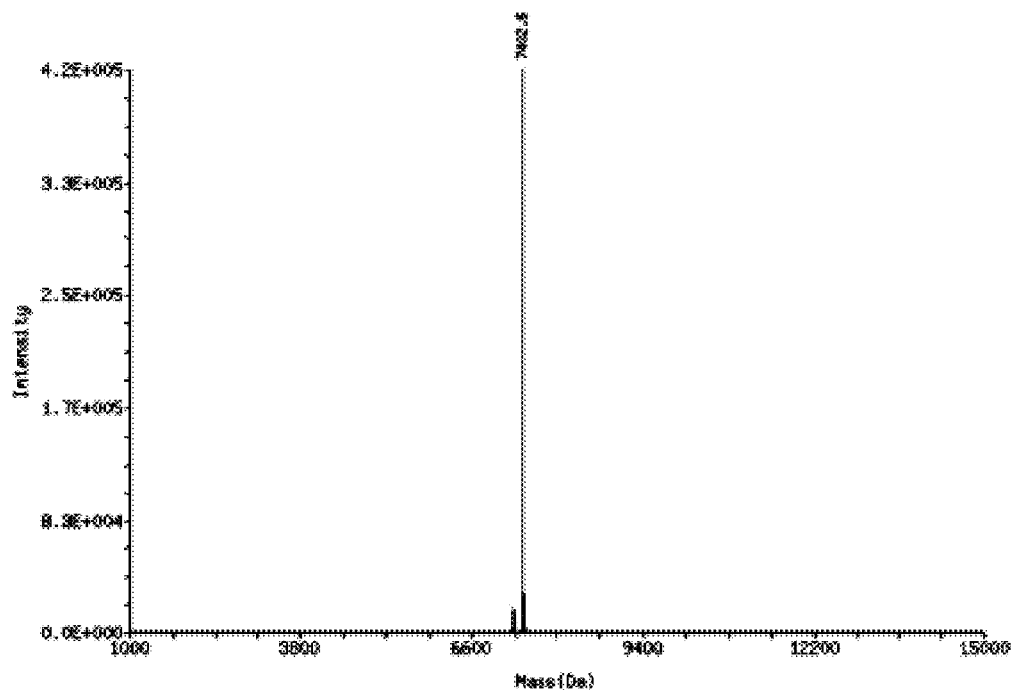
Figure 1C:
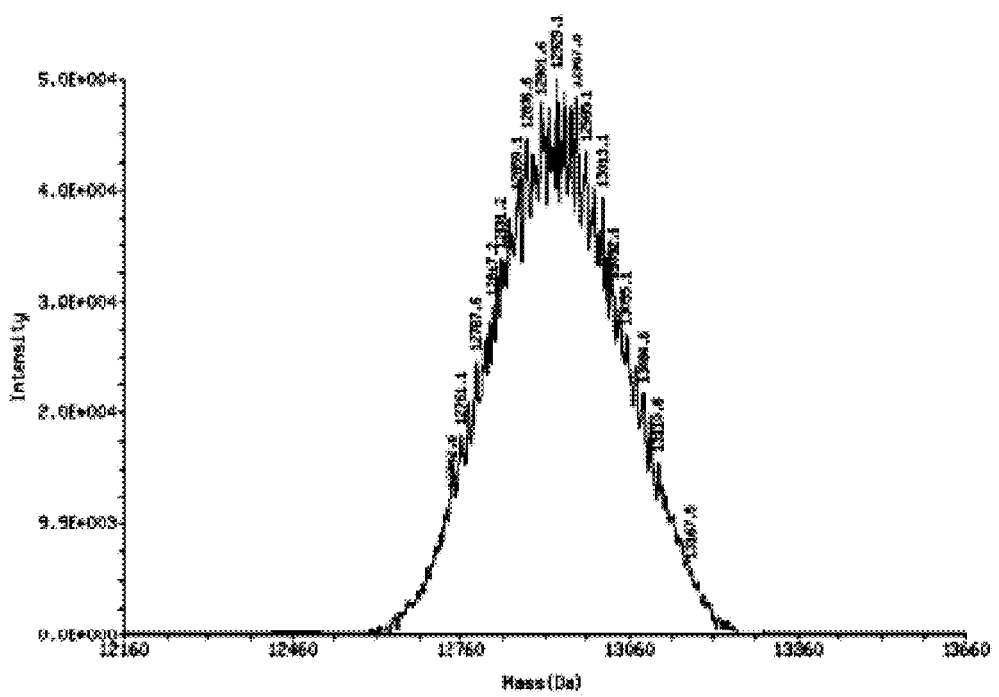

As further illustration of this concept, Example I compares the characterization of REP 2006 (a 40mer ON with a degenerate, completely phosphorothioated sequence) with a 21mer ON of a defined sequence (also completely phosphorothioated) by high pressure liquid chromatography and mass spectrometry and clearly shows that any ON with a similar size and chemical modification (i.e. phosphorothioation) will have highly similar (if not identical) physiochemical features which are not affected by the sequence of nucleotides present (see FIGS. 1A-C).

In the present application, the term "nucleic acid polymer" or NAP is intended to identify any single stranded ON which contains no sequence specific functionality. The biochemical activity of NAPs are not dependent on Toll-like receptor recognition of ONs, hybridization with a target nucleic acid or aptameric interaction requiring a specific secondary/tertiary ON structure derived from a specific order of nucleotides present. NAPs can include base and or linkage and or sugar modifications as described above.

ONs can exert their therapeutic effects by numerous mechanisms which are either sequence dependent or sequence independent. Sequence dependent mechanisms are those which require a specific nucleic acid sequence for their activity and where the activity is reduced by one or more alterations in the nucleotide sequence present. This specific sequence may encompass the entire length of the ON or only a portion of it (a sequence motif). Examples of sequence dependent ONs include:

1. Antisense ONs (either singled stranded or double stranded (e.g. small interfering RNA (siRNA) or small hairpin RNA (shRNA)) are complimentary to a specific portion of a messanger RNA (mRNA) of interest and when introduced into a cell, they direct the degradation of specific mRNAs by RNAse H or the RNA-induced silencing complex (RISC).
2. Stearic blocking ONs are single stranded antisense ONs which are complimentary to a specific portion of a mRNA but which are engineered to not activate RNAse H. The hybridization of these ONs to their target mRNA results in a double stranded portion which provides stearic hindrance to proteins normally acting on the mRNA. Such ONs can be employed to block translation of a particular mRNA or to interfere with the post-transcriptional splicing and maturation of a particular mRNA. Such ONs may be engineered to block the activation of RNAse H (since it is not integral to the mechanism of action of these ONs) by 2' ribose modifications throughout (such as 2' O methylation).
3. Aptamers are ONs which adopt a specific three dimensional conformation capable of specific protein interaction and which do not readily interact with host DNA or RNA. Aptamers can also include Spiegelmers, which use L-nucleotides instead of D-nucleotides to confer high enzymatic stability to the ON.
4. Immunostimulatory ONs utilize a specific timer nucleic acid motif (XXCGXX) to stimulate the immune response in mammals. The optimal motif varies from species to species but is strictly dependent on a specific sequence conforming to the XXCGXX motif.
5. Micro RNAs (miRNAs) bind to and block the function of naturally occurring micro RNA molecules which are involved in the regulation of various biochemical pathways.

The only reported example of sequence independent ONs are phosphorothioated NAPs, which selectively interact with amphipathic protein structures in a size (length) dependent fashion by virtue of their physiochemical properties as amphipathic polymers.

Several antiviral polypeptide-based drugs are currently approved for the treatment of viral infections which include pegylated interferon $\alpha$-2a (for the treatment of hepatitis B (HBV) and hepatitis C(HCV)), interferon $\alpha$-2b (for the treatment of HBV), thymosin $\alpha$1 (for the treatment of HBV) and enfurtide (for the treatment of HIV-1). There are also other polypeptide-based drugs in development including a myristylated pre-s1 HBV surface antigen protein fragment (myrcludex B, Petersen et al., 2008, Nature Biotech. 26: 335-341) for the treatment of HBV and pegylated interferon $\lambda$1 (Muir et al., 2010 Hepatology 52: 822-832). Additionally, interferon $\lambda$1, $\lambda$2 and $\lambda$3 are also known to have antiviral activity (Friborg et al., 2013, Antimicrobial Agents and Chemotherapy 57: 1312-1322). In the case of pegylated or unpegylated interferons and others known immunomodulators (e.g. thymosin $\alpha$1), these polypeptides are active in stimulating their respective biochemical pathways which leads to the stimulation of an immune response to the viral infection in subjects. While these polypeptides may successfully stimulate the immune response, only a small fraction of patients with HBV or HCV infections achieve a complete control of their infection using these polypeptide-based drugs. Myrcludex B functions to block HBV entry into hepatocytes but its therapeutic benefit has yet to be demonstrated in human patients.

In addition to these polypeptides, there are other classes of polypeptides with known antiviral activity which may be useful in the treatment of a viral infection when combined with an ON chelate complex. Such polypeptides include cytokines such as but not limited to TNF-$\alpha$, IL-1$\beta$, IL-2, IL-4, IL-6, and interferon $\gamma$.

The methods for pegylation of therapeutically active polypeptides and the compatibility of pegylation with the biochemical activity of the polypeptides is well known in the art and consists of the linking of strands of polyethyleneglycol (PEG) to the polypeptide in question at specific amino acid residues. The primary function of pegylation is to increase the circulating lifetime of a polypeptide and also to reduce its immunogenicity. These features improve the tolerability of the polypeptide in question and reduce the frequency of dosing required for optimal therapeutic effect. It is further known in the art that the attachment of PEG residues to a polypeptide can be achieved without affecting the specific biochemical activity of the polypeptide in question. Pegylation is also known to increase the water solubility of the polypeptide in question, improving its ease of formulation. Numerous examples of pegylated polypeptides are known in the art and include: Mircera™ a pegylated form of erythropoietin; Neulasta™, a pegylated form of human granulocyte colony-stimulating factor; Pegasys™ a pegylated form of human interferon $\alpha$-2a; Peg-Intron™, a pegylated form of human interferon $\alpha$-2b; and pegylated interferon $\lambda$1 (which is currently in clinical development). Therefore, the disclosure of the compatibility of one pegylated polypeptide (i.e. pegylated interferon $\alpha$-2a) in a composition with an ON chelate complex provides general enablement of the compatibility of any pegylated polypeptide with an ON chelate complex in general, and especially for pegylated versions of particular unpegylated polypeptides which are present in the current disclosure to be compatible with an ON chelate complex (i.e. thymosin $\alpha$1, interferon $\alpha$-2b and interferon $\lambda$1).

Several antiviral ON-based drugs are currently in development for the treatment of viral infections which include the phosphorothioated NAPs REP 9AC (REP 2055), REP 9AC' (REP 2139) and REP 9AC$^m$ (REP 2148) for the treatment of HBV; miravirsen for the treatment of HCV (Janssen et al., 2013, NEJM, March 27); and ALN-RSVO1 for the treatment of respiratory syncytial virus (RSV) (Zamora et al., 2011, Am. J. Resp. Crit. Care Med., 183: 531-538). Each of these has a different mechanism of action: NAPs prevent the release of the HBV surface antigen protein into the blood (a protein which inhibits immune function) as described in Example V, miravirsen (a miRNA) blocks the action of the micro RNA mir-122 which is known to play a role in HCV replication and ALN-RSV01 (a sRNA) blocks the synthesis of the RSV N nucleocapsid protein, preventing the production of RSV virions. All of these ON drugs are very effective in eliciting their intended effects in subjects: REP 9AC/REP 9AC'/REP 9ACm block the intracellular transit and secretion of HBV subviral particles (SVPs) which result in the clearance of the HBV surface antigen in the blood which in turn elicits a reduction in HBV virus in the blood; miravirsen works well to inhibit mir-122 function with is involved in HCV replication; and ALN-RSV-01 works well to block RSV capsid protein production. However in all cases where these ON based compounds are administered parenterally, they are associated with administration-related side effects such as fever, chills, shivering when administered by intravenous infusion or pain, inflammation or induration at the injection site when administered by subcutaneous administration. More importantly, while all of these ON-based drugs have their intended effects in subjects, the overall therapeutic outcome is far from what would be desirable: only a fraction of patients undergoing treatment with these drugs achieve a substantial antiviral response or complete control of their infection during treatment or after treatment is removed.

It is therefore desirable to prepare any of these ON-based antiviral drugs as ON chelates (in order to minimize their administration-related side effects and potentially improve their pharmacokinetic properties) and combine them with one or more antiviral polypeptides (such as pegylated interferon α-2a, interferon α-2b or thymosin α1 or pegylated interferon λ1) in the same formulation. The specific antiviral effects of the ON-based compounds (as chelates), coupled with the immunostimulatory antiviral effects of the polypeptides could have an improved beneficial effect in eliciting a more fully potentiated antiviral response in subjects and lead to a larger fraction of subjects achieving complete control of their infection when compared to either drug used separately.

It may be useful to treat a particular viral infection with a pharmaceutical composition comprising at least one antiviral ON chelate complex and at least one antiviral polypeptide or pegylated polypeptide to achieve an improved antiviral response in a subject.

It may be useful to treat a particular viral infection with at least one antiviral ON chelate complex and an antiviral polypeptide wherein each of these compounds is administered separately in different pharmaceutical compositions, whether by the same route of administration or not.

In order to provide the best possible antiviral response in a subject, it may be necessary to add to the combination therapy of an antiviral ON chelate and an antiviral polypeptide, whether administered in the same or separate pharmaceutical compositions, a third non-ON, non-polypeptide drug. Such drugs can be (but are not restricted to): entecavir, tenofovir disoproxil fumarate, telbuvidine, adefovir dipivoxil, lamivudine, ribavirin, telaprevir, boceprevir, GS-7977, tegobuvir, zanamivir, oseltamivir, ganciclovir, foscarnet, acyclovir, zidovudine, abacavir, lopinavir, ritonavir and/or efavirenz. Such antiviral drugs can prevent the replication of the viral genome and or viral mRNA in many viruses such as HCV, HBV, HIV, influenza, RSV, and cytomegalovirus.

It is possible that the combination of the specific antiviral effects of the antiviral ON chelate complex, combined with the immunostimulatory effects of the antiviral polypeptides or pegylated polypeptides and the blockage of viral DNA/RNA replication by the non-ON, non-polypeptide drugs listed above, can provide the best and most potent therapeutic response in a subject with the viral infection and further increase the chance that the subject in question will achieve a durable control of the virus which can be sustained after treatment is halted.

The ON chelate complex in the formulation can be derived from any ON with antiviral activity, examples of which are provided in table 1.

TABLE 1

Examples of ONs which can be preparedas chelate complexes.

| ON class | Nucleic acid type | Sequence (5'-3') | Modifications |
|---|---|---|---|
| NAP | DNA | (AC)$_{20}$ (SEQ ID NO: 2) | All linkages PS |
| NAP | DNA | (CA)$_{20}$ (SEQ ID NO: 10) | All linkages PS |
| NAP | DNA | (A-5'MeC)$_{20}$ (SEQ ID NO: 11) | All linkages PS |
| NAP | DNA | (5'MeC-A)$_{20}$ (SEQ ID NO: 12) | All linkages PS |
| NAP | RNA | (2'OMeA-2'OMeC)$_{20}$ (SEQ ID NO: 13) | All linkages PS |
| NAP | RNA | (2'OMeC-2'OMeA)$_{20}$ (SEQ ID NO: 14) | All linkages PS |

TABLE 1-continued

Examples of ONs which can be prepared as chelate complexes.

| ON class | Nucleic acid type | Sequence (5'-3') | Modifications |
|---|---|---|---|
| NAP | DNA | (AG)$_{20}$ (SEQ ID NO: 3) | All linkages PS |
| NAP | DNA | (GA)20 (SEQ ID NO: 15) | All linkages PS |
| NAP | DNA | C$_{40}$ (SEQ ID NO: 1) | All linkages PS |
| NAP | DNA | (TC)$_{20}$ (SEQ ID NO: 5) | All linkages PS |
| NAP | DNA | (CT)$_{20}$ (SEQ ID NO: 16) | All linkages PS |
| NAP | DNA | (TG)$_{20}$ (SEQ ID NO: 6) | All linkages PS |
| NAP | DNA | (GT)20 (SEQ ID NO: 17) | All linkages PS |
| NAP | RNA | (2'OMe, 5'MeC-2'OMeA)$_{20}$ (SEQ ID NO: 4) | All linkages PS |
| NAP | RNA | (2'OMeA-2'OMe, 5'MeC)$_{20}$ (SEQ ID NO: 18) | All linkages PS |
| miRNA | LNA/ DNA | CCATTGTCACA$^m$CTC$^m$CA (SEQ ID NO: 7) | All linkages PS LNA in bold ($^m$C = 5'MeC) |
| miRNA | DNA/ RNA | Sequence corresponding to a host micro RNA | All linkages PS, may contain LNA or RNA with 2' ribose modification |
| antisense | DNA/ RNA | Sequence corresponding to a viral or host mRNA | All linkages PS, may contain a portion of RNA with 2' ribose modification or LNA |
| siRNA/ shRNA | Double stranded RNA/ DNA | Sequence corresponding to HBV X protein | May contain RNA with 2' ribose modification, may contain PS |
| siRNA | Double stranded RNA/ DNA | GGCUCCUUAGCAAAGUCAAG$_d$T$_d$T (SEQ ID NO: 8) + CUUGACUUUGCUAAGAGCC$_d$T$_d$T (SEQ ID NO: 9) Sequence corresponding to mRNA for RSV N protein mRNA | All RNA except for deoxythymidine ($_d$T), may contain PS |
| siRNA . shRNA | Double stranded RNA/ DNA | Sequence corresponding to a viral mRNA | May contain RNA with 2' ribose modification, may contain PS |

LNA = locked nucleic acid, PS = phosphorothioate, 2'OMe = 2' O methyl, 5'MeC = 5'methylcytosine The polypeptide in the formulation can have direct antiviral activity or be able to stimulate host-derived antiviral activity and can be the following:
  Thymosin α1;
  Any α-interferon or pegylated derivatives thereof;
  Any β-interferon or pegylated derivatives thereof;
  Any γ-interferon or pegylated derivatives thereof;
  Any λ-interferon or pegylated derivatives thereof;
  Interferon α-2a or α-2b or α-N3;
  Interferon β-1a or β-1b;
  Interferon γ-1b;
  Interferon λ1 or λ2 or λ3;
  Pegylated interferon α-2a or α-2b or λ1 or λ2 or λ3;
  Myrcludex B;
  Any antiviral cytokine or pegylated derivatives thereof;
  Thymic protein A; and/or
  Any polypeptide or pegylated polypeptide shown to have antiviral activity or immunostimulatory activity.

It is provided herein a demonstration that numerous different ON chelate complexes can be combined with different polypeptide or pegylated polypeptide drugs in a single pharmaceutical composition which does not affect the structure of either the ON or polypeptide.

These compositions can be used to administer both the ON chelate complex and the polypeptide drug(s) to a subject in need of such therapy at the same time and with a single mode of administration as demonstrated in Example VI below).

Furthermore, the above compositions may include physiologically and/or pharmaceutically acceptable carriers, adjuvants, vehicles and/or excipients. The characteristics of the carrier may depend on the route of administration. The term "pharmaceutically acceptable carrier, adjuvant, vehicle and/or excipient" refers to a carrier, adjuvant, vehicle or excipient that may be administered to a subject, incorporated into a composition of the present invention, and which does not destroy the pharmacological activity thereof. Pharmaceutically acceptable carriers, adjuvants, vehicles and excipients that may be used in the pharmaceutical compositions described herein include, but are not limited to, the following: ion exchangers, alumina, aluminum stearate, lecithin, self-emulsifying drug delivery systems ("SEDDS"), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat, sodium caprate or tetradecylmaltoside (TDM) or other TDM derivates of alkylated saccharides. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compositions of the present invention.

The compositions described herein may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compositions described herein may be administered by any suitable means, for example, orally, such as in the form of tablets, capsules, granules or powders; sublingually; buccally; parenterally, such as by subcutaneous, intravenous, intramuscular, intrathecal or injection or infusion techniques (e.g., as sterile injectable aqueous or non-aqueous solutions or suspensions); by inhalation; topically, such as in the form of a cream or ointment; or rectally such as in the form of suppositories or enema; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions, or, particularly in the case of extended release, by the use of devices such as subcutaneous implants or osmotic pumps. Thus, the above compositions may be adapted for administration by any one of the following routes: intraocular, oral ingestion, sublingual, enteric, inhalation, subcutaneous injection, intramuscular injection, intraperitoneal injection, intrathecal injection or infusion, intratracheal, intravenous injection or infusion, or topically.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, starch, magnesium stearate and/or lactose and/or other excipients, binders, extenders, disintegrants, diluents and lubricants such as those known in the art which do not interfere with oligonucleotide chelate stability. The present compositions may also be delivered through the oral cavity by sublingual and/or buccal administration. Molded tablets, compressed tablets or freeze-dried tablets are exemplary forms which may be used. Exemplary compositions include those formulating the present compositions with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

The effective amount of a compound described herein may be determined by one of ordinary skill in the art, and includes exemplary dosage amounts for an adult human of from about 0.1 to 50 mg/kg of body weight of active compound per day, which may be administered in a single dose or in the form of individual divided doses, such as (but not limited to) from 1 to 5 times per day or from 1 to 7 doses per week. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combination, and severity of the particular condition. Preferred subjects for treatment include animals, most preferably mammalian species such as humans, and domestic animals such as dogs, cats and the like.

It is also provided herein an example of the beneficial antiviral activity of an antiviral oligonucleotide chelate complex and an antiviral polypeptide when used in combination to treat human patients with a viral infection.

The present disclosure will be more readily understood by referring to the following examples.

EXAMPLE I

Characterization of Degenerate ONs

FIG. 1A details the separation by HPLC (using a hydrophobic column) of two ON preparations which are co-injected into the column at the same time. The first of these is called the internal standard and is a 21 mer phosphorothioate ON with a specific defined sequence, the second is REP 2006 (a 40mer degenerate phosphorothioate ON). Both of these species separate into distinct defined peaks based only on their physiochemical properties (i.e. size and hydrophobicity); the sequence of nucleotides present in each of these ONs has no meaningful impact on their physiochemical properties and therefore has no impact on their separation. As such, the internal standard elutes off the column as a tightly defined peak with smaller retention time as compared to REP 2006, only due to the difference in the size of these two ON polymers. Note that the shoulders on either side of the REP 2006 peak are due to failure sequences typical in the production of longer ONs. Despite the heterogeneous sequence nature of REP 2006, it resolves as a similarly well defined peak by HPLC as the 21mer specific sequence which illustrates the common physiochemical properties of all species in the REP 2006 preparation, even though there are a very large number of different sequences present. Subsequent to the HPLC separation of the REP 2006 and 21-mer peaks, these can be subjected to mass spectroscopy (MS) to identify the species present within these defined peaks (FIGS. 1B and 1C).

In FIG. 1B, the 21mer is resolved into a single species with MW of 7402.6 Da, consistent with this PS-ON having a defined sequence. However, MS analysis of REP 2006 (FIG. 1C) reveals an extremely large number of species present whose mass range has an almost perfect normal distribution, consistent with its completely degenerate nature. This mass range goes from C40 (the smallest species) to A40 (the largest species) and the prevalence of these species are extremely small with the number of species increasing (peak intensity) as their mass approaches the center of the mass range. This is because an increasingly larger number of different sequences will result in a similar mass. The fact that all of the different ON species present in REP 2006 have the same retention time on a hydrophobic column during HPLC separation clearly demonstrates that ONs of the same size and with the same chemical modifications (i.e. phosphorothioation) will likely have highly similar (if not identical) physiochemical properties and as such, can be considered functionally similar in any application or property which is not dependent on the sequence of nucleotides present in a particular ON molecule. Thus, any ON chelate complex formation observed with any particular degenerate ON (e.g. REP 2006), cannot be dependent on the sequence of ONs present and must be dependent on the conserved physiochemical properties of any ON.

EXAMPLE II

Formation of Chelate Complexes with Antiviral ONs

REP 2031, REP 2055, REP 2057 and REP 2139 are nucleic acid polymers (NAPs) with broad spectrum antiviral activity against HIV, HSV, cytomegalovirus, LCMV, HCV and other enveloped viruses (Bernstein et al., 2008, Antimicrobial Agents Chemother. 52: 2727-2733; Cardin et al., 2009, Virology J. 6: 214; Vaillant et al., 2006, Antimicrobial Agents Chemother., 50: 1393-1401; Guzman et al., 2007, Antiviral Therapy, 12: 1147-1156; Lee et al., Virology, 372: 107-117; Matsumura et al., 2009, Gastroenterology 137: 673-681). All of these compounds are 40mer fully phosphorothioated ONs with the 5'-3' sequences $C_{40}$ in the case of REP 2031 (SEQ ID NO:1), $(AC)_{20}$ in the case of REP 2055 (SEQ ID NO: 2), $(AG)_{20}$ in the case of REP 2057 (SEQ ID NO: 3) and $(2'OMeA-2'OMe, 5'MeC)_{20}$ in the case of REP 2139 (SEQ ID NO: 18). While REP 2031, REP 2055 and REP 2057 are DNA ONs, REP 2139 is an RNA ON wherein all riboses are 2' O methyl modified and all cytosines are 5' methylated.

Figure 3:
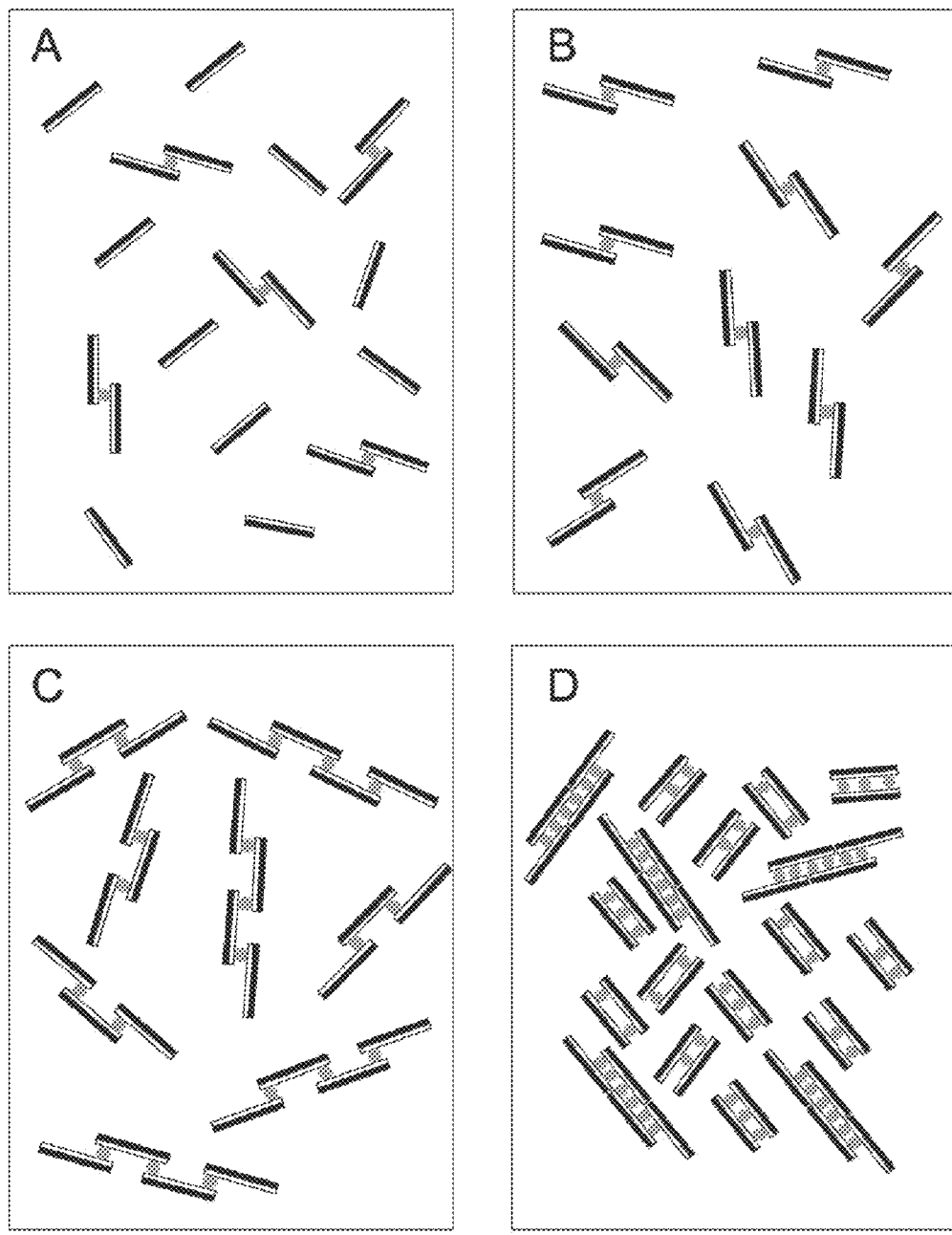
FIG. 3 illustrates the model for solution behavior of ONs in the presence of divalent or multivalent metal cations at varying ON and divalent metal cation concentrations. A) Low divalent/trivalent metal cation, low ON concentrations yield dimers or low order ON chelate complexes. B) Increasing divalent/trivalent metal cation concentrations yield more complete ON chelate complex formation in the solution. C) Further increasing ON concentrations in the presence of divalent or trivalent metals are capable of yielding higher order ON chelate complexes with increasing metal concentrations. All the chelate complexes in (A) through (C) are soluble in aqueous solution by virtue of having hydrophilic surfaces still exposed to the aqueous environment thus maintaining solubility. D) At sufficient ON and metal concentration, all hydrophilic surfaces are now constrained within the ON chelate complexes, leaving only the hydrophobic surfaces exposed to the aqueous environment. This results in precipitation of the ON chelate complex.
Figure 4:
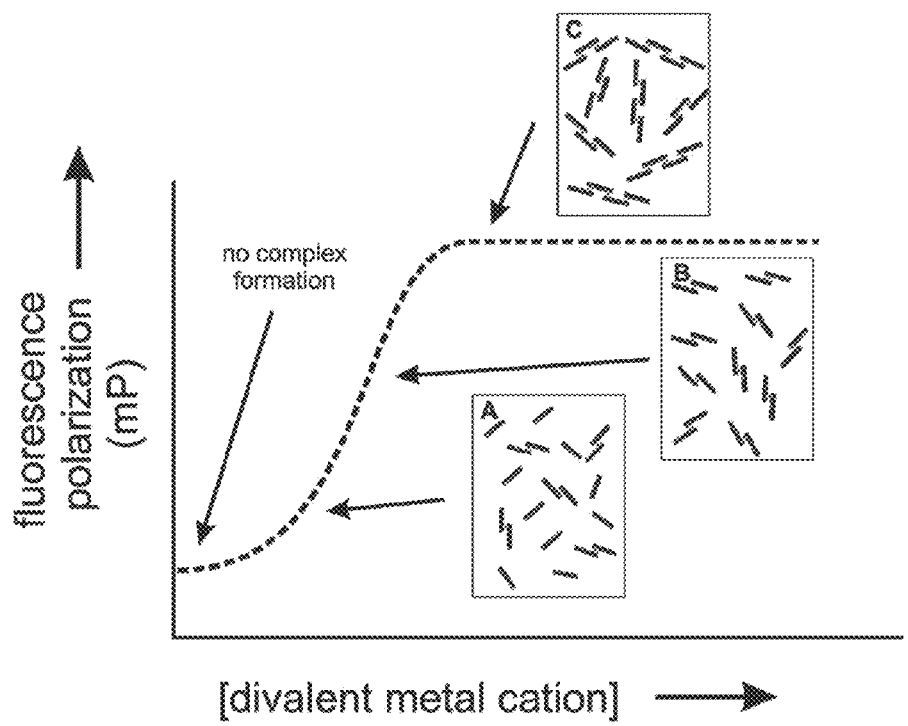
FIG. 4 illustrates the effect of the solution behavior of fluorescent-ON chelate complexes on fluorescence polarization. With increasing metal concentration, the size (and mass) of ON chelate complex formation also increases (see FIG. 3) and thus tumbles more slowly in solution. This slower tumbling of the complex in solution leads to increased fluorescence polarization and an increased mP value.

The formation of chelate complexes with these antiviral ONs was examined with fluorescence polarization using 3' FITC labeled derivatives of these compounds. During ON synthesis, each ON was conjugated to fluorescein isothiocyanate (FITC) at the 3' end by a rigid 3 carbon linker using well established reagents and synthesis protocols. These ONs were cleaved from the synthesis and left as ammonium salts. Each of these ONs was prepared as a 0.5 mM stock in 1 mM TRIS (pH 7.2). These stocks were used to prepare 3 nM fluorescent ON solutions in FP buffer (10 mM TRIS, 80 mM NaCl, 1 mM EDTA, 10 mM β-mercaptoethanol and 0.1% Tween®-20). EDTA was present to remove any divalent metals present in the solution prior to FP measurements. Each of these buffer solutions also contained 80 mM NaCl to assess ON complex formation in the presence of a molar excess of monovalent cations. To each fluorescent ON in solution was added ACS grade chloride salts of divalent (2+) metals (as described in Table 2). The formation of dimers or higher order ON chelate complexes was monitored by an increase in fluorescence polarization (quantified by the dimensionless unit "mP") so that increased formation of ON chelate complexes resulted in larger changes in mass (see FIG. 3). The resulting slower tumbling of these ON chelate complexes in solution leads to increased polarization of emitted fluorescence (see FIG. 4). The results of these experiments are presented in Table 2.

TABLE 2

ON chelate formation with NAPs with different divalent metals

| | fluorescence polarization (mP) | | | | | | | |
|---|---|---|---|---|---|---|---|---|
| | calcium (as $CaCl_2$) | | | | magnesium (as $MgCl_2$) | | | |
| | absent | | present | | absent | | present | |
| ON | avg | stdev | avg | stdev | avg | stdev | avg | stdev |
| REP 2006-FL | 92 | 4.24 | 183 | 4.94 | 97 | 2.82 | 187 | 1.41 |
| REP 2031-FL | 58.5 | 23.3 | 114.5 | 2.1 | 52.5 | 3.5 | 89.5 | 2.1 |
| REP 2055-FL | 48 | 5.7 | 172 | 15.6 | 60.0 | 2.8 | 151.0 | 7.8 |
| REP 2057-FL | 59.5 | 1.4 | 152.5 | 6.36 | 61 | 4.24 | 136.5 | 2.83 |
| REP 2139-FL | 48 | 7.1 | 138.5 | 10.6 | 46 | .4 | 142.5 | 7.8 |

Average and standard deviation were based on two replicate measurements.

In each case, significant increases in fluorescence polarization were seen with all fluorescently labeled ONs in the presence of calcium and magnesium, indicating the formation of ON chelate complexes with these divalent metal cations. These results demonstrate the following:

REP 2006, REP 2031, REP 2055, REP 2057 and REP 2139 form dimers and higher order complexes in the presence of magnesium and calcium cations. These complexes are expected to form with all other multivalent metal cations and with any ON (as shown with the degenerate NAP REP 2006). The formation of these ON complexes involves the interaction of these ONs with these divalent metal cations.

The formation of ON complexes cannot be due to hybridization between nitrogenous bases vial traditional Watson-Crick interactions because REP 2031, REP 2055, REP 2057 and REP 2139 cannot self-hybridize under the experimental conditions employed.

The formation of these ON complexes is stable and soluble in aqueous solution and since these complexes appear to incorporate the divalent metal in question as part of the complex formed, these ON complexes have the effect of chelating the divalent metal in question from the solution in which the ON complex was formed.

EXAMPLE III

Preparation of Compositions Containing ON Chelate Complexes and Polypeptides

The preparation of compositions containing ON chelate complexes and a polypeptide was undertaken using five different antiviral ONs and four antiviral polypeptides. The ONs used were NAPS which have been previously shown to have broad spectrum antiviral activity in enveloped viruses, including HBV, HCV, influenza, RSV, Ebola, HSV-1 and HSV-2. These ONs are REP 2006 (a 40mer degenerate phosphorothioated NAP), REP 2055 (SEQ ID NO: 2), REP 2057 (SEQ ID NO: 3), REP 2139 (SEQ ID NO: 18) and REP 2148 (SEQ ID NO: 11). These NAPs were prepared by standard solid phase synthesis conditions in a flow reactor and additionally salt-exchanged to replace the ammonium counter-ions with sodium counter-ions during the purification. The theoretical free acid molecular weights of these ONs are (12612-13092), 12612, 13413 and 14094 and 12893 Da respectively. The antiviral polypeptides used were interferon α-2b, thymosin α1, pegylated interferon α-2a, and interferon λ1 (IL-29), which have all been shown to have antiviral activity (Yang et al., 2008, Antiviral Res., 77: 136-141; Fried et al., 2002, N. Engl. J. Med., 347: 975-982; Friborg et al., 2013, Antimicrob. Agents Chemother. 57: 1312-1322). All ONs were synthesized according to the current standards in the art for solid phase oligonucleotide synthesis and were prepared as sodium salts suitable for in vivo administration using accepted methods and lyophilized to <10% water content prior to storage. REP 2006, REP 2055, REP 2057 and REP 2148 were unpurified preparations containing minor amounts of incomplete synthesis products normally occurring during solid phase synthesis. REP 2139 was prepared as a higher purity preparation where most products of incomplete synthesis were absent. REP 2006, REP 2057 and REP 2139 were pre-prepared as solutions in normal saline and adjusted to 25 mg/ml during chelate formation. REP 2055 was also pre-prepared as a solution in normal saline but adjusted to 12.5 mg/ml during chelate preparation. Thymosin α1 is a synthetic amino terminal acylated peptide of 28 amino acids with a molecular weight of 3108 Da and was obtained in a commercial preparation (Zadaxin™) and prepared as a 1.6 mg/ml solution in water for injection. Interferon α-2b was produced in *E. coli* by recombinant DNA techniques and has a molecular weight of 19271 Da. Interferon α-2b was obtained in a commercial preparation (Intron A™) and prepared as a $1 \times 10^7$ IU/ml solution in water for injection which also contained 1 mg/ml of human serum albumin (having a molecular weight of about 66500 Da). Pegylated interferon α-2a is a covalent conjugate of interferon α-2a and a single branched bis-monomethoxy polyethylene glycol chain with a total approximate molecular weight of 60000 Da. Pegylated interferon α-2a was obtained in a commercial preparation (Pegasys™) prediluted in water for injection containing trace amounts of benzyl alcohol at a concentration of 360 ug/ml. Purified recombinant interferon λ1 (IL-29) was obtained as a carrier free solution of 0.5 mg/ml in phosphate buffered saline from Ebiosciences (SanDiego, U.S.A.) and has a molecular weight of ~20 kDa as determined by gel electrophoresis.

Calcium chloride was obtained as a 100 mg/ml USP preparation of $CaCl_2.2H_2O$ in water for injection (Lifeshield™ by Hospira). Magnesium sulfate was obtained as a 500 mg/ml USP preparation of $MgSO_4.7H_2O$ in water for injection (Baxter) and diluted to 100 mg/ml in normal saline. To prepare ON chelate complexes containing calcium, magnesium or calcium and magnesium, these metal salt solutions were gradually added dropwise to the ON solution with constant mixing until the desired ratio of metal salt to ON was achieved. For calcium chelate complexes, the ratio of 30 mg of calcium chloride per 100 mg of ON was obtained in solution, except for REP 2148 calcium chelate complex, which contained 20 mg calcium chloride per 100 mg ON. For magnesium chelate complexes, the ratio of 30 mg of magnesium sulfate per 100 mg of ON was obtained in solution. For mixed calcium/magnesium chelate complexes, the ratio of 15 mg calcium chloride and 15 mg magnesium sulfate per 100 mg of ON was obtained in solution. This methodology has been shown to result in the formation of ON chelate complexes (as described in U.S. application publication no. 2012/0046348). At the end of this procedure, the ON chelate complex was a clear homogenous solution with a very pale yellowish color.

ON chelate complex/polypeptide or pegylated polypeptide compositions were prepared by gently mixing the ON chelate complex solution with the polypeptide or pegylated polypeptide solution in a ratio of 1:1 to a final volume of 1 ml.

EXAMPLE IV

Characterization of Compositions Containing ON Chelate Complexes and Polypeptides To confirm the identities of the ONs and polypeptides or pegylated polypeptides contained in the compositions prepared in Example III, they were subjected to analysis by high pressure liquid chromatography (HPLC) followed by electrospray ionization mass spectrometry (ESI-MS). Because of the wide variation in the masses and chemistries of the ON and polypeptide or pegylated polypeptide species present in these compositions, three different HPLC methodologies were used for analysis:

Oligo method: Solid phase: 2×50 mm ACE™ C18 (3 um)
    Mobile phase: A=1/0.1% HFIPA/DIEA
        B=65/0.075/0.0375% ACN/HFIPA/DIEA
    Gradient: 5-25% B over 20 min
        70% B over 2 min at 60° C.
    Flow rate: 0.4 ml/min
Protein method 1: Solid phase: 2×50 mm PLRP-s (Agilent™) 4000A (8 um)
    Mobile phase: A=0.05% TFA in ACN
        B=0.05% TFA in ACN
        C=0.1% $NH_4OH$ in $H_2O$
        D=0.1% $NH_4OH$ in 40/40/20 ACN/MeOH/$H_2O$
    Gradient: 80/20% C/D wash for 1 min to waste
        (optionally 20% D wash for 1 min to waste)
        20%-100% D over 15 min, 100% B over 2 min
        (optionally 20-70% B over 16 min)
    Flow rate: 0.5 ml/min for wash
        0.3 ml/min for gradient
Protein method 2: Solid phase: 2×50 mm PLRP-s (Agilent™) 4000A (8 um)
    Mobile phase: A=0.05% TFA in ACN
        B=0.05% TFA in ACN
        C=0.1% $NH_4OH$ in $H_2O$
        D=0.1% $NH_4OH$ in 40/40/20 ACN/MeOH/$H_2O$ Gradient: 80/20% C/D wash for 1 min to waste
   80/20% A/B-100% B over 15 min
   100% B over 2 min
Flow rate: 0.5 ml/min for wash
   0.3 ml/min for gradient Instrumentation used was a LTQ-Orbitrap Discovery operated in LTQ scan mode with negative ions for the oligo method and in Orbitrap high mass scan mode at 7500 resolution with positive ions for both protein methods. Acoynyms: ACN=acetonitrile, TFA=trifluoroacetic acid, HFIPA=hexafluoroisopropanol, DIEA=N,N-diisopropylethylamine.

Figure 5:
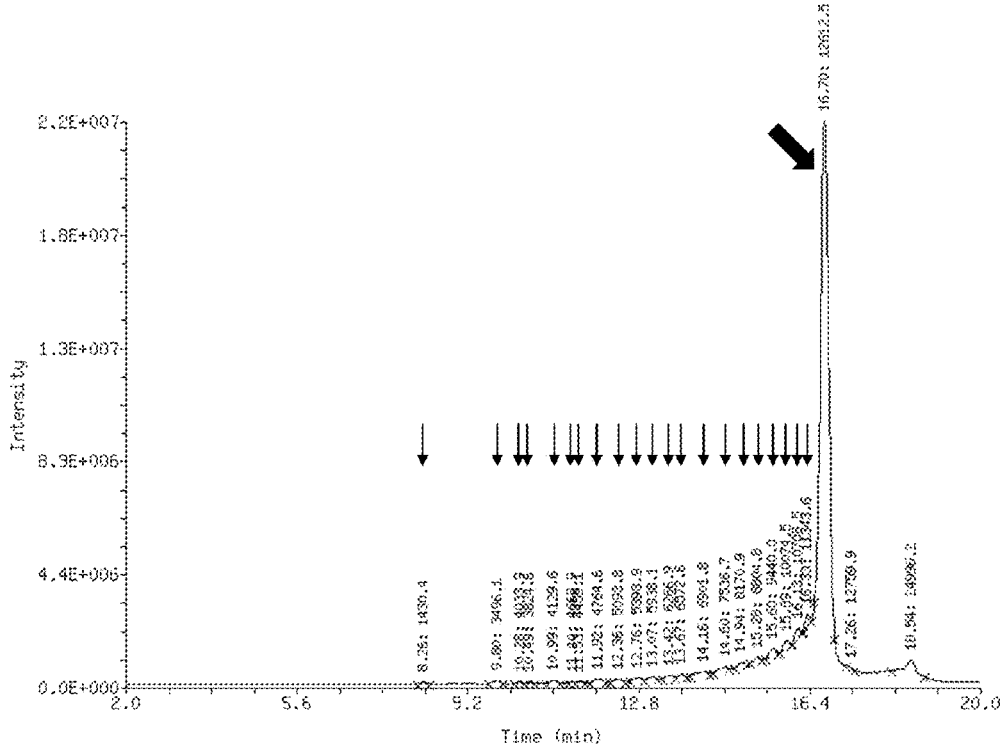
FIG. 5 illustrates a HPLC separation of the REP 2055 calcium chelate/interferon α-2b composition using the oligo method as depicted in Example IV. The full length ON peak (large arrow) is preceded in the chromatogram by the minor products of incomplete synthesis (small arrows) and are typically ONs with sequences missing one or more nucleotides compared to the full length ON sequence. This HPLC profile is typical for all non-purified ONs used (REP 2055, REP 2057 and REP 2148).
Figure 6:
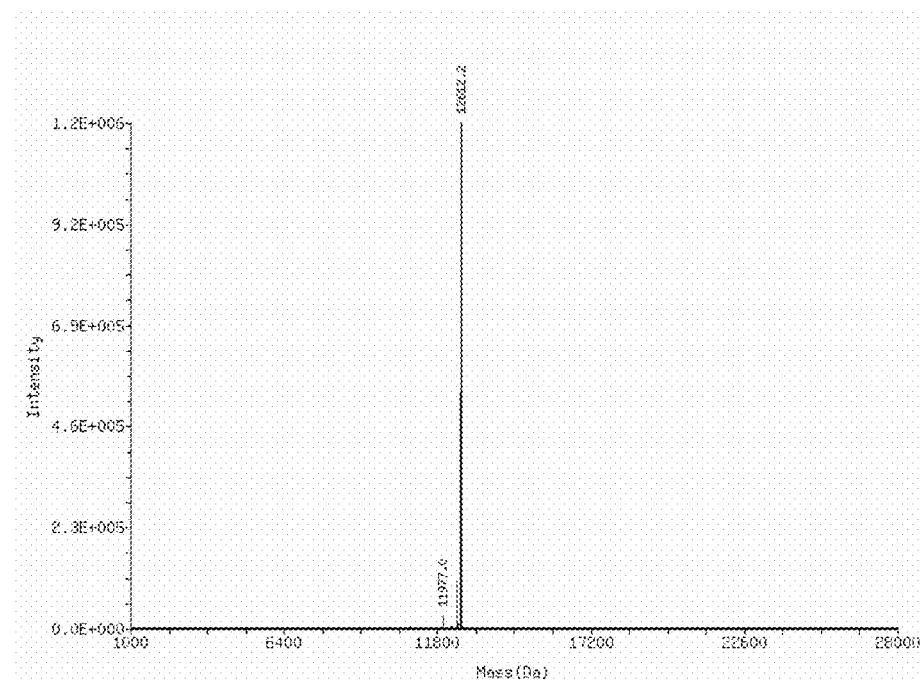
FIG. 6 illustrates an ESI-MS analysis of oligonucleotide content in REP 2055 calcium chelate/interferon α-2b composition from the HPLC peak at 16.70 min in FIG. 5. The observed mass of the primary species is 12612.2 Da, identifying it as REP 2055 (expected m.wt.=12612.5).
Figure 7:
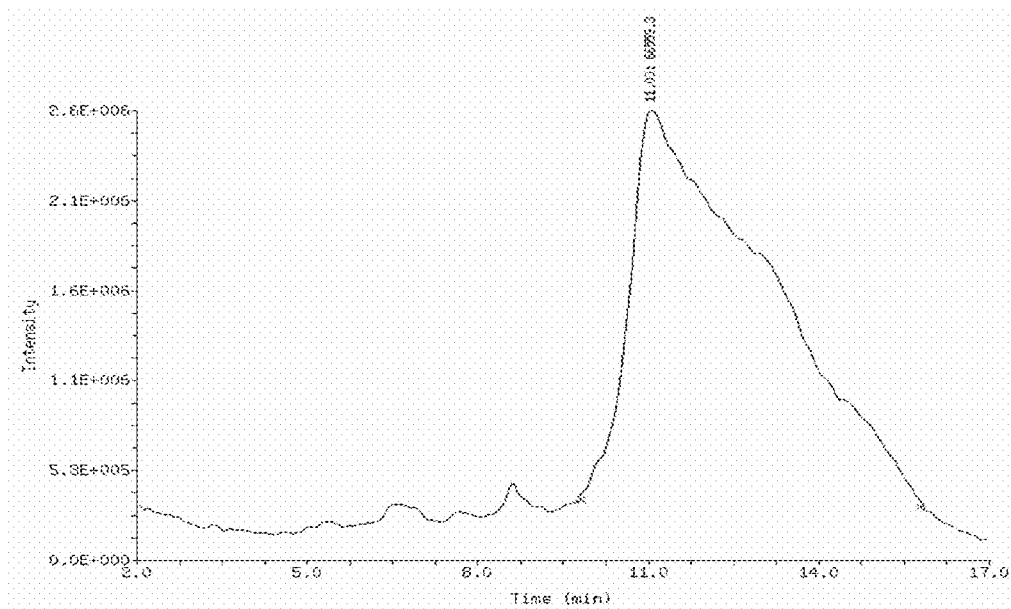
FIG. 7 illustrates a HPLC separation of the REP 2055 calcium chelate/interferon α-2b composition using protein method 1 (see Example IV).
Figure 8:
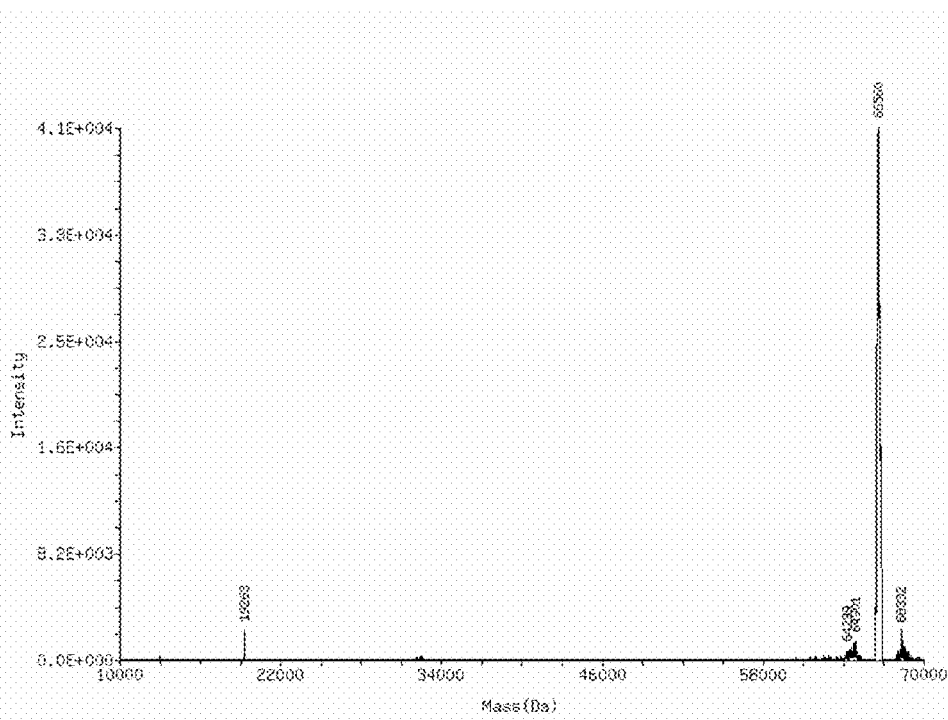
FIG. 8 illustrates an ESI-MS analysis of peptide content in REP 2055 calcium chelate/interferon α-2b composition from the HPLC peak at 11.03 min in FIG. 7. The observed mass peak at 19263 Da corresponds to interferon α-2b (expected m.wt.=19271 Da) and the peak at 66560 Da corresponds to human albumin.
Figure 95:
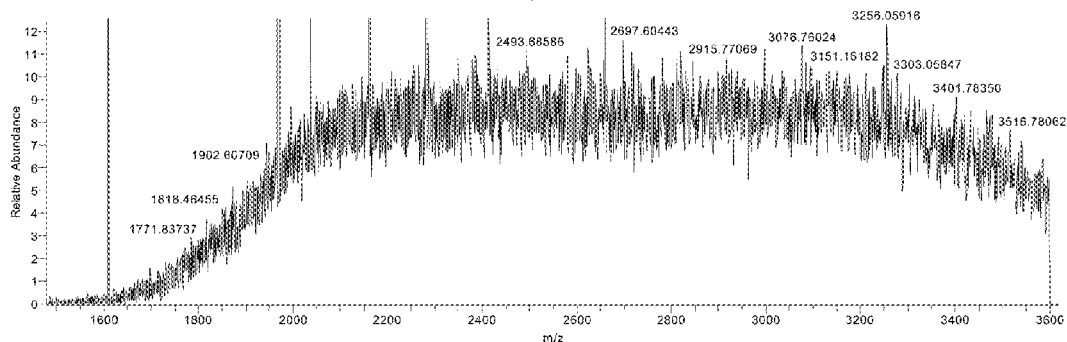
FIG. 95 illustrates an ESI-MS analysis of peptide content in REP 2139 mixed calcium-magnesium chelate/pegylated interferon α-2a composition from the HPLC peak at 13.46 min in FIG. 94.

Results from these analyses can be found in FIGS. 5-95. All HPLC chromatograms are plotted from total ion current (TIC) data where peak retention times are accompanied by mass identifications from subsequent ESI-MS (except for FIGS. 39, 43, 47, 51, 55, 77, 81, 91 and 95 where this was prevented by the presence of the polyethylene glycol conjugate in pegylated interferon α-2a). For the cases of compositions containing ON chelate complexes and thymosin α1, the oligo method was sufficient to analyze both species simultaneously. For the other compositions containing the large molecular weight proteins, ON analysis and polypeptide analysis was conducted on the same sample but using different HPLC methodologies (as indicated in FIGS. 5-95).

Figure 9:
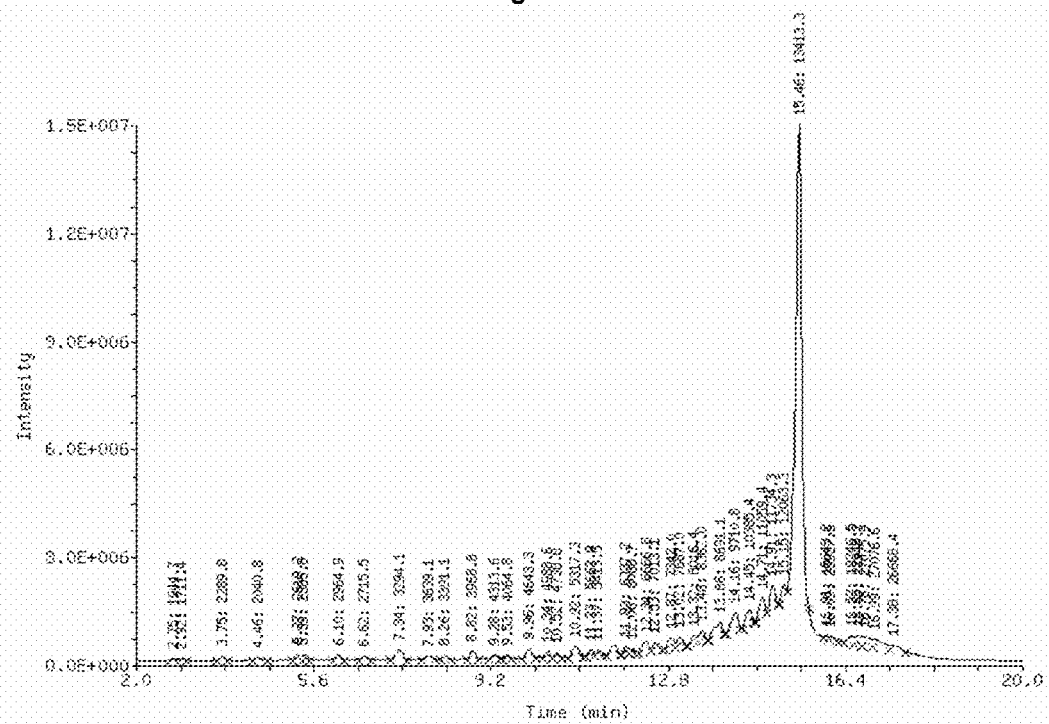
FIG. 9 illustrates a HPLC separation of the REP 2057 calcium chelate/interferon α-2b composition using the oligo method described herein (see example IV). As in FIG. 5, minor products of incomplete synthesis precede the main peak of the full length REP 2057 sequence.
Figure 10:
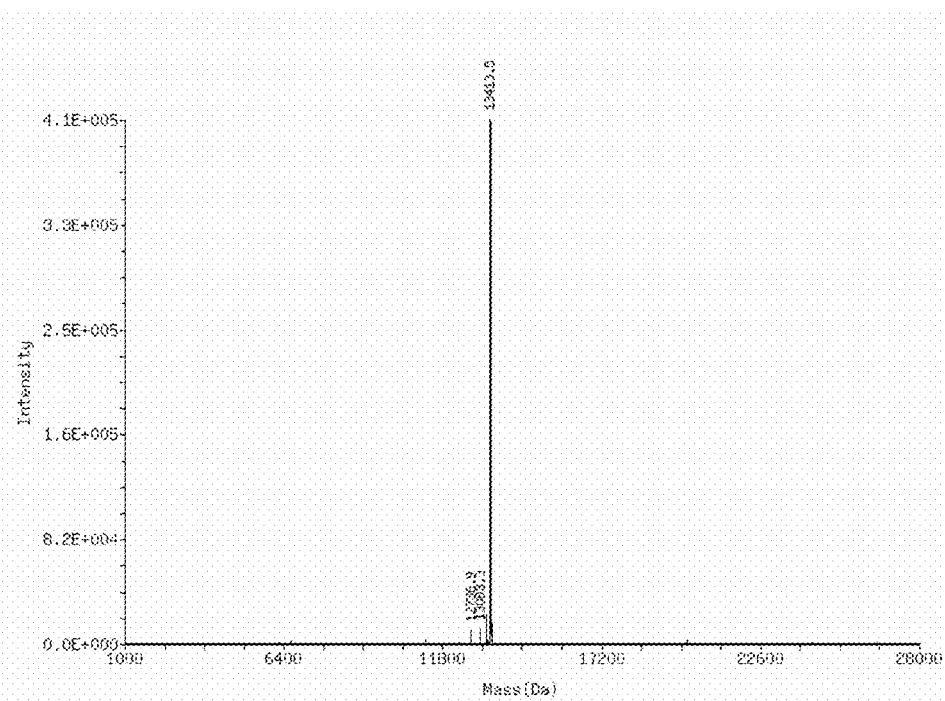
FIG. 10 illustrates an ESI-MS analysis of oligonucleotide content in REP 2057 calcium chelate/interferon α-2b composition from the HPLC peak at 15.46 min in FIG. 9. The observed mass of the primary species is 13413.5 Da, identifying it as REP 2057 (expected m.wt.=13413.3).
Figure 11:
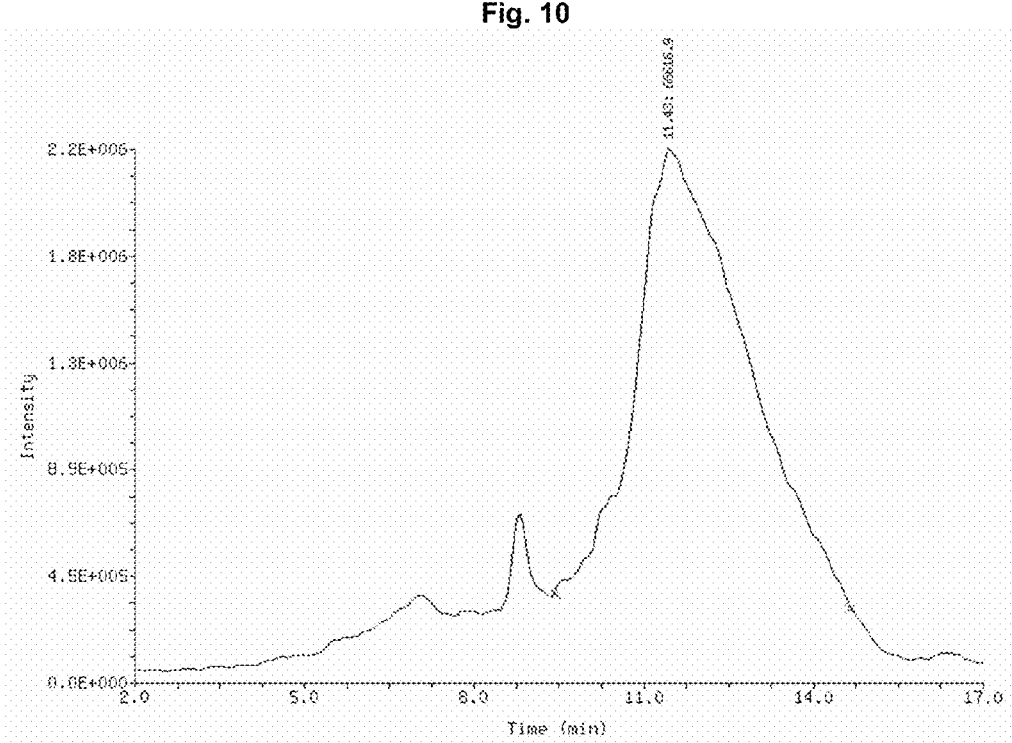
FIG. 11 illustrates a HPLC separation of the REP 2057 calcium chelate/interferon α-2b composition using protein method 1 described herein (see Example IV).
Figure 12:
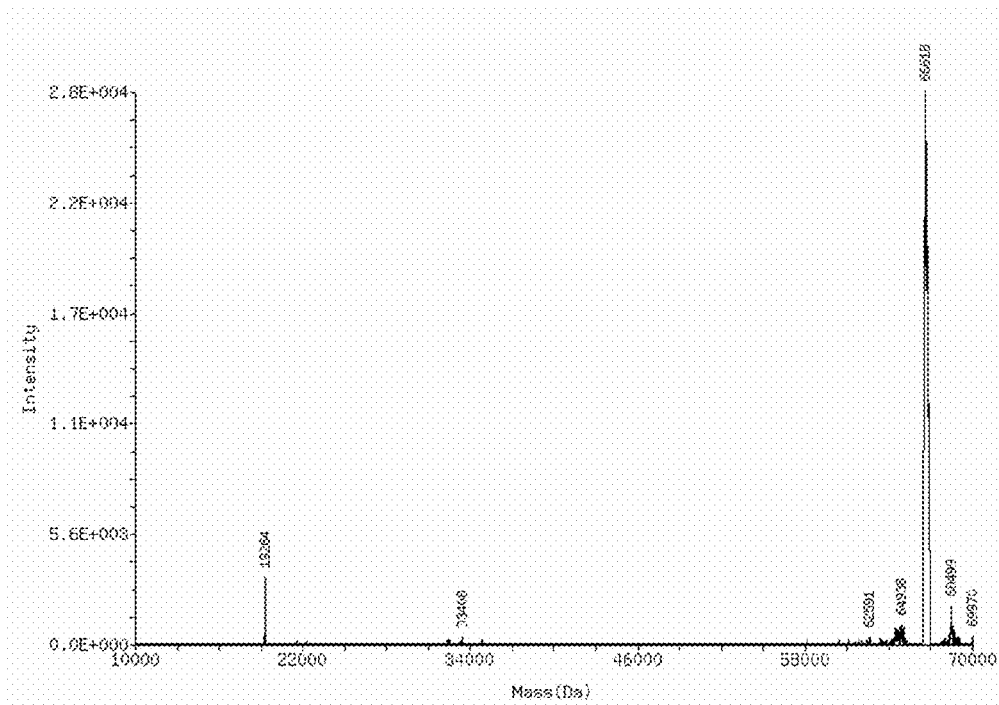
FIG. 12 illustrates an ESI-MS analysis of peptide content in REP 2057 calcium chelate/interferon α-2b composition from the HPLC peak at 11.43 min in FIG. 11. The observed mass peak at 19264 Da corresponds to interferon α-2b (expected m. wt.=19271 Da) and the peak at 66618 Da corresponds to human albumin.
Figure 13:
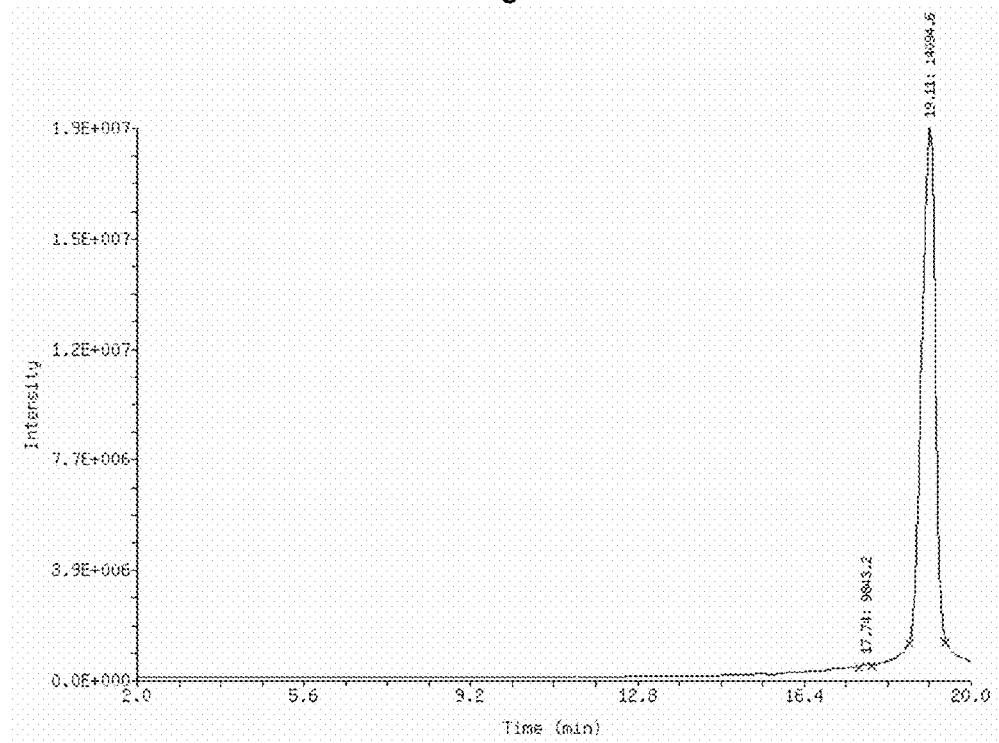
FIG. 13 illustrates a HPLC separation of the REP 2139 calcium chelate/interferon α-2b composition using the oligo method described herein (see Example IV). No incomplete synthesis products are seen.
Figure 14:
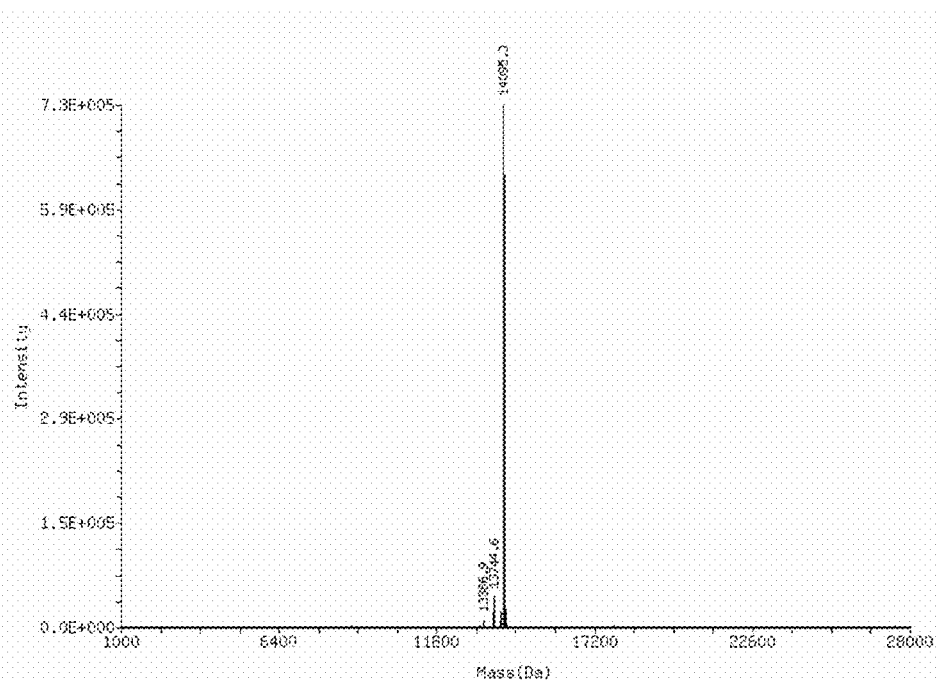
FIG. 14 illustrates an ESI-MS analysis of oligonucleotide content in REP 2139 calcium chelate/interferon α-2b composition from the HPLC peak at 19.11 in FIG. 13. The observed mass of the primary species is 14095.3 Da, identifying it as REP 2139 (expected m. wt.=14094.6).
Figure 15:
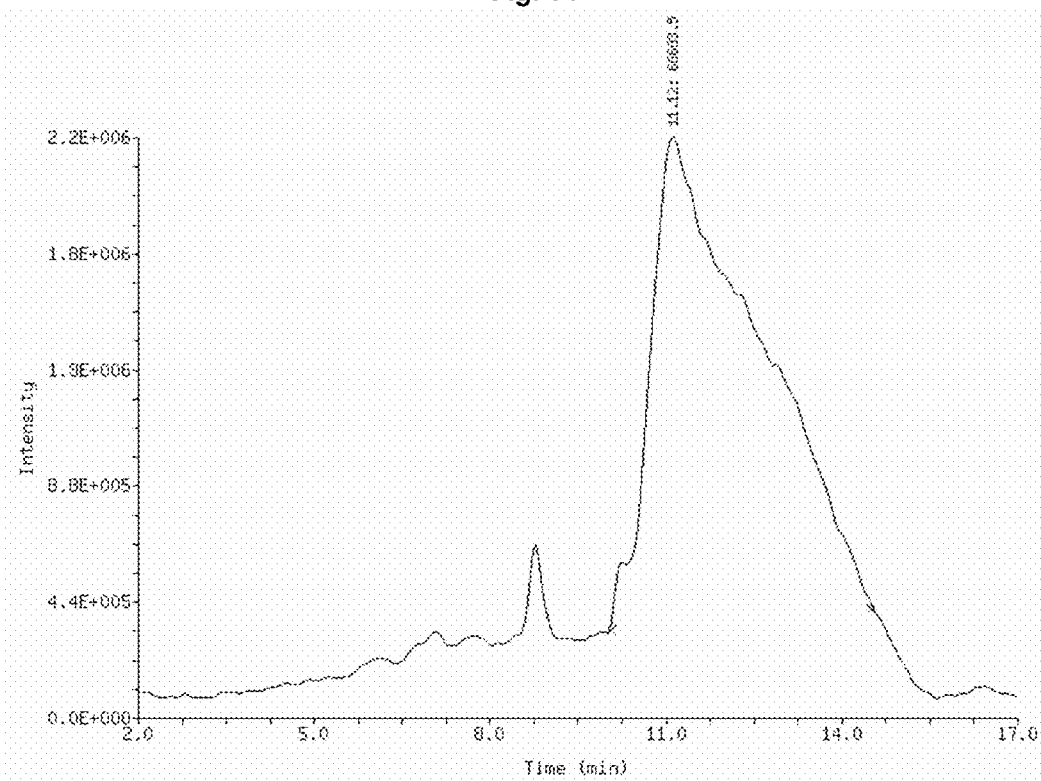
FIG. 15 illustrates a HPLC separation of the REP 2139 calcium chelate/interferon α-2b composition using protein method 1 described herein (see Example IV).
Figure 16:
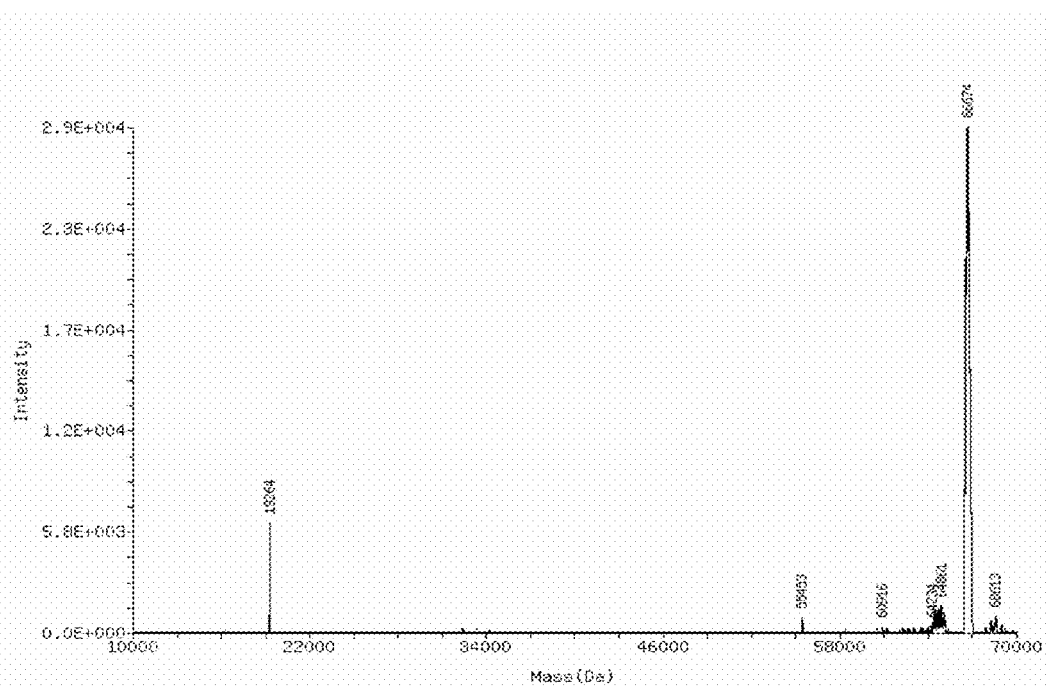
FIG. 16 illustrates an ESI-MS analysis of peptide content in REP 2139 calcium chelate/interferon α-2b composition from the HPLC peak at 11.12 min in FIG. 15. The observed mass peak at 19264 Da corresponds to interferon α-2b (expected m. wt.=19271 Da) and the peak at 66674 Da corresponds to human albumin.
Figure 17:
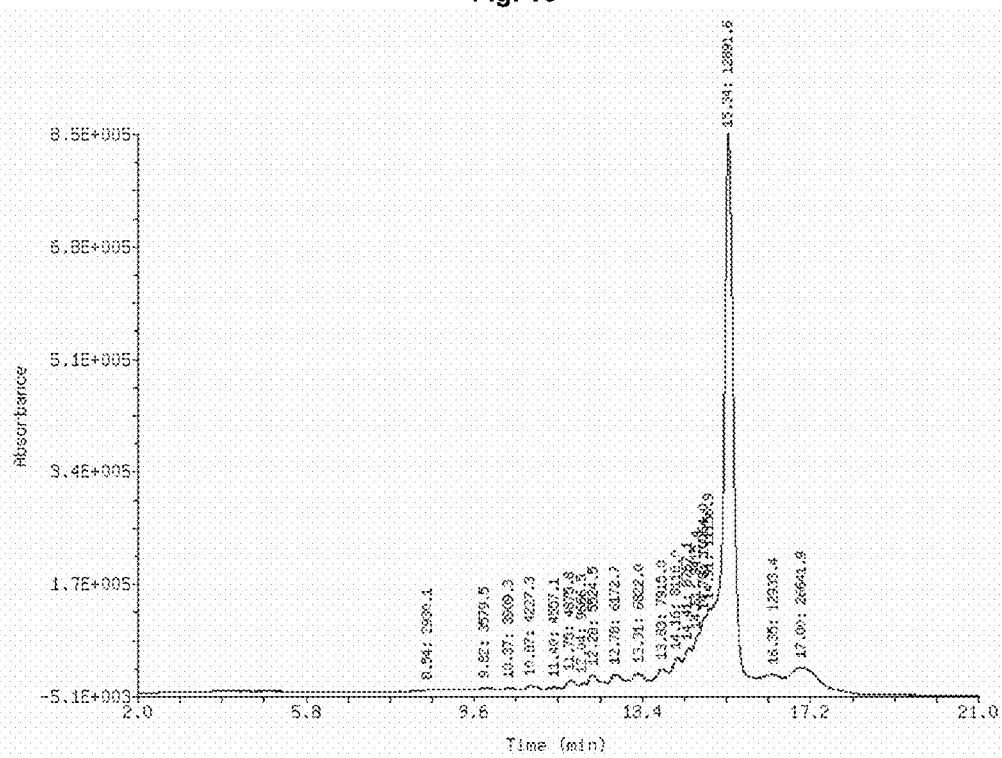
FIG. 17 illustrates a HPLC separation of the REP 2148 calcium chelate/interferon α-2b composition using the oligo method described herein (see Example IV). Minor products of incomplete synthesis precede the main peak of the full length REP 2148 sequence.
Figure 18:
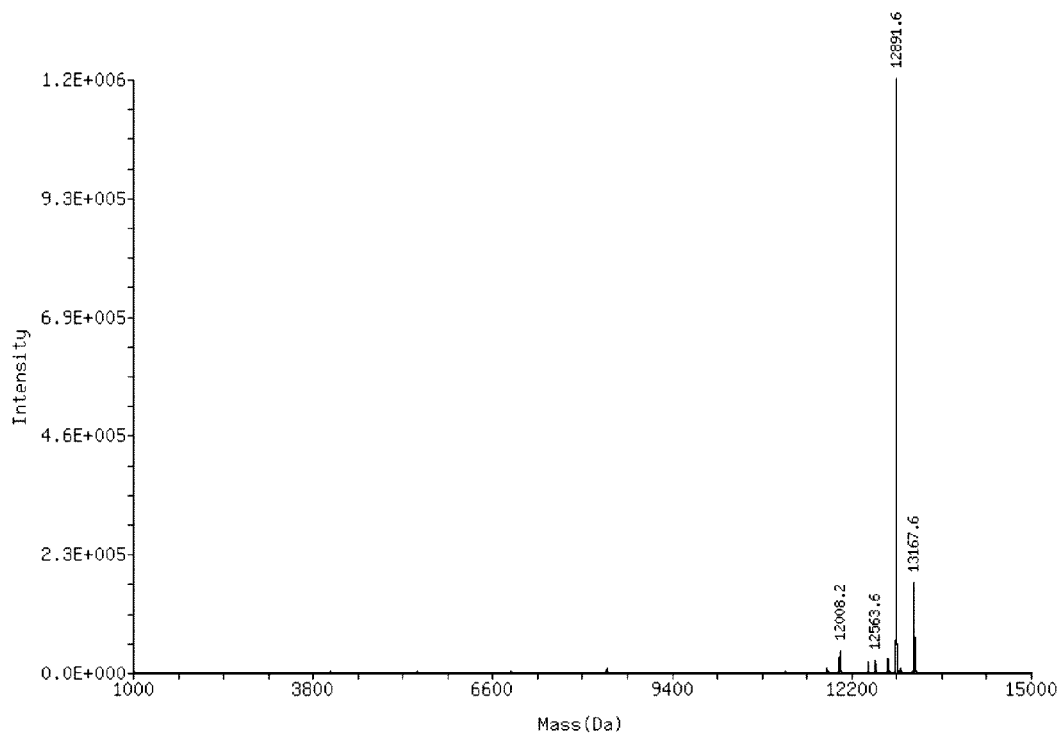
FIG. 18 illustrates an ESI-MS analysis of oligonucleotide content in REP 2148 calcium chelate/interferon α-2b composition from the HPLC peak at 15.34 min in FIG. 17. The observed mass of the primary species is 12891.6 Da, identifying it as REP 2148 (expected m.wt.=12893.6).
Figure 19:
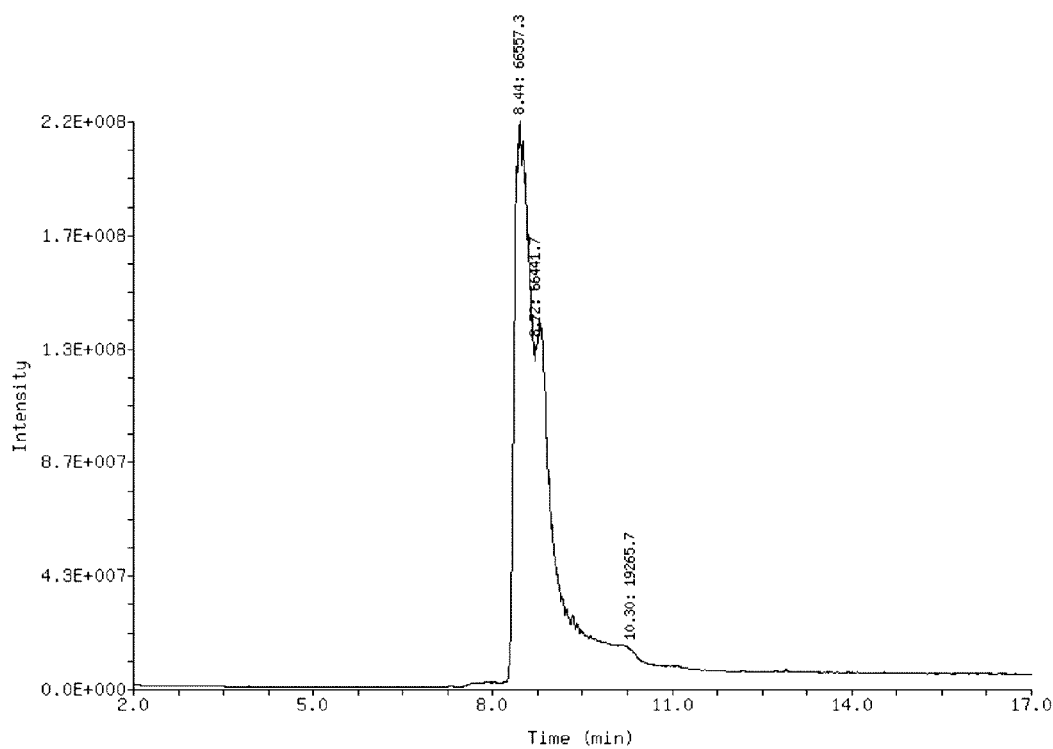
FIG. 19 illustrates an HPLC separation of the REP 2148 calcium chelate/interferon α-2b composition using protein method 1 described herein (see Example IV).
Figure 20:
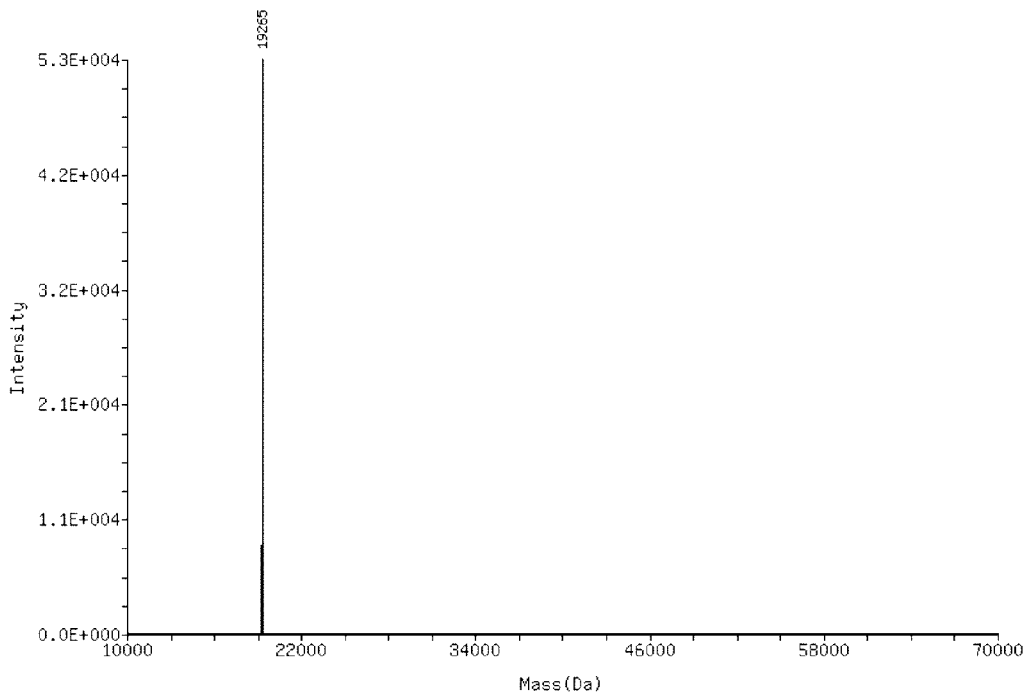
FIG. 20 illustrates an ESI-MS analysis of peptide content in REP 2148 calcium chelate/interferon α-2b composition from the HPLC peak at 8.44 min in FIG. 19. The observed mass peak at 19265 Da corresponds to interferon α-2b.
Figure 21:
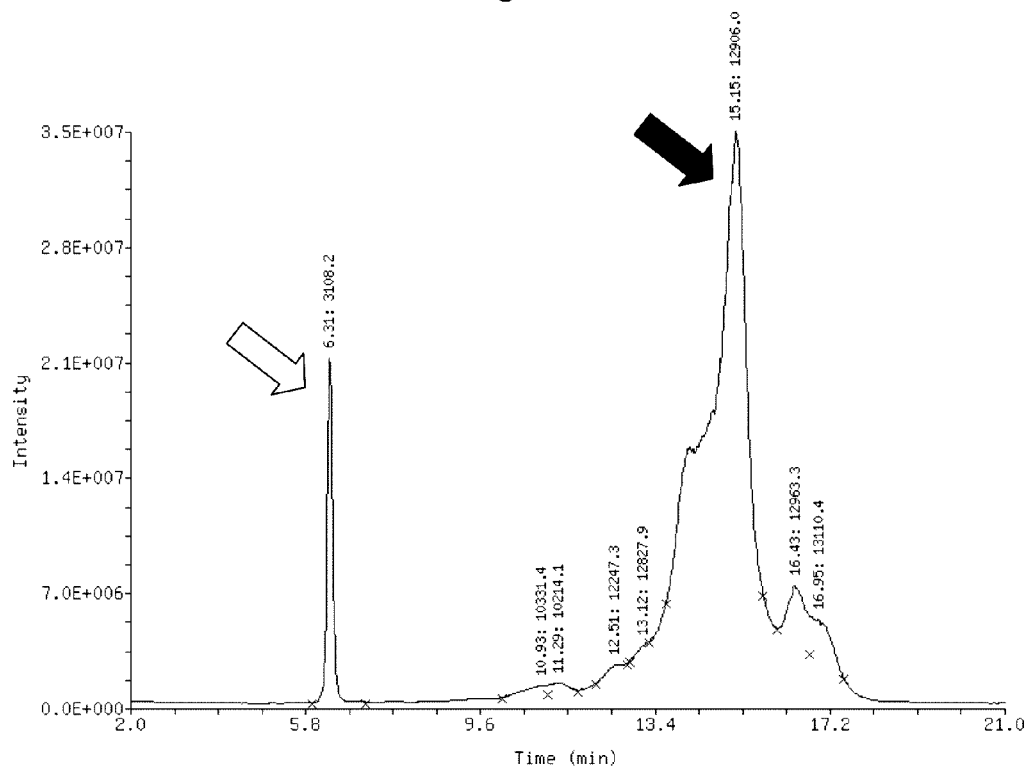
FIG. 21 illustrates a HPLC separation of the REP 2006 calcium chelate/thymosin α1 composition using the oligo method described herein (see Example IV). The peak eluting at 6.31 min corresponds to thymosin α1 (white arrow) and the peak eluting at 15.15 min corresponds to the full length REP 2006 (black arrow).
Figure 22:
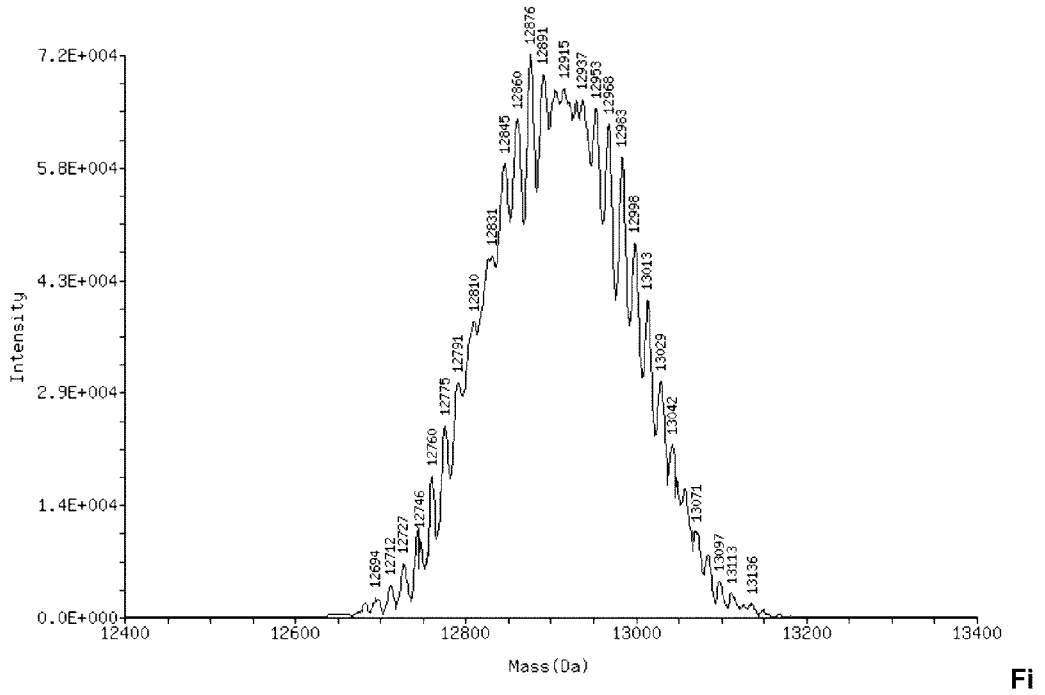
FIG. 22 illustrates an ESI-MS analysis of oligonucleotide content in REP 2006 calcium chelate/thymosin α1 composition from the HPLC peak at 15.15 min in FIG. 21. The observed mass is ~12650-13150 Da, identifying it as REP 2006 (expected m. wt.=12612-1309 2 Da).
Figure 23:
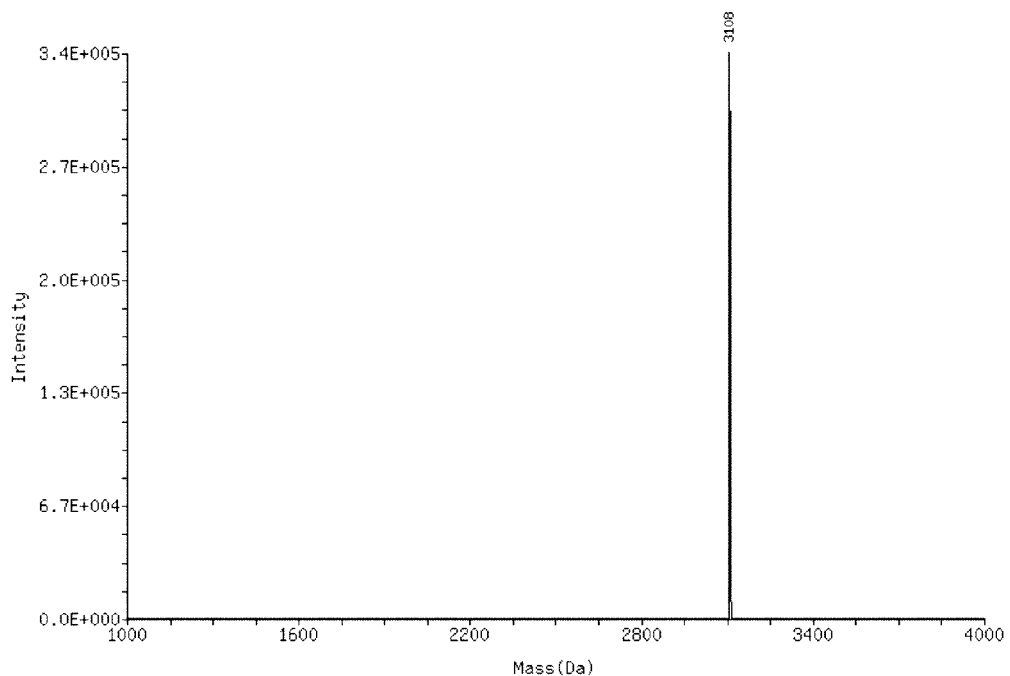
FIG. 23 illustrates an ESI-MS analysis of peptide content in REP 2006 calcium chelate/thymosin α1 composition from the HPLC peak at 6.31 min in FIG. 21. The observed mass of the primary species is 3108 Da, identifying it as thymosin α1 (expected m.wt.=3108 Da).
Figure 24:
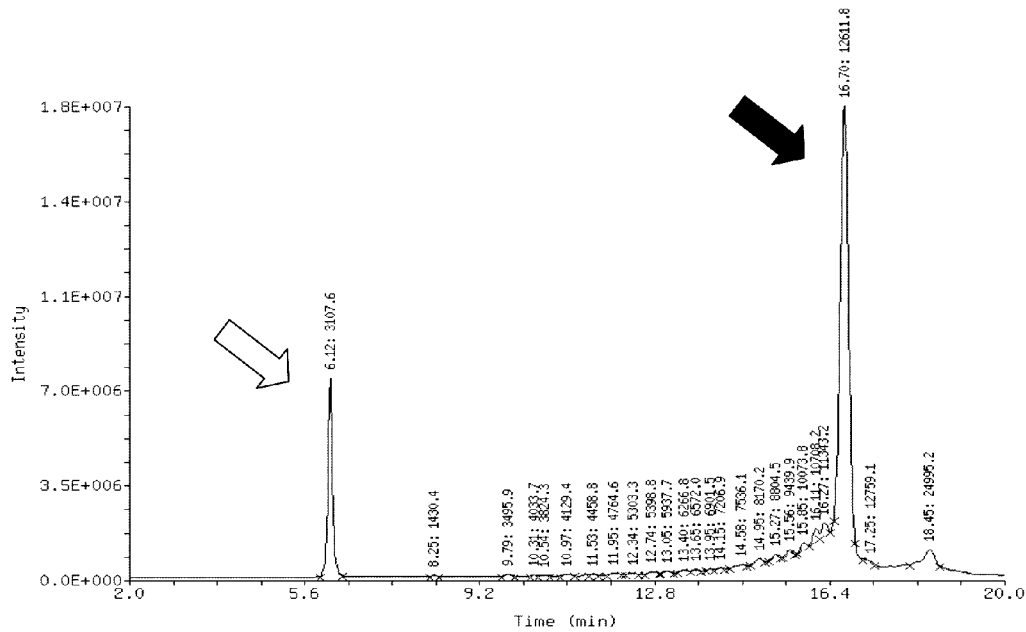
FIG. 24 illustrates a HPLC separation of the REP 2055 calcium chelate/thymosin α1 composition using the oligo method described herein (see Example IV). The peak eluting at 6.12 min corresponds to thymosin α1 (white arrow) and the peak eluting at 16.70 min corresponds to the full length REP 2055 (black arrow).
Figure 25:
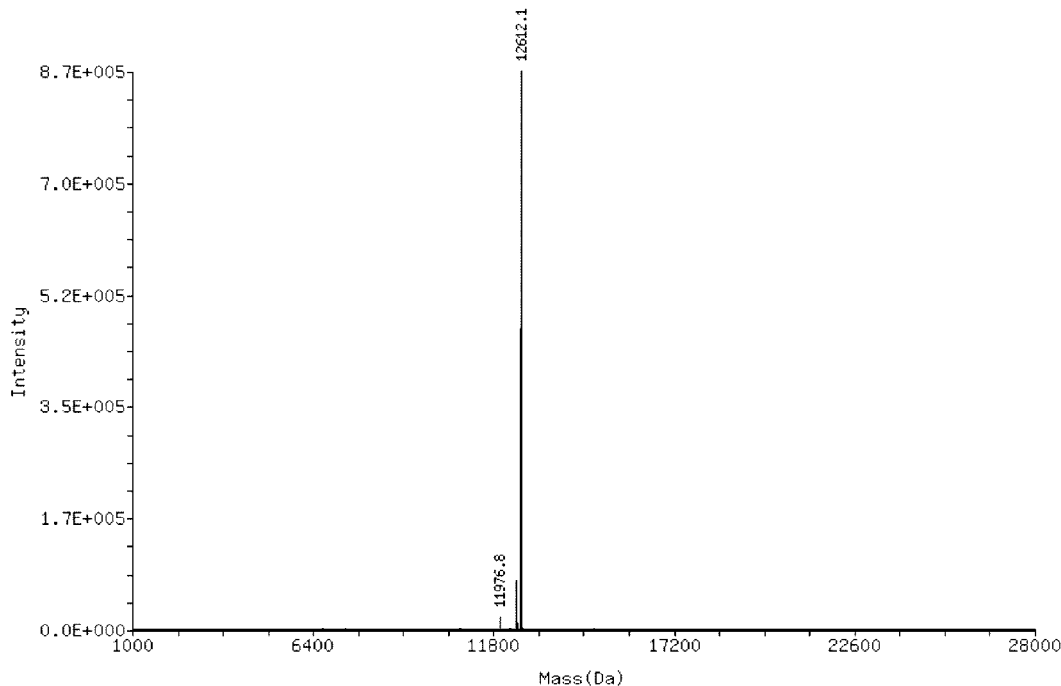
FIG. 25 illustrates an ESI-MS analysis of oligonucleotide content in REP 2055 calcium chelate/thymosin α1 composition from the HPLC peak at 16.70 min in FIG. 24. The observed mass of the primary species is 12612.1 Da, identifying it as REP 2055 (expected m. wt.=12612.5).
Figure 26:
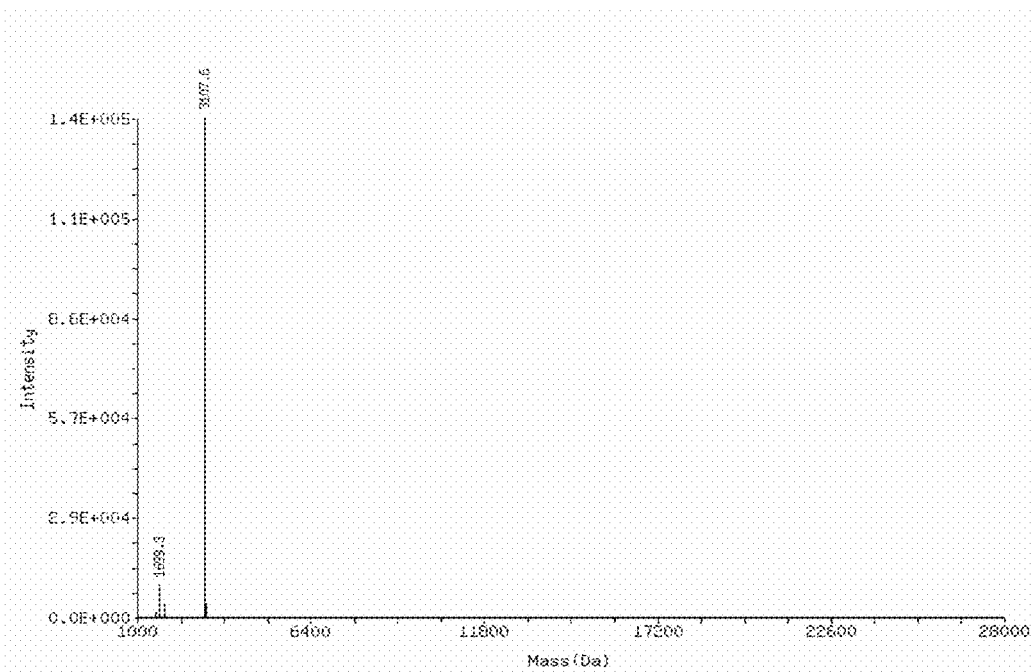
FIG. 26 illustrates an ESI-MS analysis of peptide content in REP 2055 calcium chelate/thymosin α1 composition from the HPLC peak at 6.12 min in FIG. 24. The observed mass of the primary species is 3107.6 Da, identifying it as thymosin α1 (expected m.wt.=3108 Da).
Figure 27:
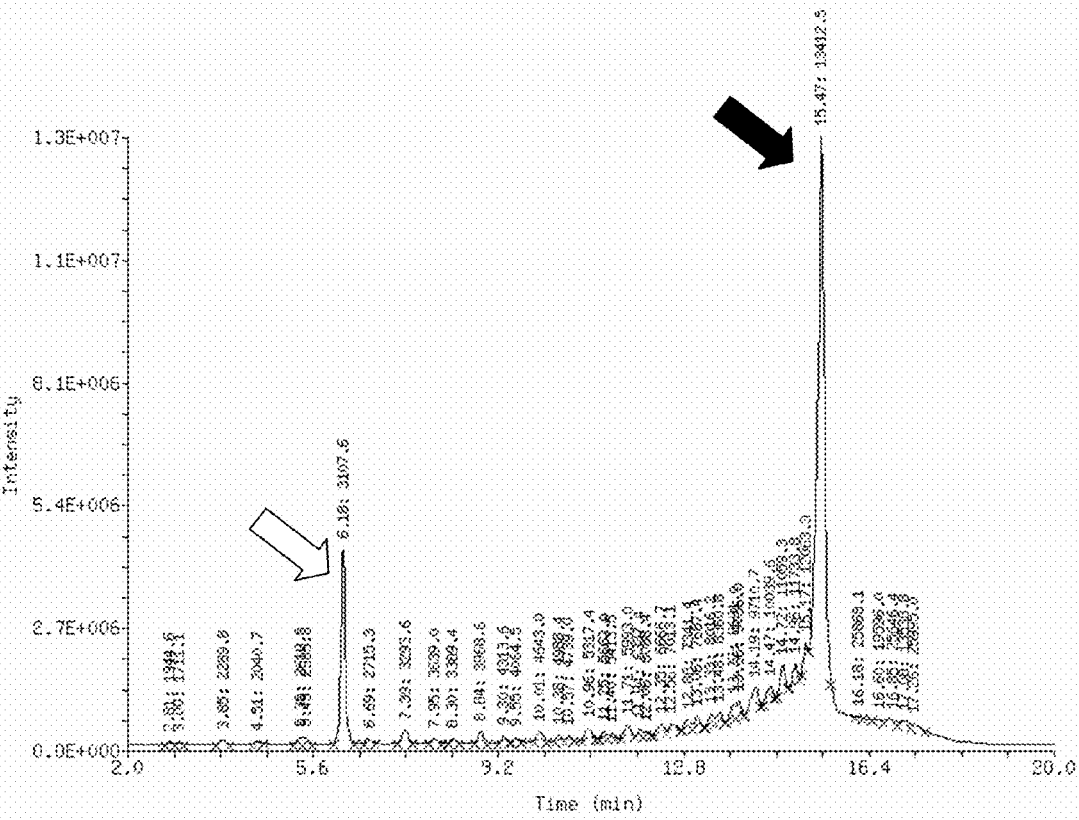
FIG. 27 illustrates a HPLC separation of the REP 2057 calcium chelate/thymosin α1 composition using the oligo method described herein (see Example IV). The peak eluting at 6.18 min corresponds to thymosin α1 (white arrow) and the peak eluting at 15.47 min corresponds to the full length REP 2057 (black arrow).
Figure 28:
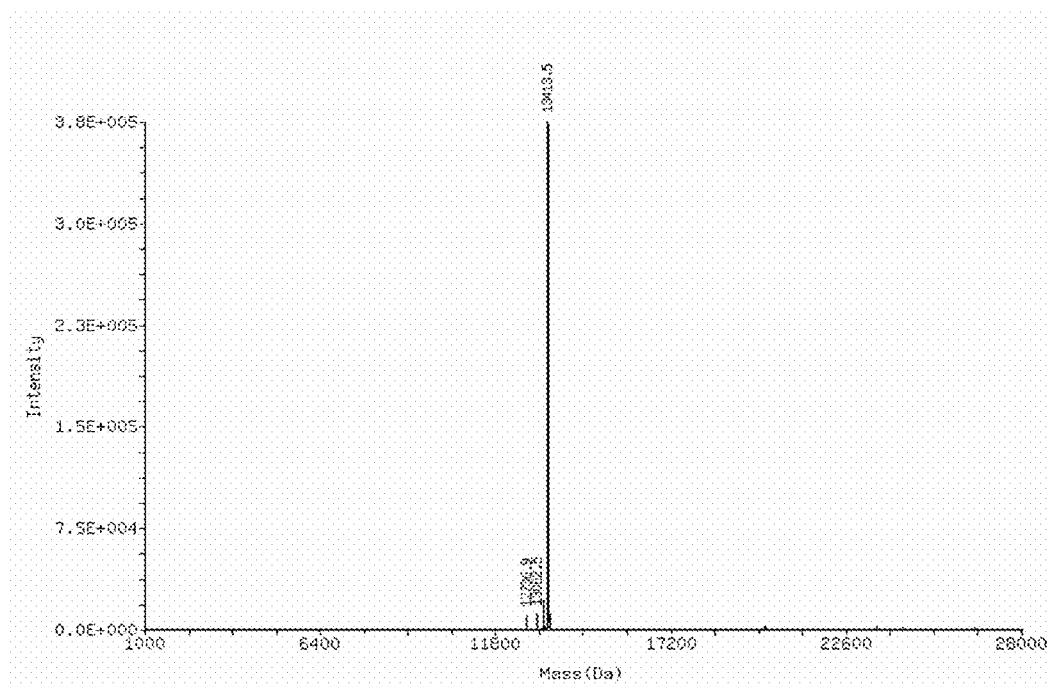
FIG. 28 illustrates an ESI-MS analysis of oligonucleotide content in REP 2057 calcium chelate/thymosin α1 composition from the HPLC peak at 15.47 min in FIG. 27. The observed mass of the primary species is 13413.5 Da, identifying it as REP 2057 (expected m.wt.=13413.3 Da).
Figure 29:
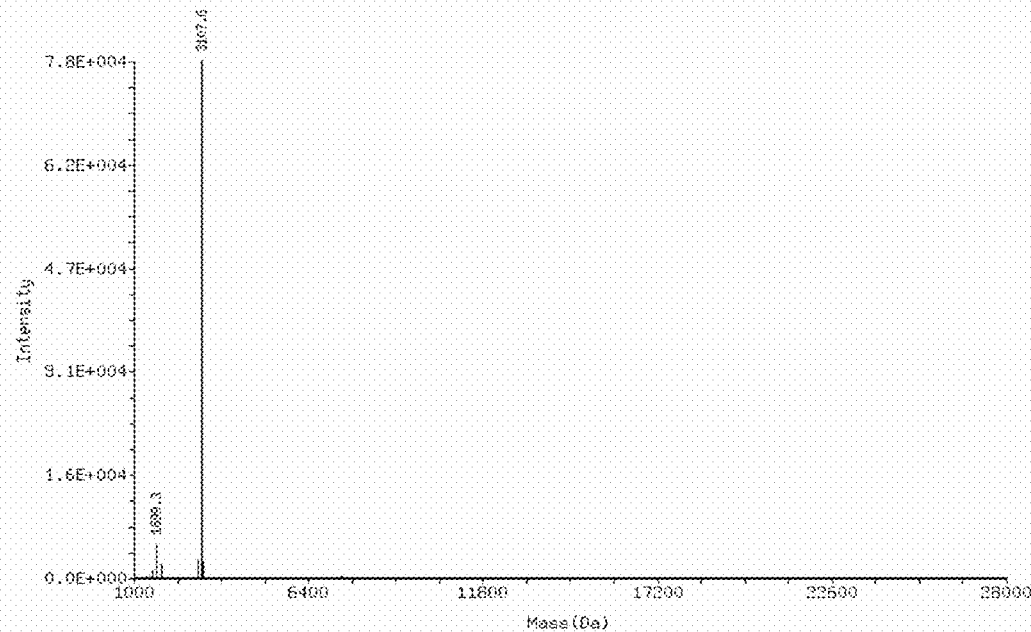
FIG. 29 illustrates an ESI-MS analysis of peptide content in REP 2057 calcium chelate/thymosin α1 composition from the HPLC peak at 6.18 min in FIG. 27. The observed mass of the primary species is 3107.6 Da, identifying it as thymosin α1 (expected m.wt.=3108 Da).
Figure 30:
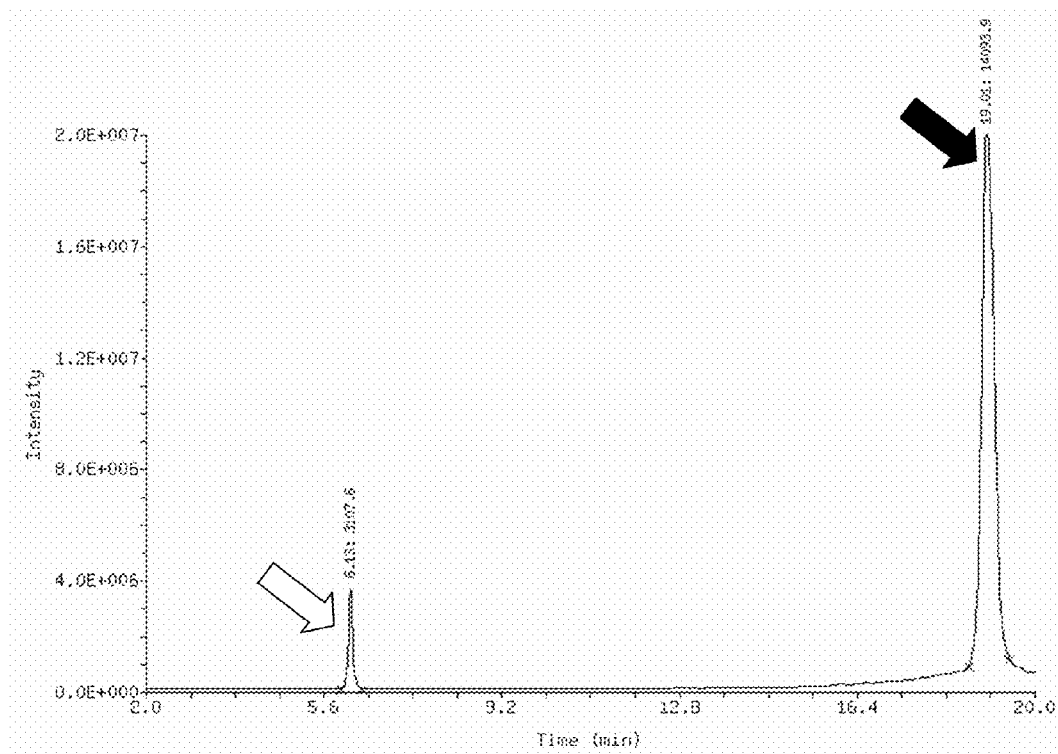
FIG. 30 illustrates a HPLC separation of the REP 2139 calcium chelate/thymosin α1 composition using the oligo method described herein (see Example IV). The peak eluting at 6.13 min corresponds to thymosin α1 (white arrow) and the peak eluting at 19.01 min corresponds to the full length REP 2139 (black arrow).
Figure 31:
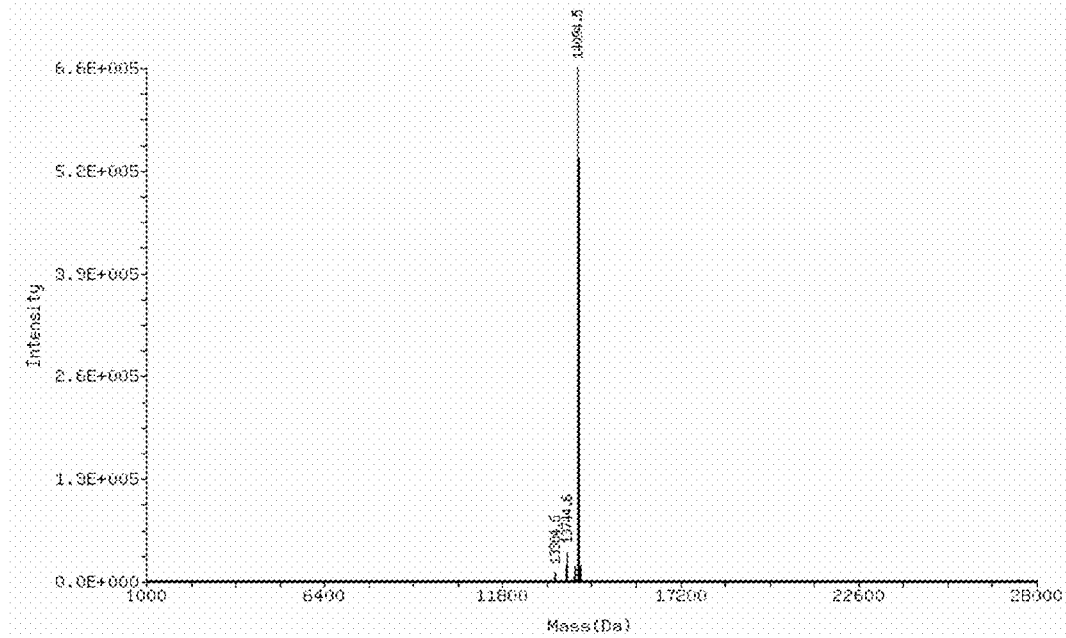
FIG. 31 illustrates an ESI-MS analysis of oligonucleotide content in REP 2139 calcium chelate/thymosin α1 composition from the HPLC peak at 19.01 min in FIG. 30. The observed mass of the primary species is 14094.5 Da, identifying it as REP 2139 (expected m.wt.=14094.6).
Figure 32:
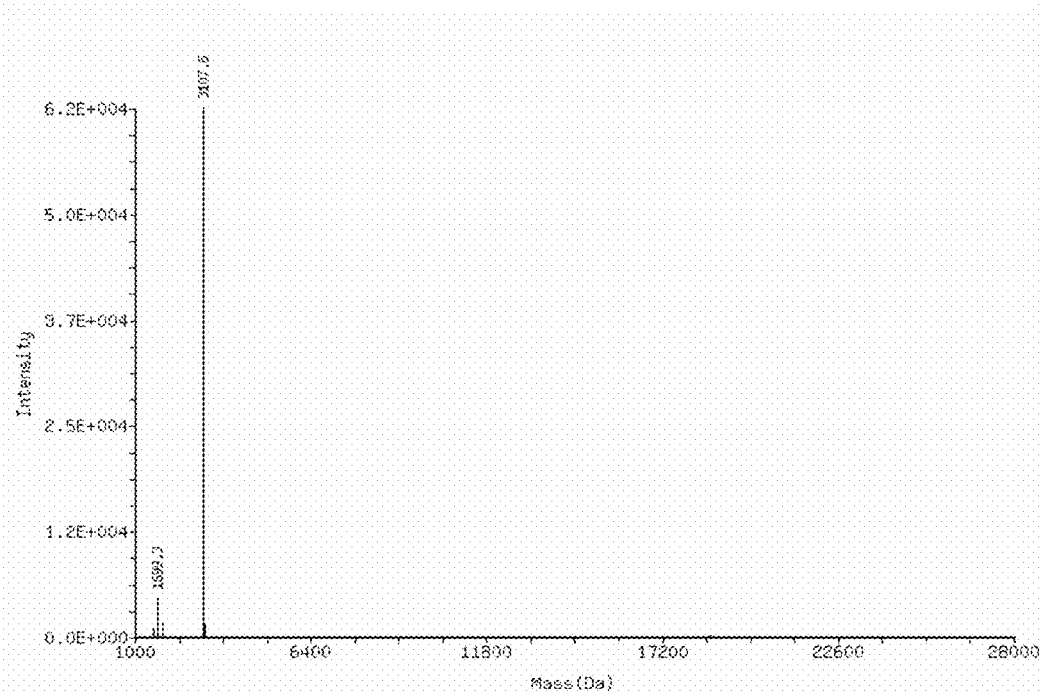
FIG. 32 illustrates an ESI-MS analysis of peptide content in REP 2139 calcium chelate/thymosin α1 composition from the HPLC peak at 6.13 min in FIG. 30. The observed mass of the primary species is 3107.6 Da, identifying it as thymosin α1 (expected m.wt.=3108 Da).
Figure 33:
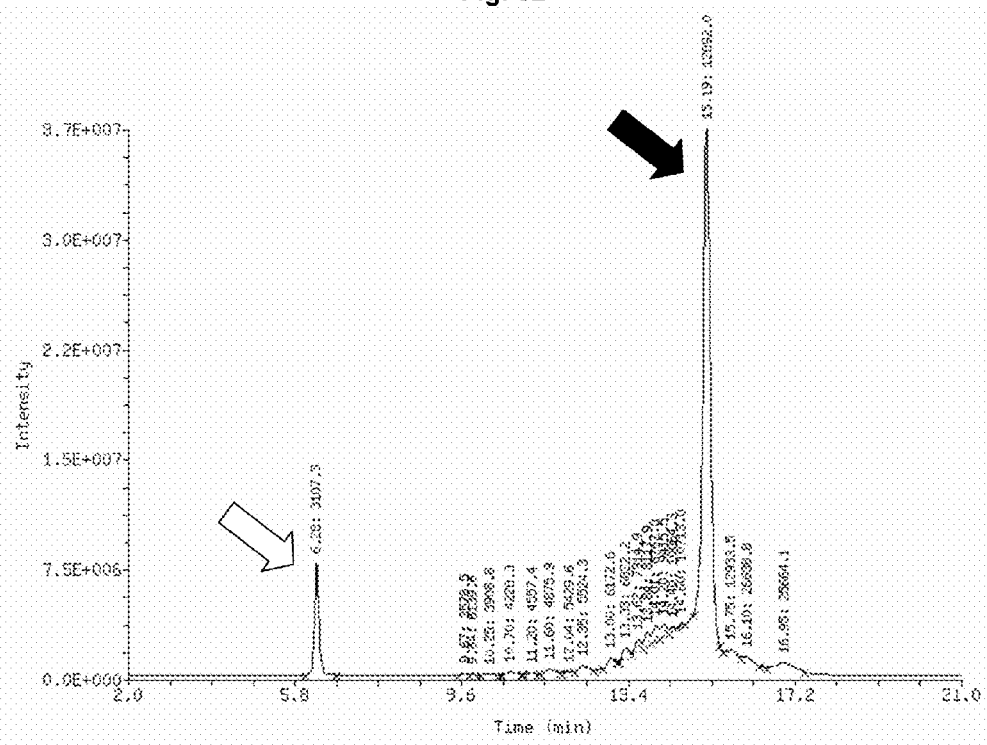
FIG. 33 illustrates a HPLC separation of the REP 2148 calcium chelate/thymosin α1 composition using the oligo method described herein (see Example IV). The peak eluting at 6.28 min corresponds to thymosin α1 (white arrow) and the peak eluting at 15.19 min corresponds to the full length REP 2148 (black arrow).
Figure 34:
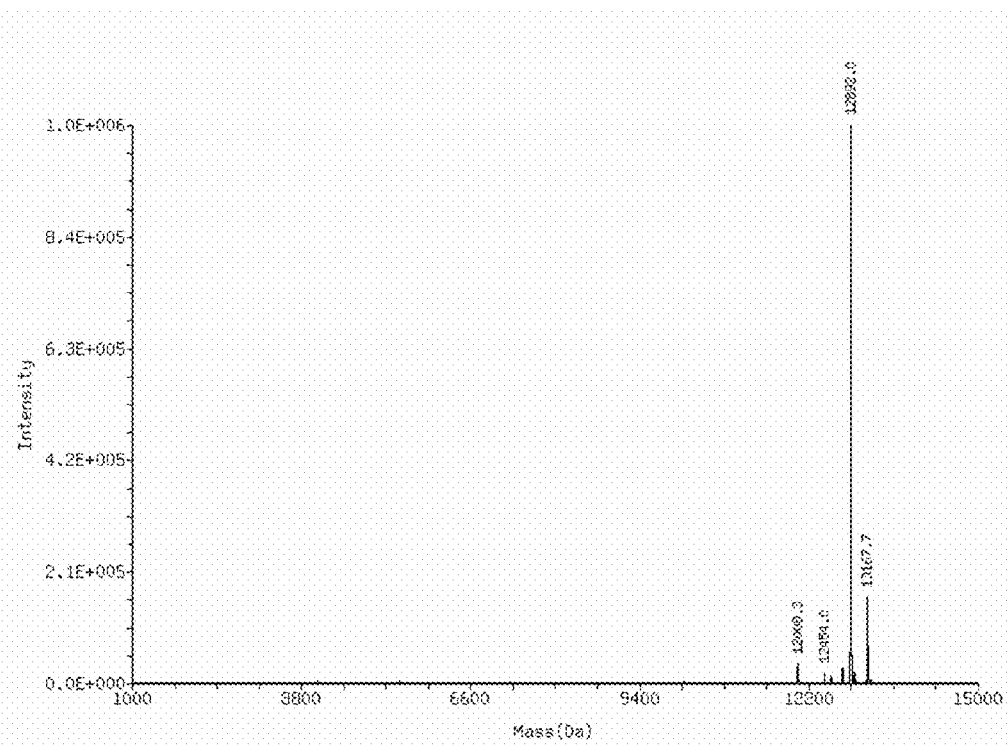
FIG. 34 illustrates an ESI-MS analysis of oligonucleotide content in REP 2148 calcium chelate/thymosin α1 composition from the HPLC peak at 15.19 min in FIG. 33. The observed mass of the primary species is 12892 Da, identifying it as REP 2148 (expected m.wt.=12893 Da).
Figure 35:
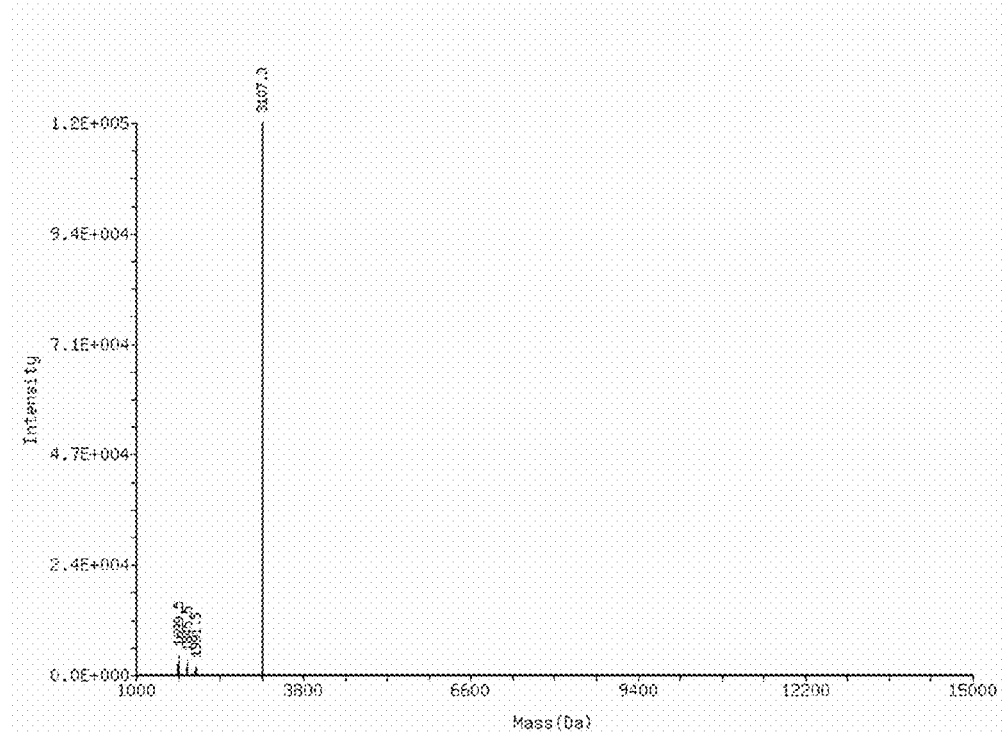
FIG. 35 illustrates an ESI-MS analysis of peptide content in REP 2148 calcium chelate/thymosin α1 composition from the HPLC peak at 6.28 min in FIG. 33. The observed mass of the primary species is 3107.3 Da, identifying it as thymosin α1 (expected m.wt.=3108 Da).
Figure 36:
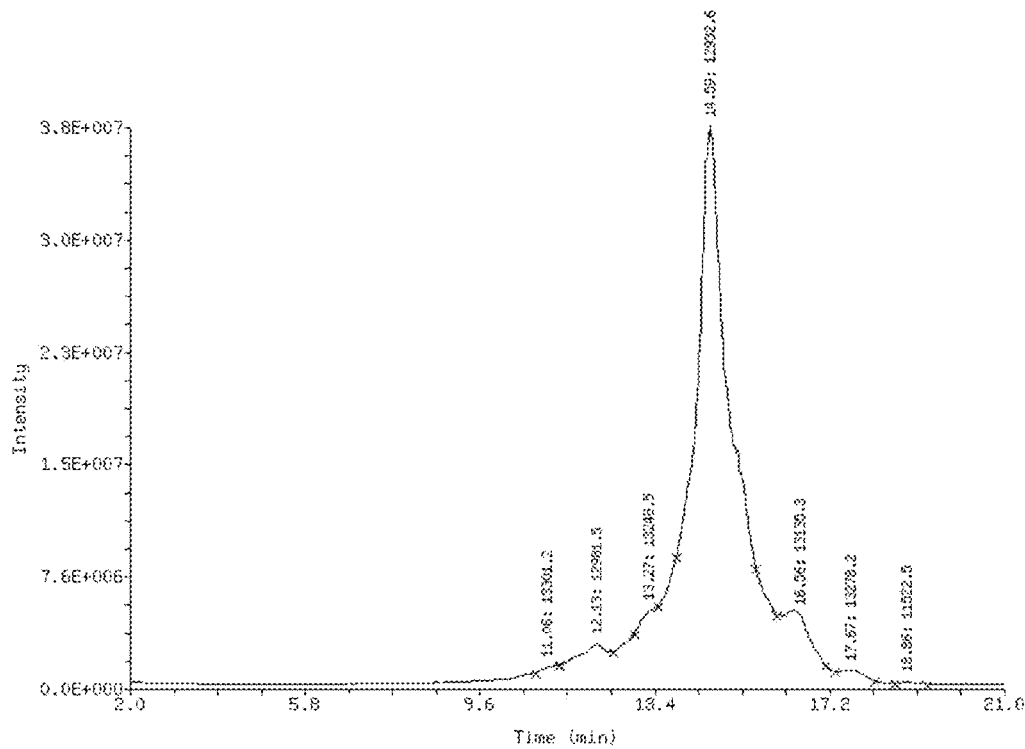
FIG. 36 illustrates a HPLC separation of the REP 2006 calcium chelate/pegylated interferon α-2a composition using the oligo method described herein (see Example IV).
Figure 37:
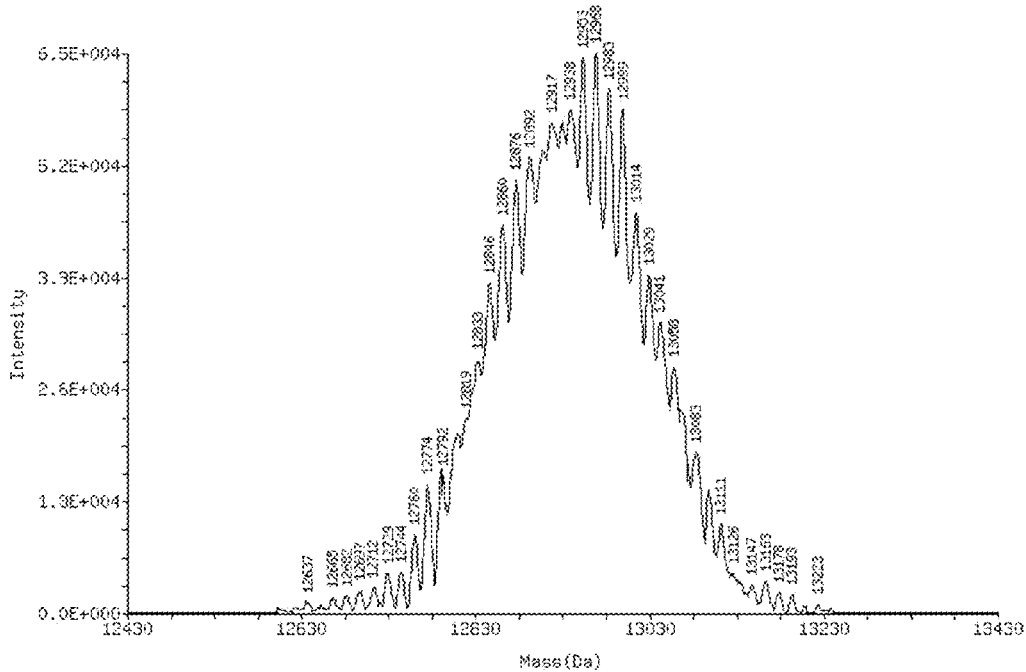
FIG. 37 illustrates an ESI-MS analysis of oligonucleotide content in REP 2006 calcium chelate/pegylated interferon α-2a composition from the HPLC peak at 14.59 min in FIG. 36. The observed mass of the primary species is ~12600-13200 Da, identifying it as REP 2006 (expected m.wt.=12612-13092 Da).
Figure 38:
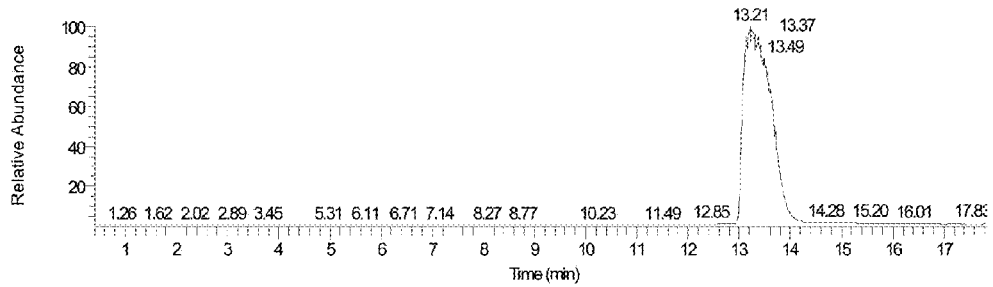
FIG. 38 illustrates a HPLC separation of the REP 2006 calcium chelate/pegylated interferon α-2a composition using protein method 2 described herein (see Example IV).
Figure 39:
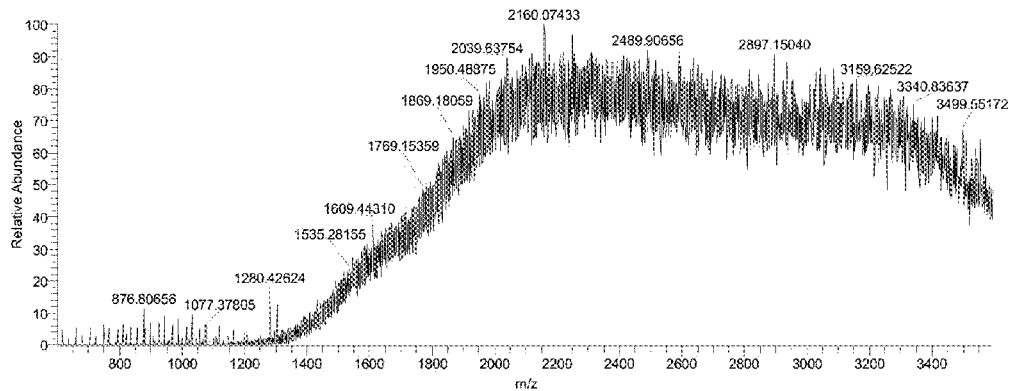
FIG. 39 illustrates an ESI-MS analysis of peptide content in REP 2006 calcium chelate/pegylated interferon α-2a composition from the HPLC peak at 13.21 min in FIG. 38.
Figure 40:
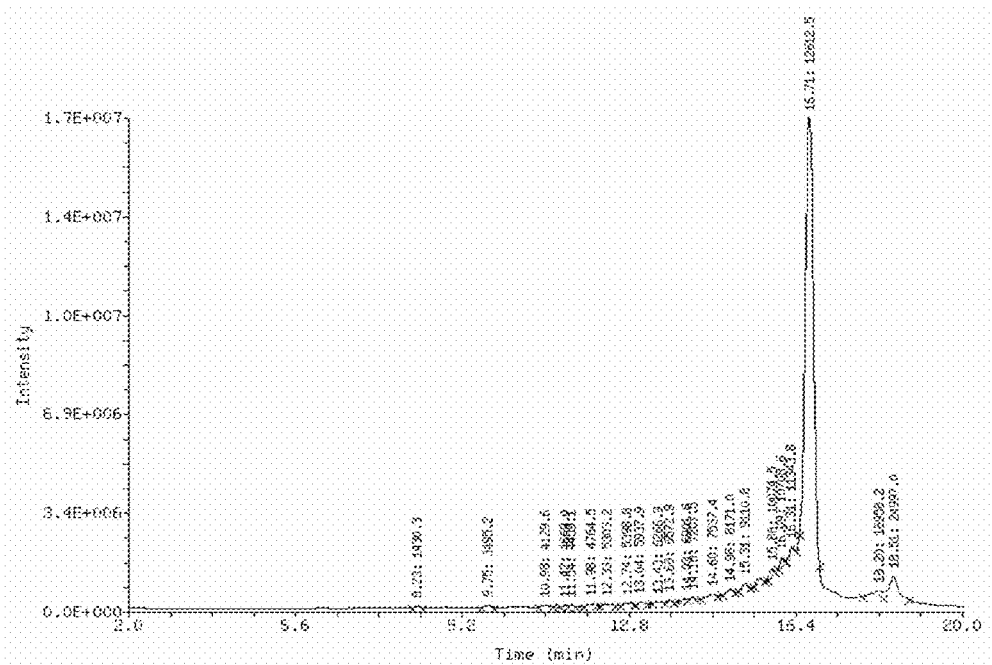
FIG. 40 illustrates a HPLC separation of the REP 2055 calcium chelate/pegylated interferon α-2a composition using the oligo method described herein (see Example IV).
Figure 41:
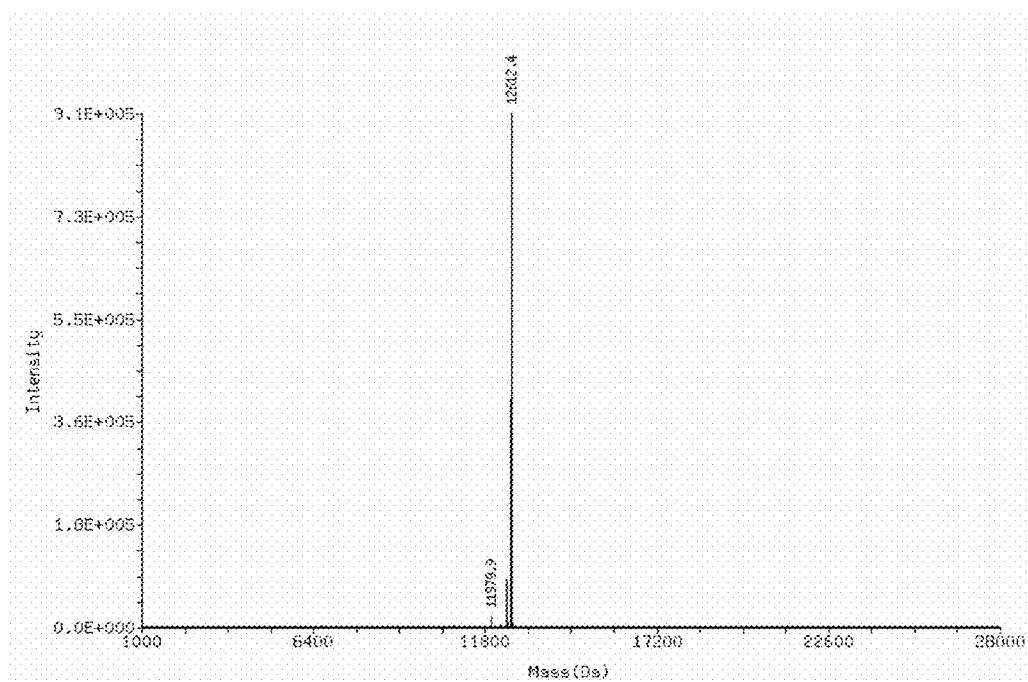
FIG. 41 illustrates an ESI-MS analysis of oligonucleotide content in REP 2055 calcium chelate/pegylated interferon α-2a composition from the HPLC peak at 16.71 min in FIG. 40. The observed mass of the primary species is 12612.4 Da, identifying it as REP 2055 (expected m.wt.=12612.5 Da).
Figure 42:
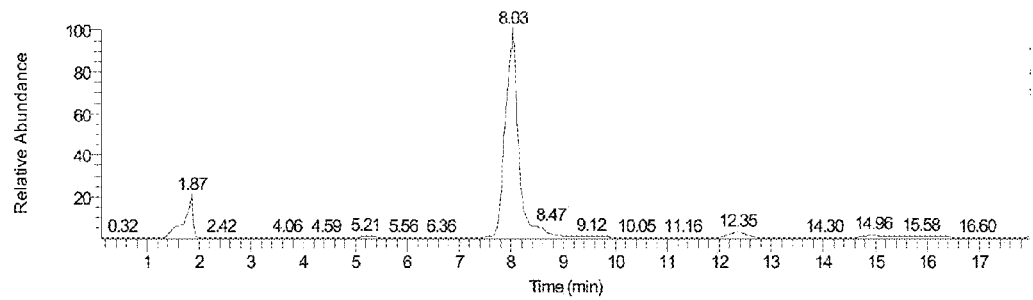
FIG. 42 illustrates a HPLC separation of the REP 2055 calcium chelate/pegylated interferon α-2a composition using protein method 2 described herein (see Example IV).
Figure 43:
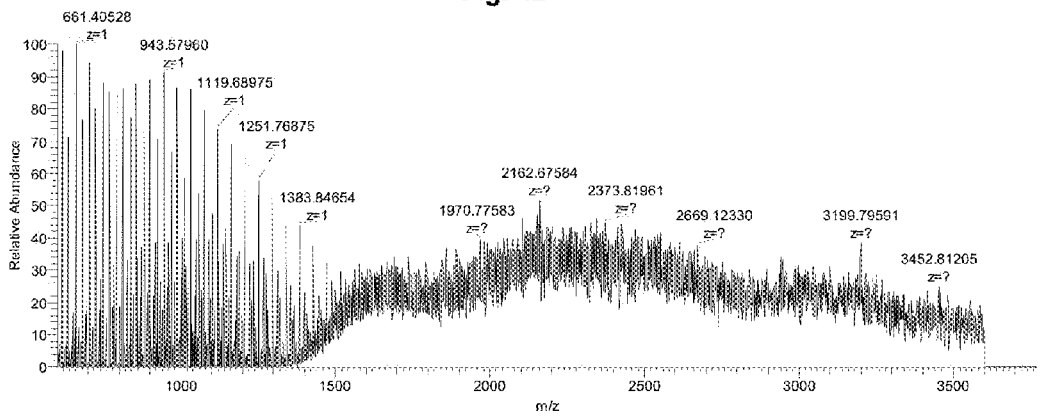
FIG. 43 illustrates an ESI-MS analysis of peptide content in REP 2055 calcium chelate/pegylated interferon α-2a composition from the HPLC peak at 8.03 min in FIG. 42.
Figure 44:
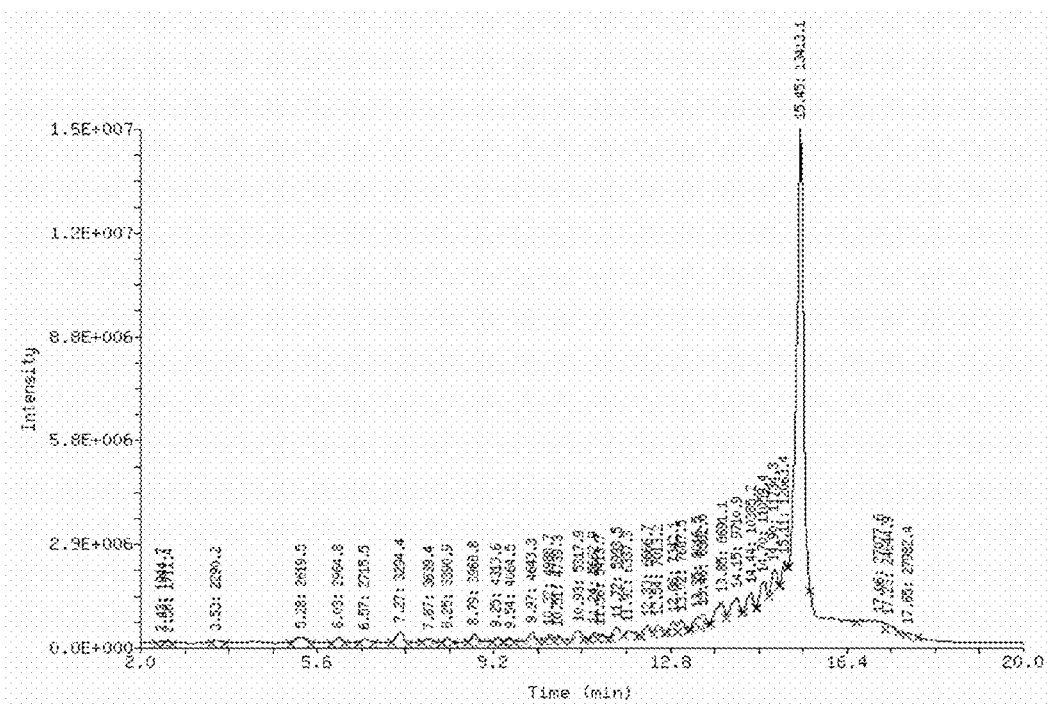
FIG. 44 illustrates a HPLC separation of the REP 2057 calcium chelate/pegylated interferon α-2a composition using the oligo method described herein (see Example IV).
Figure 45:
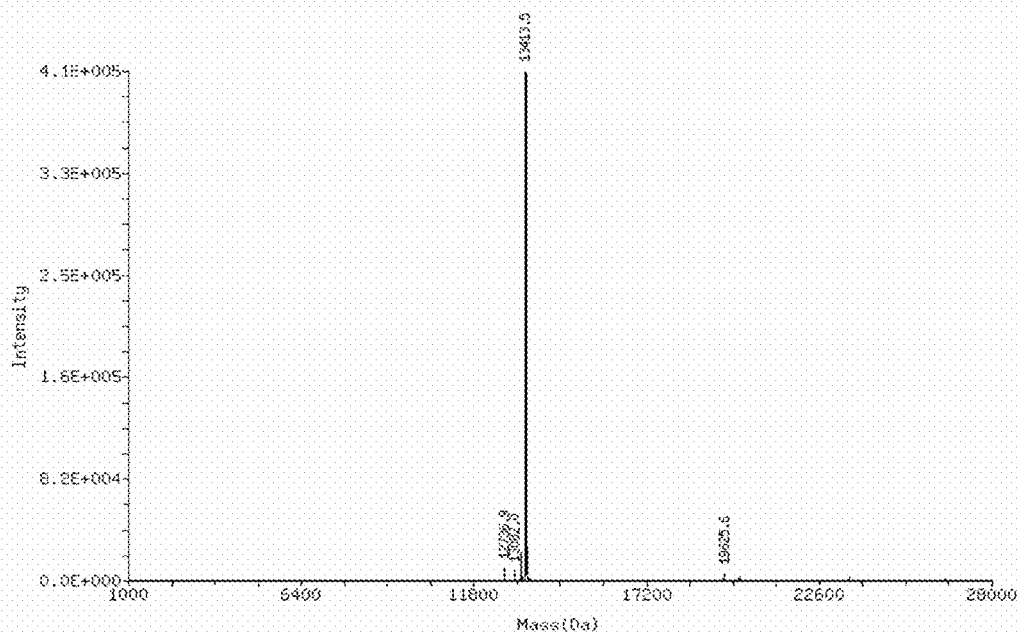
FIG. 45 illustrates an ESI-MS analysis of oligonucleotide content in REP 2057 calcium chelate/pegylated interferon α-2a composition from the HPLC peak at 15.45 min in FIG. 44. The observed mass of the primary species is 13413.5 Da, identifying it as REP 2057 (expected m.wt.=13413.3 Da).
Figure 46:
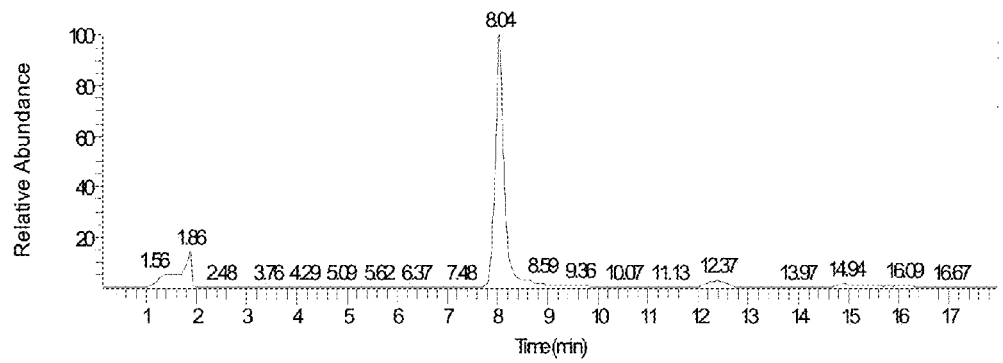
FIG. 46 illustrates a HPLC separation of the REP 2057 calcium chelate/pegylated interferon α-2a composition using protein method 2 described herein (see Example IV).
Figure 47:
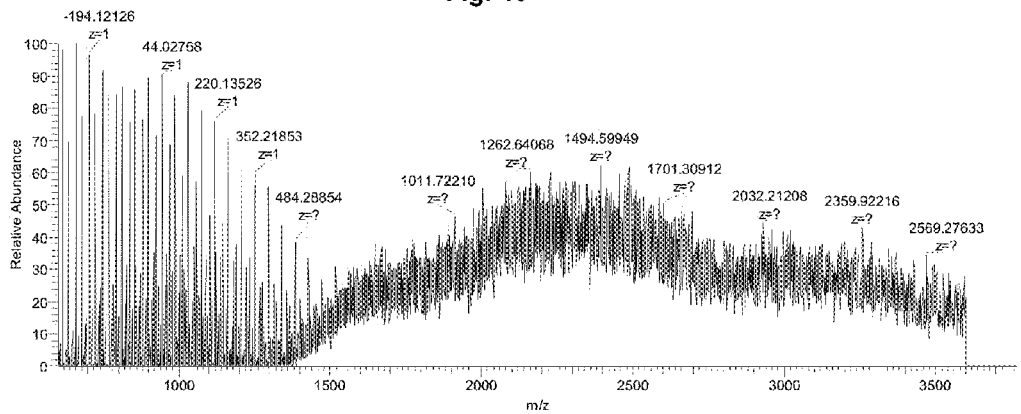
FIG. 47 illustrates an ESI-MS analysis of peptide content in REP 2057 calcium chelate/pegylated interferon α-2a composition from the HPLC peak at 8.04 min in FIG. 46.
Figure 48:
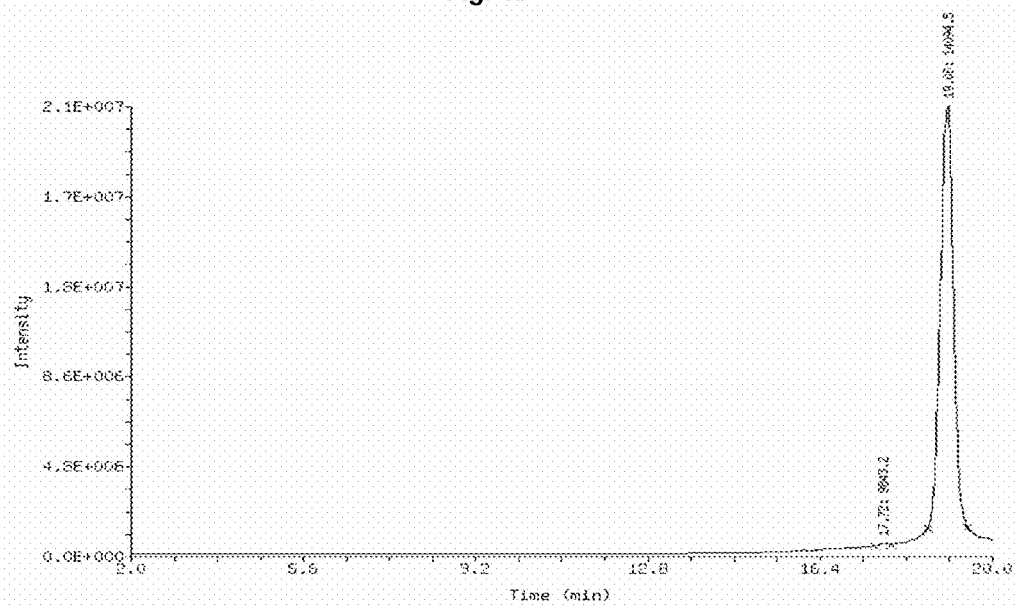
FIG. 48 illustrates a HPLC separation of the REP 2139 calcium chelate/pegylated interferon α-2a composition using the oligo method described herein (see Example IV).
Figure 49:
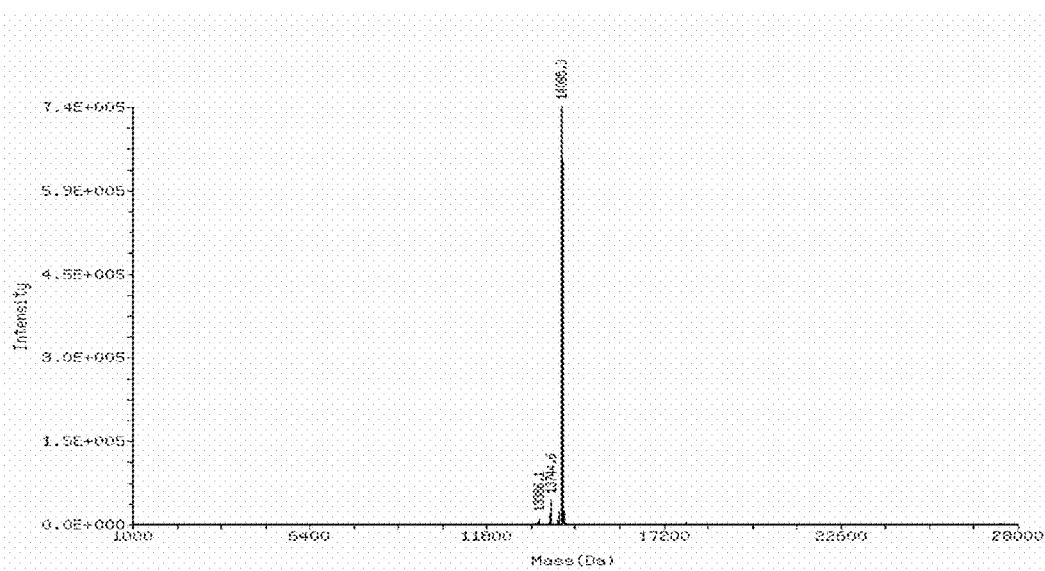
FIG. 49 illustrates an ESI-MS analysis of oligonucleotide content in REP 2139 calcium chelate/pegylated interferon α-2a composition from the HPLC peak at 19.08 min in FIG. 48. The observed mass of the primary species is 14095.3 Da, identifying it as REP 2139 (expected m.wt.=14094.6 Da).
Figure 50:
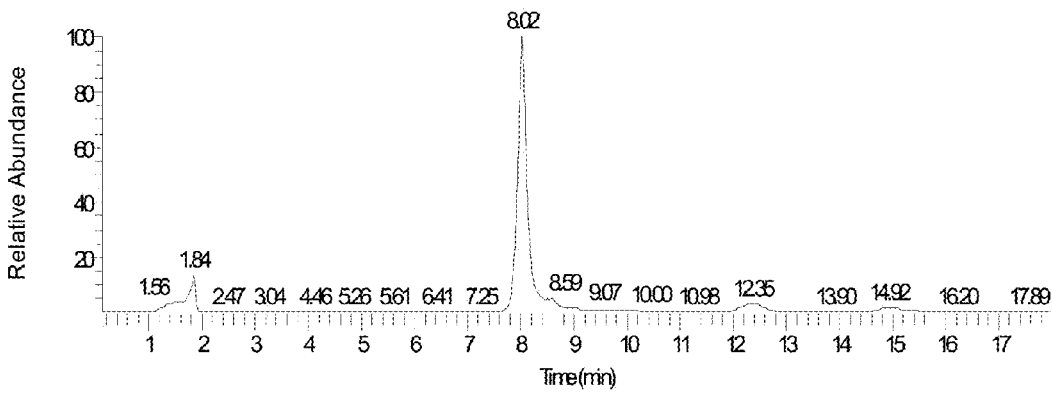
FIG. 50 illustrates a HPLC separation of the REP 2139 calcium chelate/pegylated interferon α-2a composition using protein method 2 described herein (see Example IV).
Figure 51:
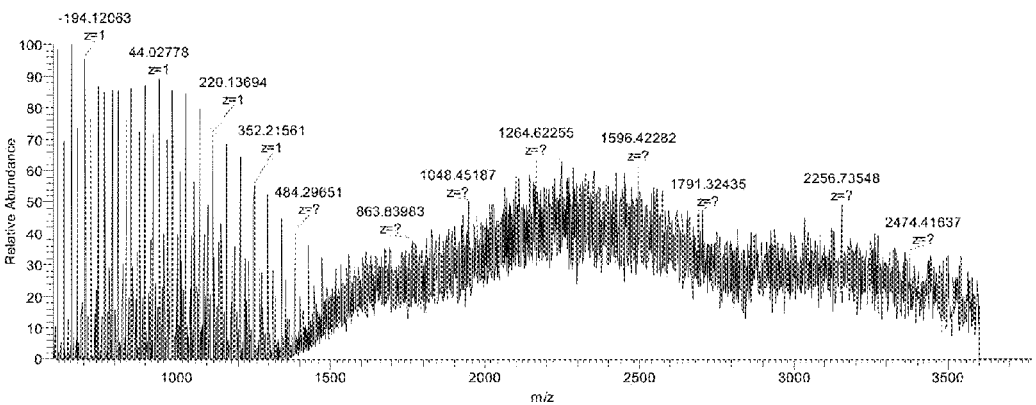
FIG. 51 illustrates an ESI-MS analysis of peptide content in REP 2139 calcium chelate/pegylated interferon α-2a composition from the HPLC peak at 8.02 min in FIG. 50.
Figure 52:
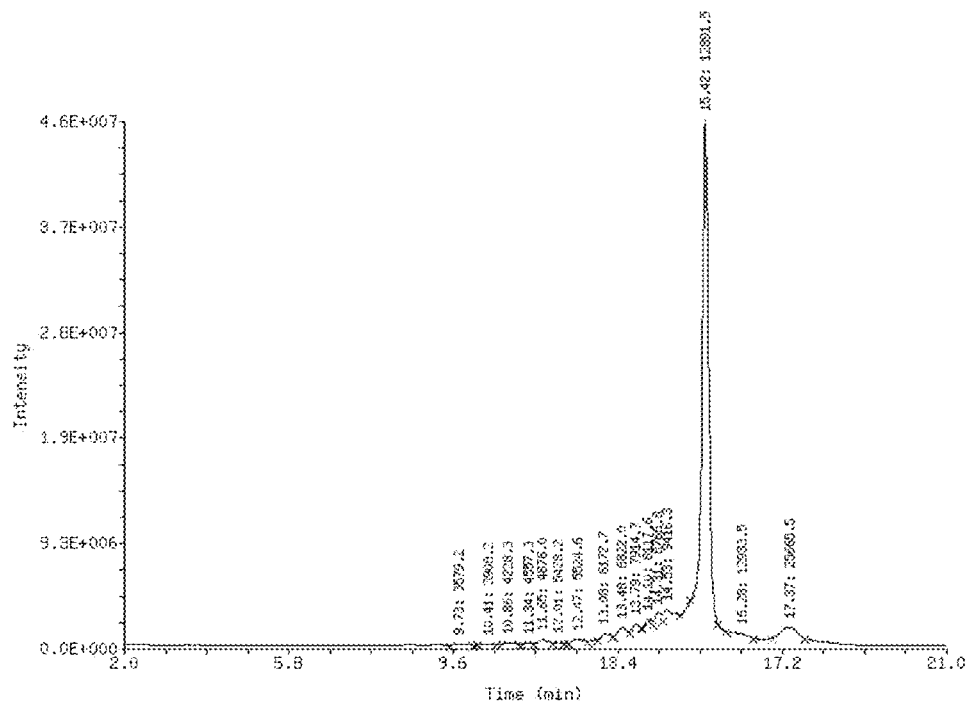
FIG. 52 illustrates a HPLC separation of the REP 2148 calcium chelate/pegylated interferon α-2a composition using the oligo method described herein (see Example IV).
Figure 53:
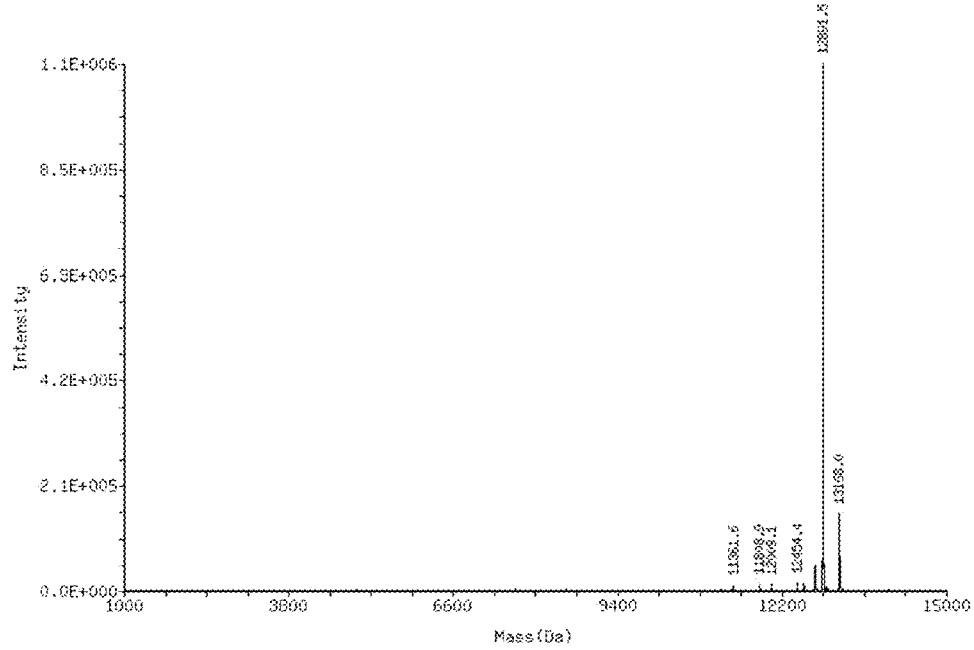
FIG. 53 illustrates an ESI-MS analysis of oligonucleotide content in REP 2148 calcium chelate/pegylated interferon α-2a composition from the HPLC peak at 15.42 min in FIG. 52. The observed mass of the primary species is 12891.5 Da, identifying it as REP 2148 (expected m.wt.=12893 Da).
Figure 54:
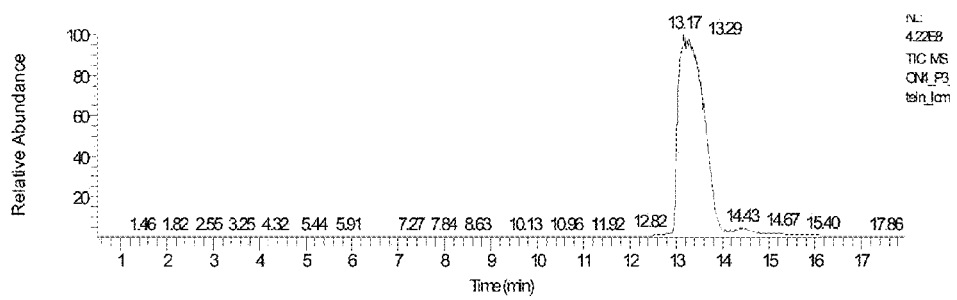
FIG. 54 illustrates a HPLC separation of the REP 2148 calcium chelate/pegylated interferon α-2a composition using protein method 2 described herein (see Example IV).
Figure 55:
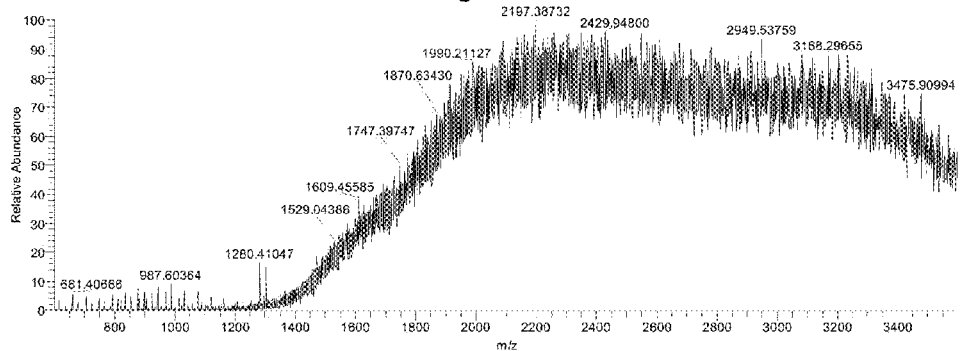
FIG. 55 illustrates an ESI-MS analysis of peptide content in REP 2148 calcium chelate/pegylated interferon α-2a composition from the HPLC peak at 13.17 min in FIG. 54.
Figure 56:
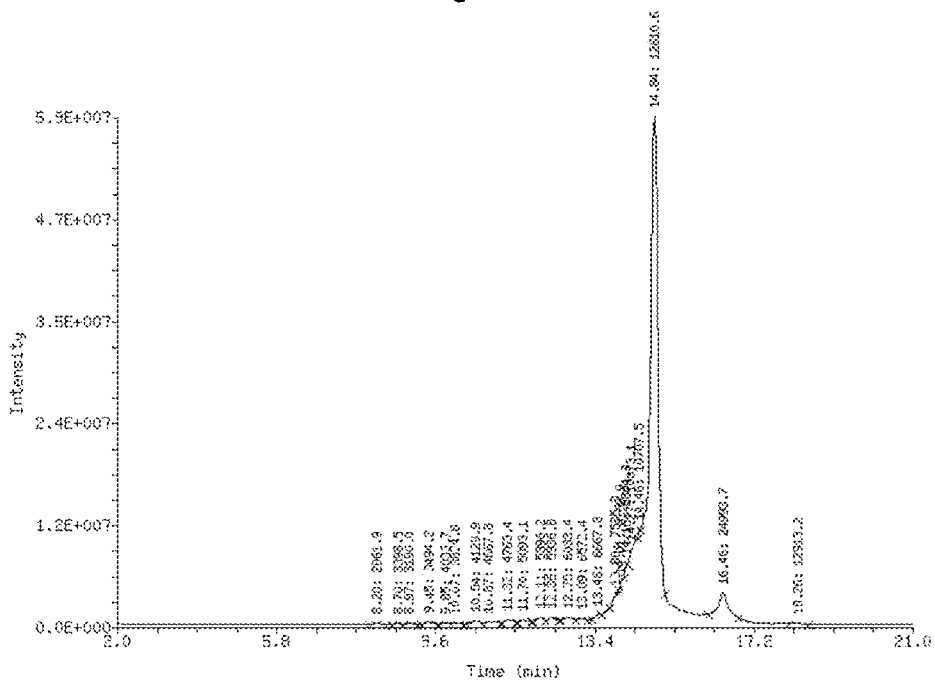
FIG. 56 illustrates a HPLC separation of the REP 2055 calcium chelate/interferon λ1 composition using the oligo method described herein (see Example IV).
Figure 57:
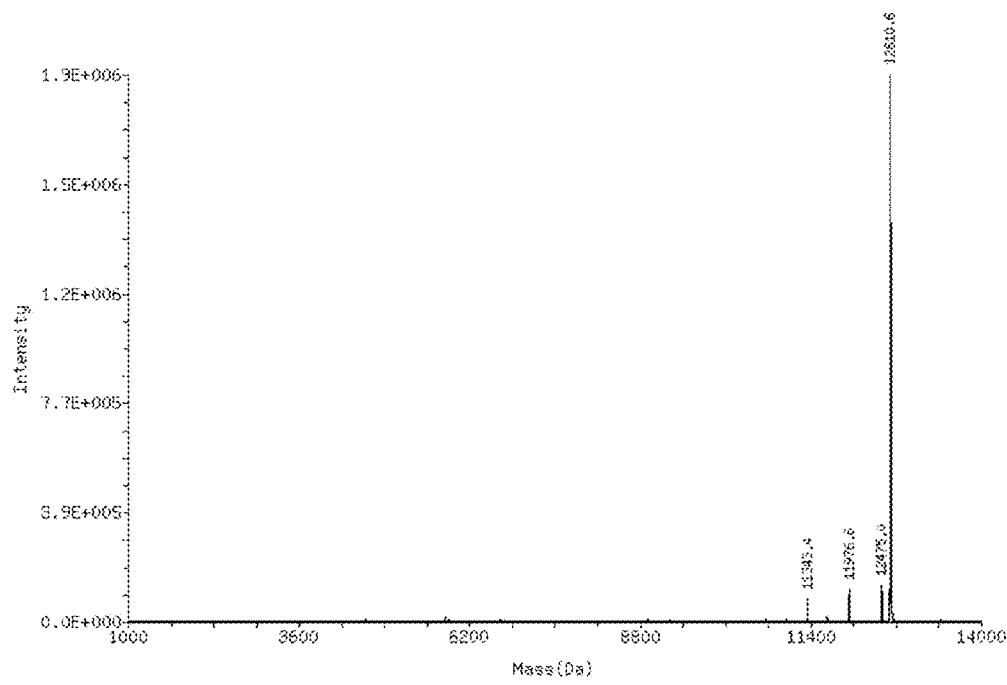
FIG. 57 illustrates an ESI-MS analysis of oligonucleotide content in REP 2055 calcium chelate/interferon λ1 composition from the HPLC peak at 14.84 min in FIG. 56. The observed mass of the primary species is 12610.6 Da, identifying it as REP 2055 (expected m.wt.=12612.5 Da).
Figure 58:
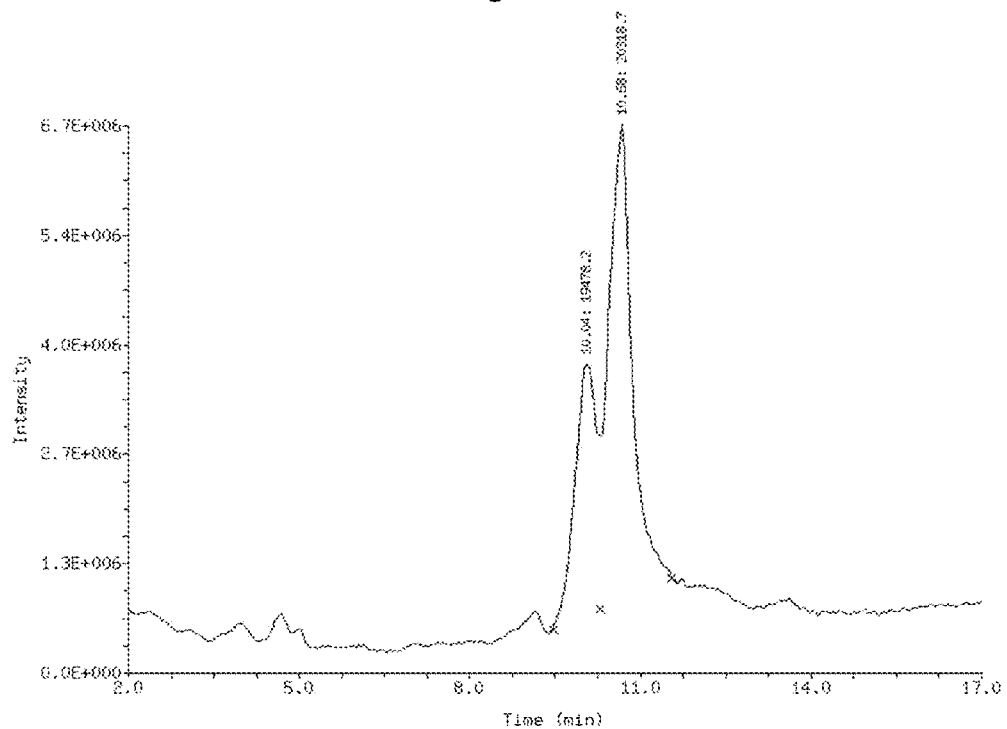
FIG. 58 illustrates a HPLC separation of the REP 2055 calcium chelate/interferon λ1 composition using protein method 2 described herein (see Example IV).
Figure 59:
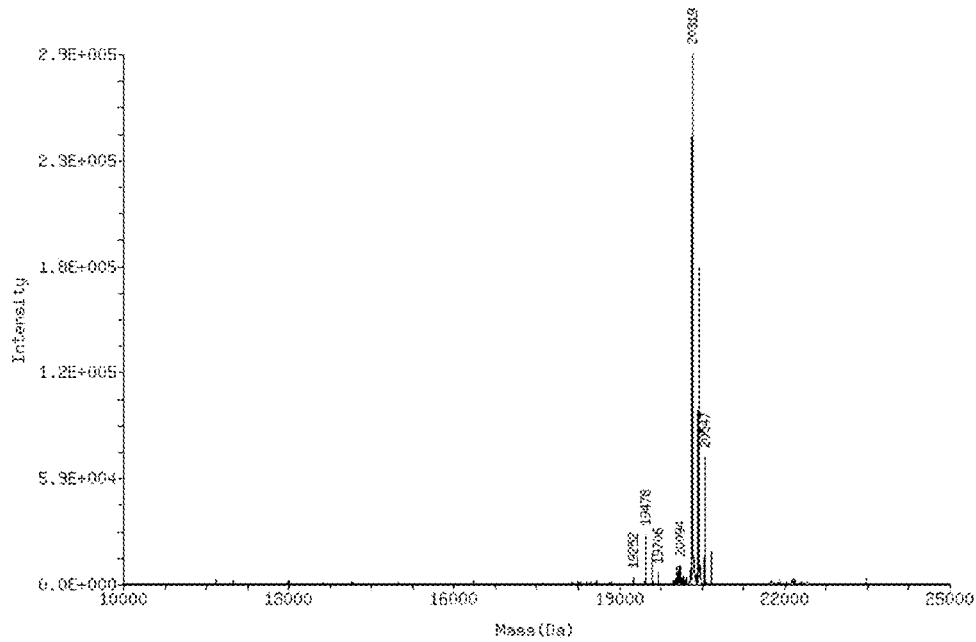
FIG. 59 illustrates an ESI-MS analysis of peptide content in REP 2055 calcium chelate/interferon λ1 composition from the HPLC peak at 10.68 min in FIG. 58. A major peak is observed at 20139 Da, consistent with the approximate molecular weight of interferon λ1.
Figure 60:
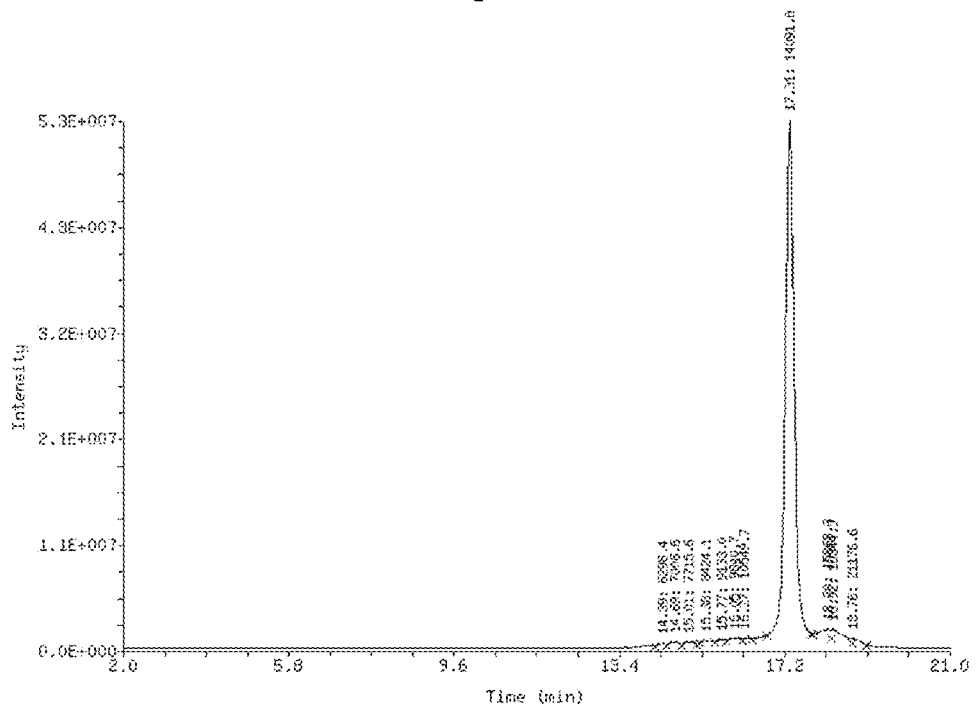
FIG. 60 illustrates a HPLC separation of the REP 2139 calcium chelate/interferon λ1 composition using the oligo method described herein (see Example IV).
Figure 61:
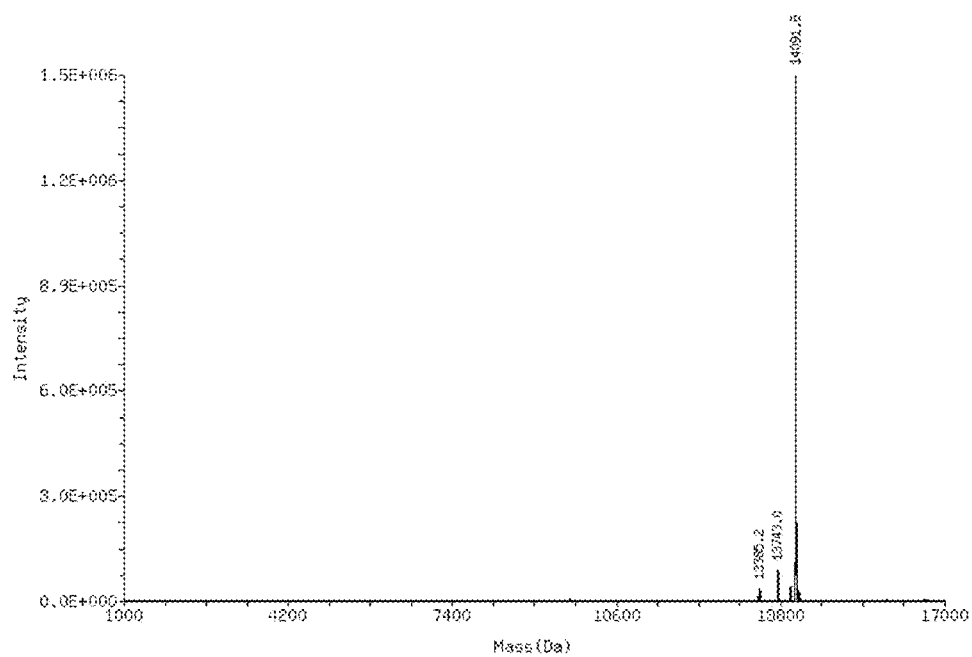
FIG. 61 illustrates an ESI-MS analysis of oligonucleotide content in REP 2139 calcium chelate/interferon λ1 composition from the HPLC peak at 17.31 min in FIG. 60. The observed mass of the primary species is 14095.3 Da, identifying it as REP 2139 (expected m.wt.=14094.6 Da).
Figure 62:
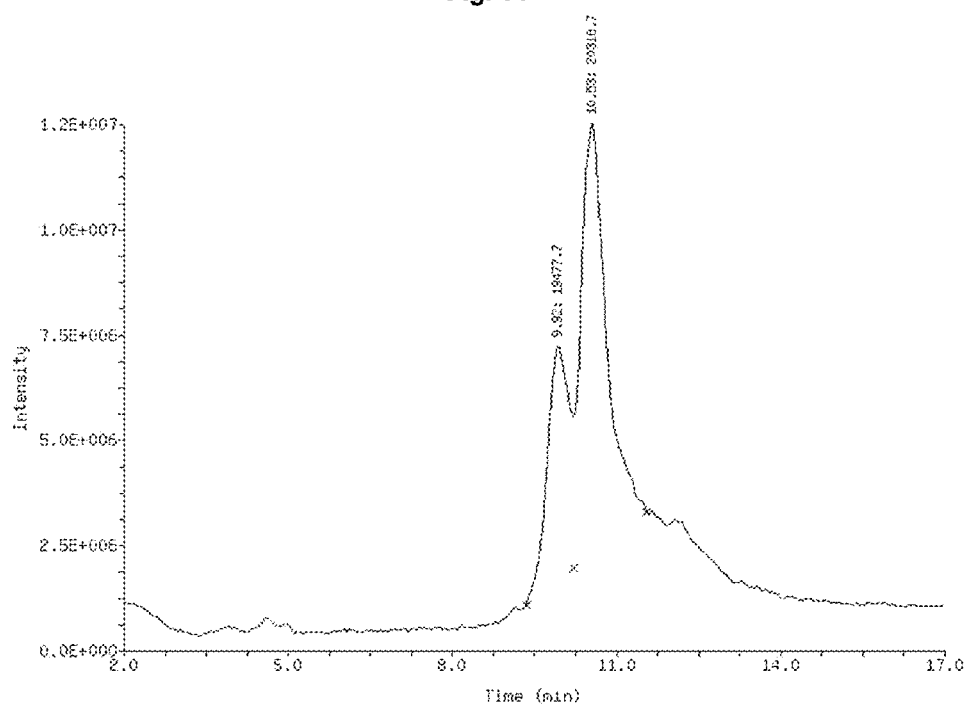
FIG. 62 illustrates a HPLC separation of the REP 2139 calcium chelate/interferon λ1 composition using protein method 2 described herein (see Example IV).
Figure 63:
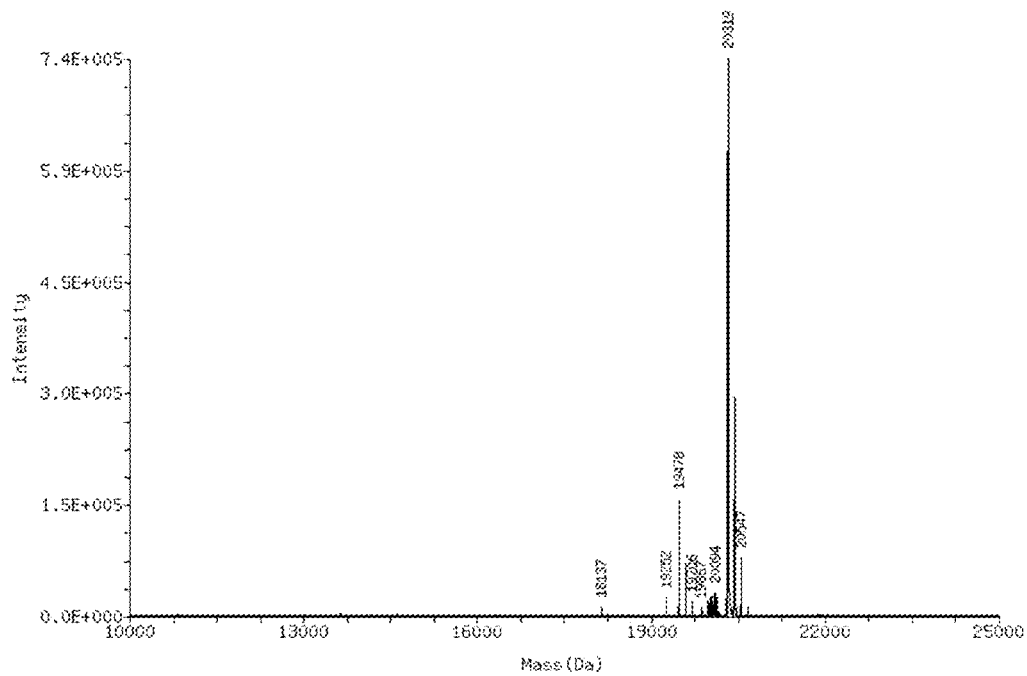
FIG. 63 illustrates an ESI-MS analysis of protein content in REP 2139 calcium chelate/interferon λ1 composition from the HPLC peak at 10.53 min in FIG. 62. A major peak is observed at 20139 Da, consistent with the approximate molecular weight of interferon λ1
Figure 64:
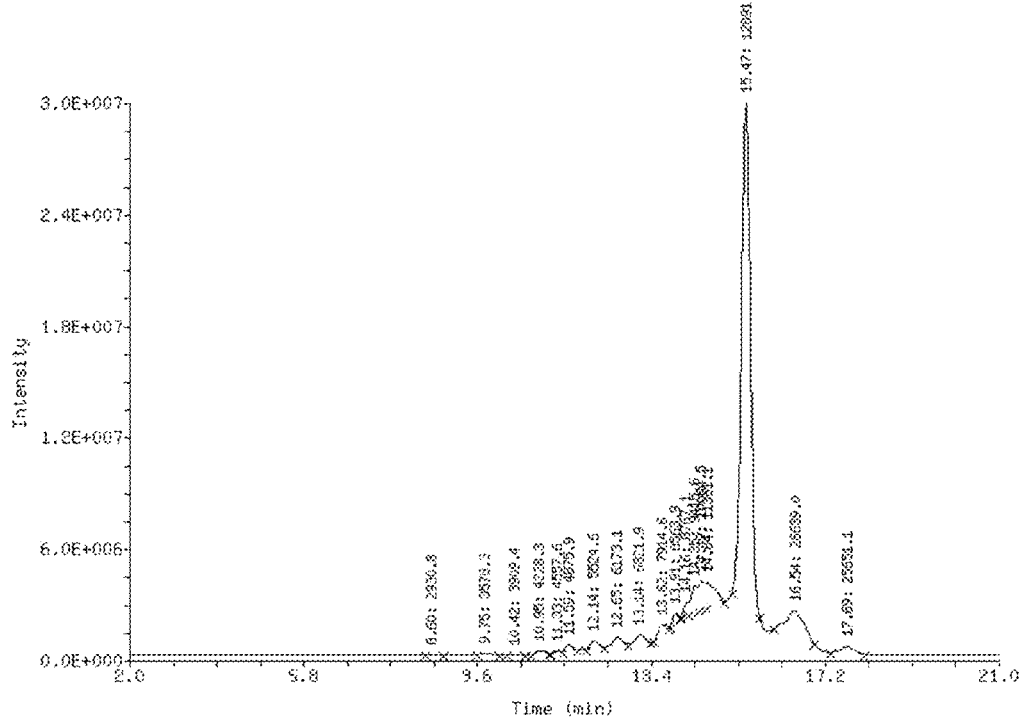
FIG. 64 illustrates a HPLC separation of the REP 2148 calcium chelate/interferon λ1 composition using the oligo method described herein (see Example IV).
Figure 65:
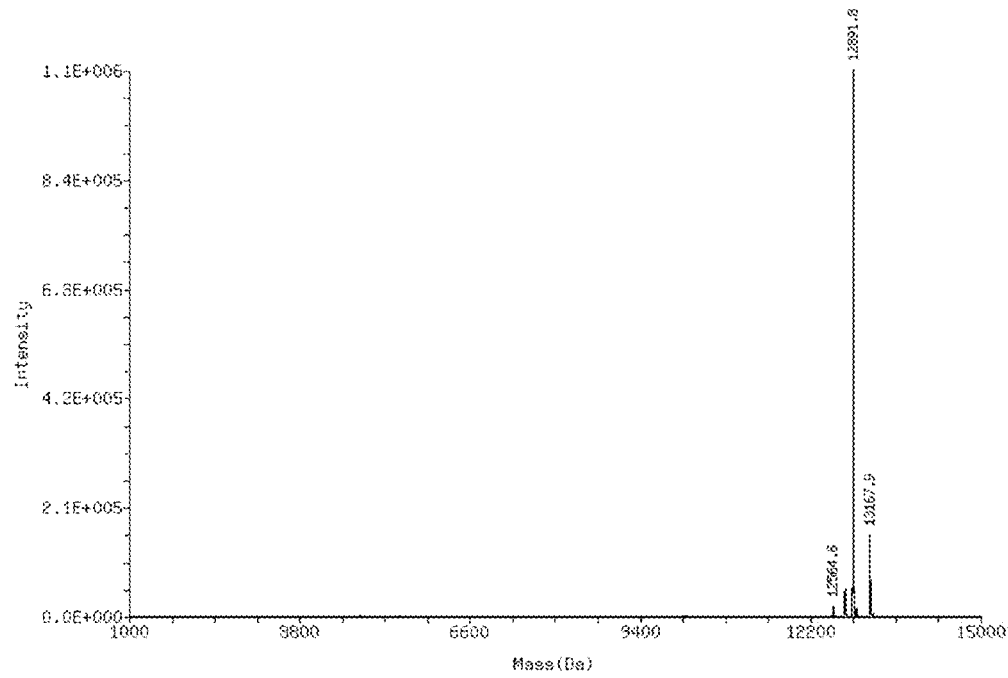
FIG. 65 illustrates an ESI-MS analysis of oligonucleotide content in REP 2148 calcium chelate/interferon λ1 composition from the HPLC peak at 15.47 min in FIG. 64. The observed mass of the primary species is 12891.8 Da, identifying it as REP 2148 (expected m.wt.=12893 Da).
Figure 66:
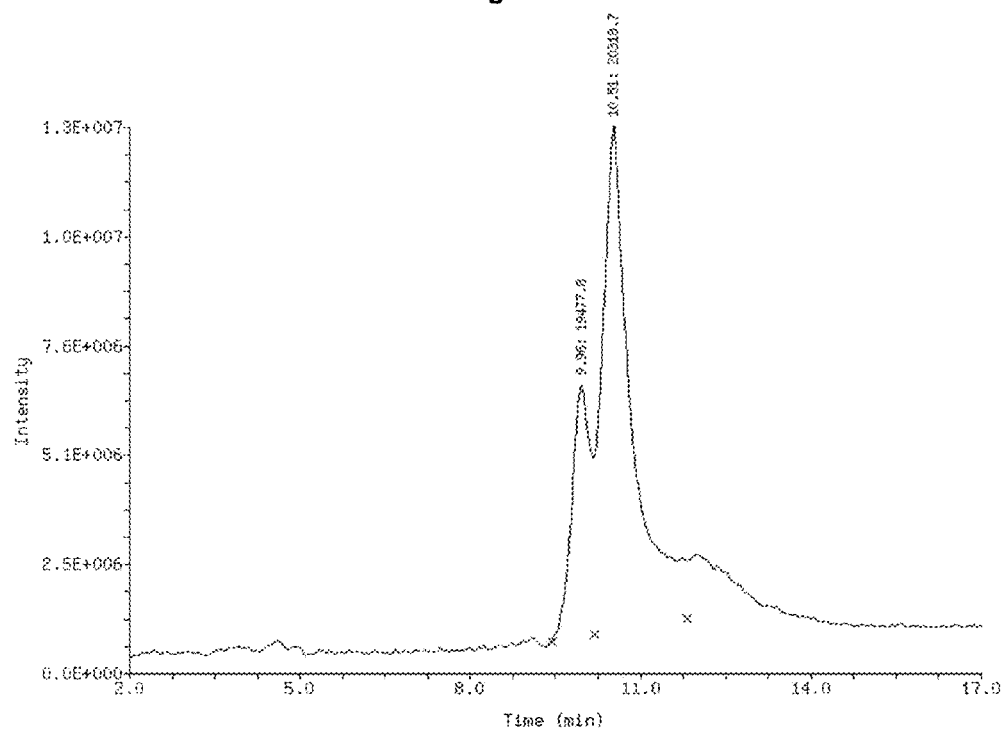
FIG. 66 illustrates a HPLC separation of the REP 2148 calcium chelate/interferon λ1 composition using protein method 2 described herein (see Example IV).
Figure 67:
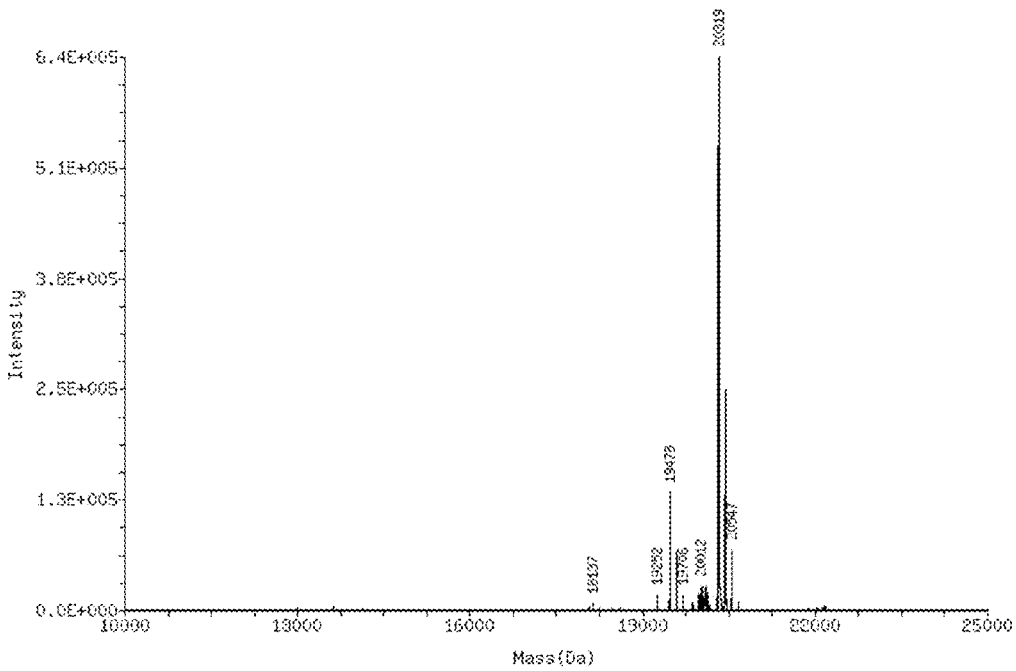
FIG. 67 illustrates an ESI-MS analysis of protein content in REP 2148 calcium chelate/interferon λ1 composition from the HPLC peak at 10.51 min in FIG. 66. A major peak is observed at 20139 Da, consistent with the approximate molecular weight of interferon λ1
Figure 68:
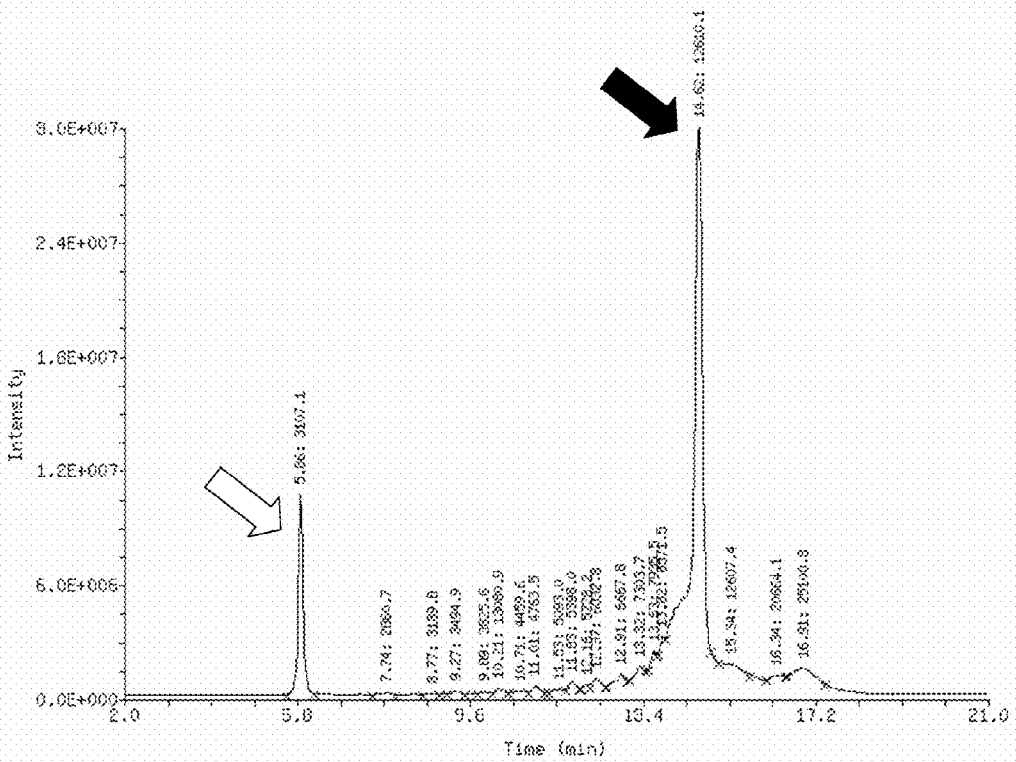
FIG. 68 illustrates a HPLC separation of the REP 2055 magnesium chelate/thymosin α1 composition using the oligo method described herein (see Example IV). The peak eluting at 5.86 min corresponds to thymosin α1 (white arrow) and the peak eluting at 14.62 min corresponds to the full length REP 2055 (black arrow).
Figure 69:
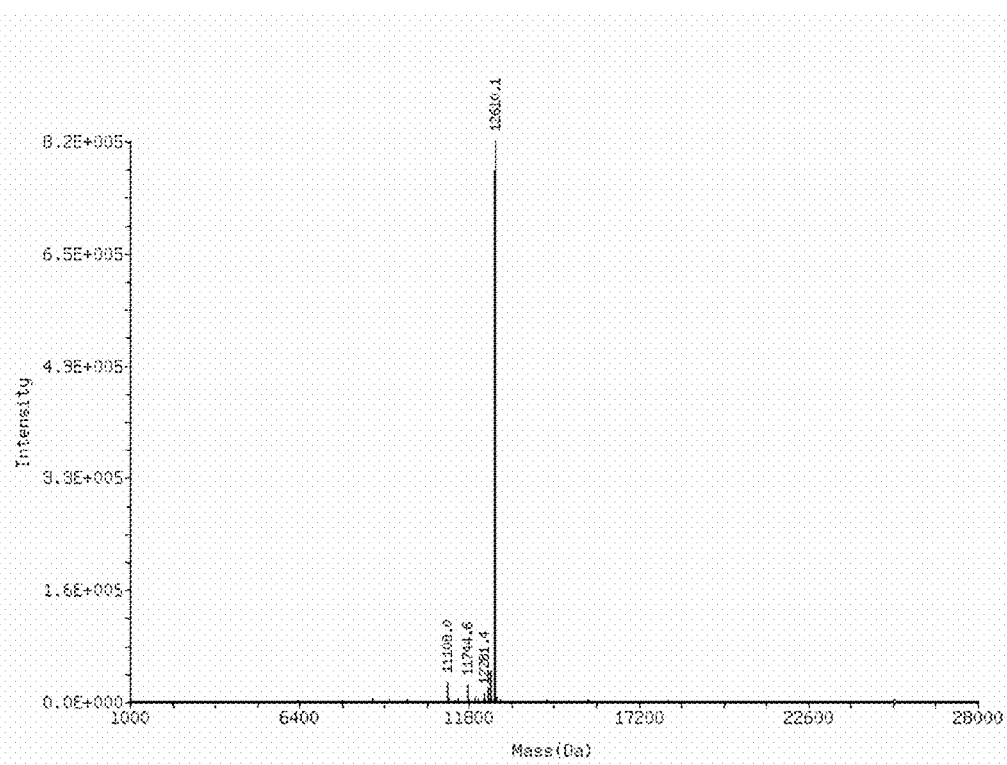
FIG. 69 illustrates an ESI-MS analysis of oligonucleotide content in REP 2055 magnesium chelate/thymosin α1 composition from the HPLC peak at 14.62 min in FIG. 68. The observed mass of the primary species is 12610.1 Da, identifying it as REP 2055 (expected m. wt.=12612.5).
Figure 70:
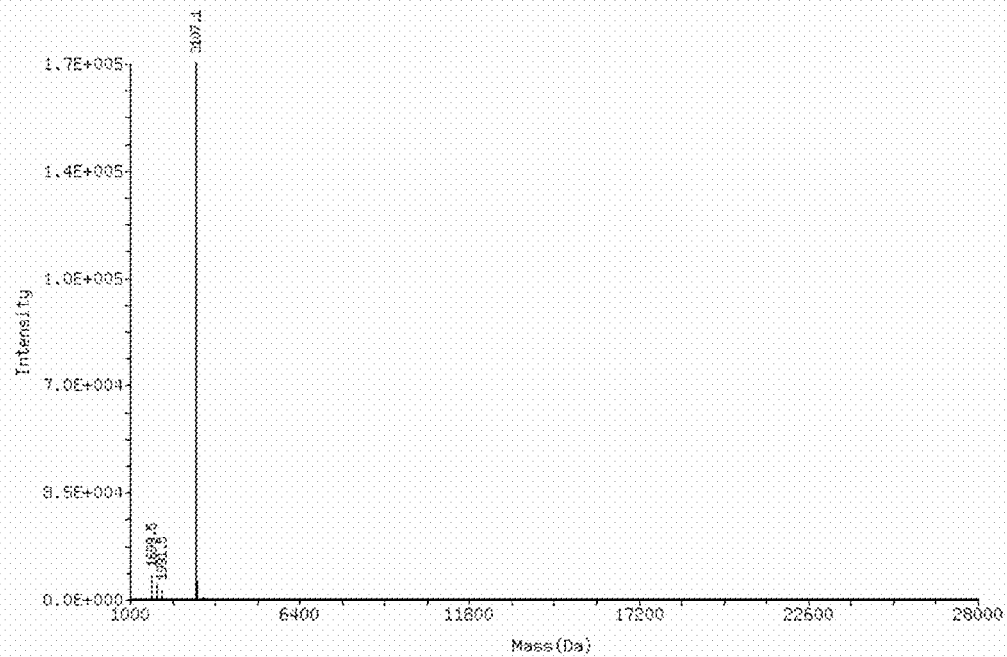
FIG. 70 illustrates an ESI-MS analysis of peptide content in REP 2055 magnesium chelate/thymosin α1 composition from the HPLC peak at 5.82 min in FIG. 68. The observed mass of the primary species is 3107.1 Da, identifying it as thymosin α1 (expected m.wt.=3108 Da).
Figure 71:
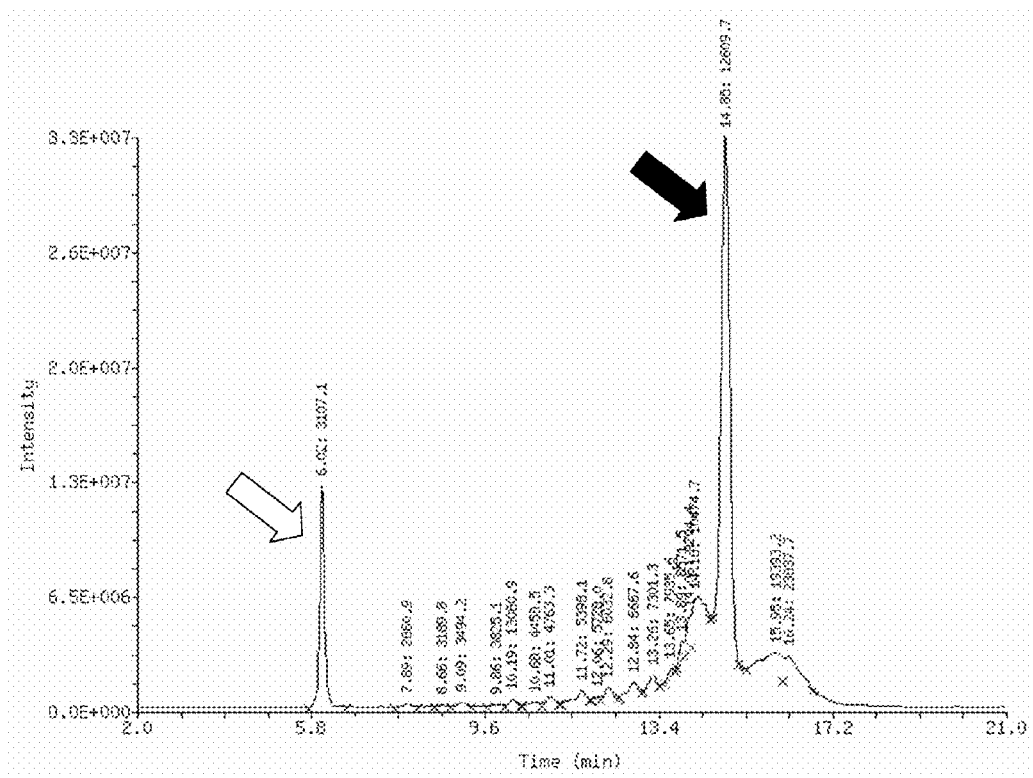
FIG. 71 illustrates a HPLC separation of the REP 2055 mixed calcium-magnesium chelate/thymosin α1 composition using the oligo method described herein (see Example IV). The peak eluting at 6.02 min corresponds to thymosin α1 (white arrow) and the peak eluting at 14.85 min corresponds to the full length REP 2055 (black arrow).
Figure 72:
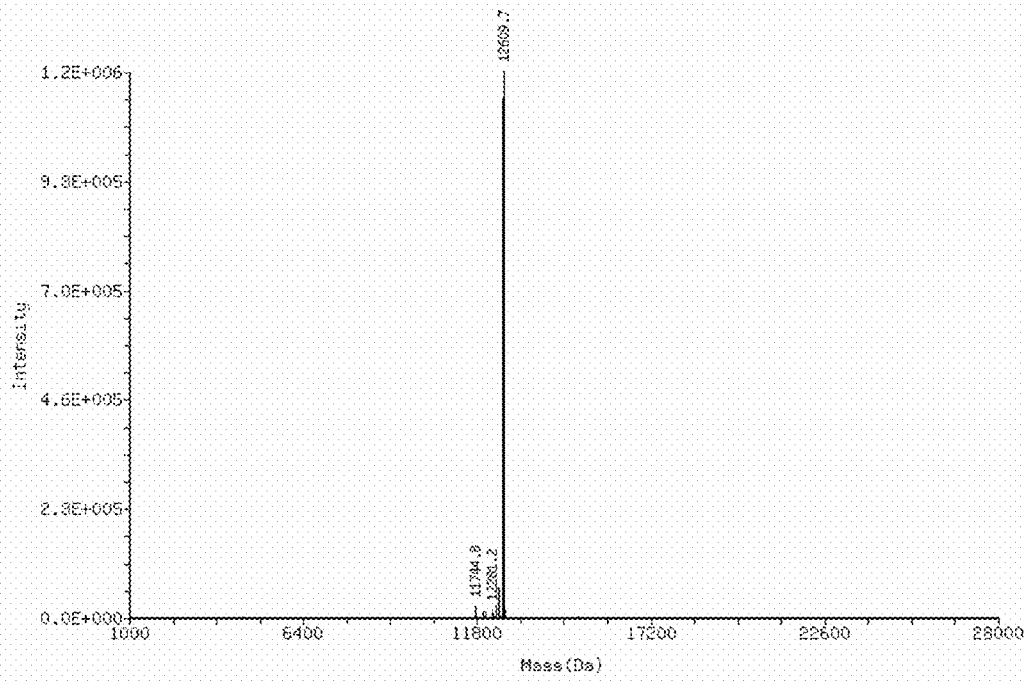
FIG. 72 illustrates an ESI-MS analysis of oligonucleotide content in REP 2055 mixed calcium-magnesium chelate/thymosin α1 composition from the HPLC peak at 14.85 min in FIG. 71. The observed mass of the primary species is 12609.7 Da, identifying it as REP 2055 (expected m. wt.=12612.5).
Figure 73:
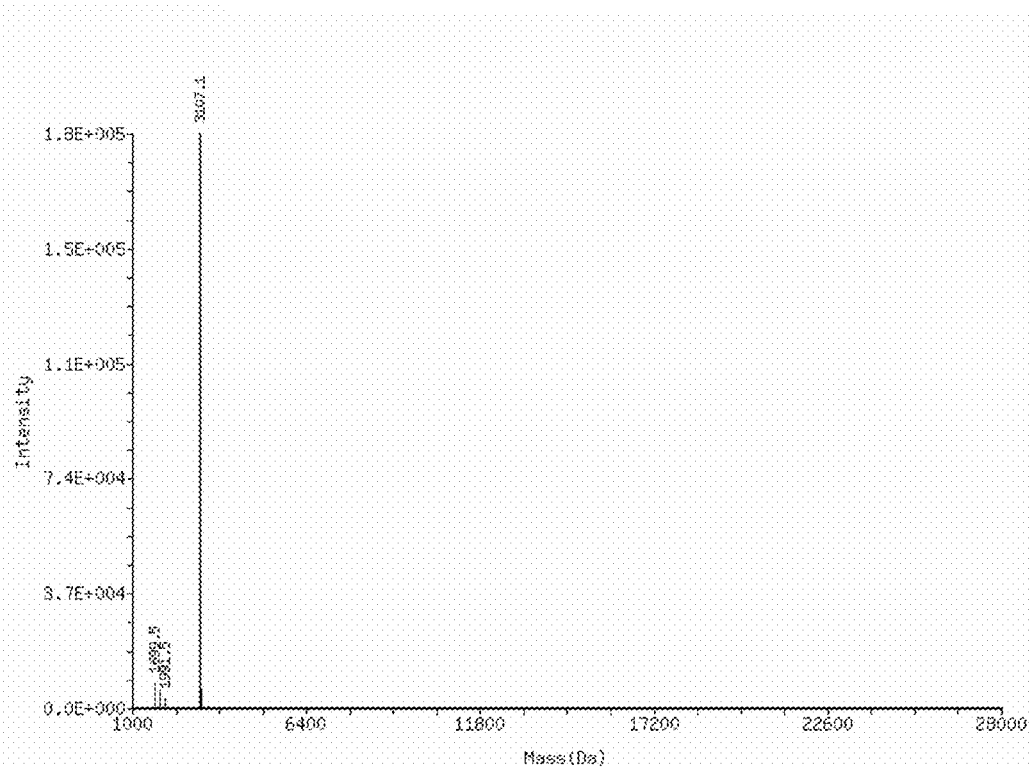
FIG. 73 illustrates an ESI-MS analysis of peptide content in REP 2055 mixed calcium magnesium chelate/thymosin α1 composition from the HPLC peak at 6.02 min in FIG. 71. The observed mass of the primary species is 3107.1 Da, identifying it as thymosin α1 (expected m.wt.=3108 Da).
Figure 74:
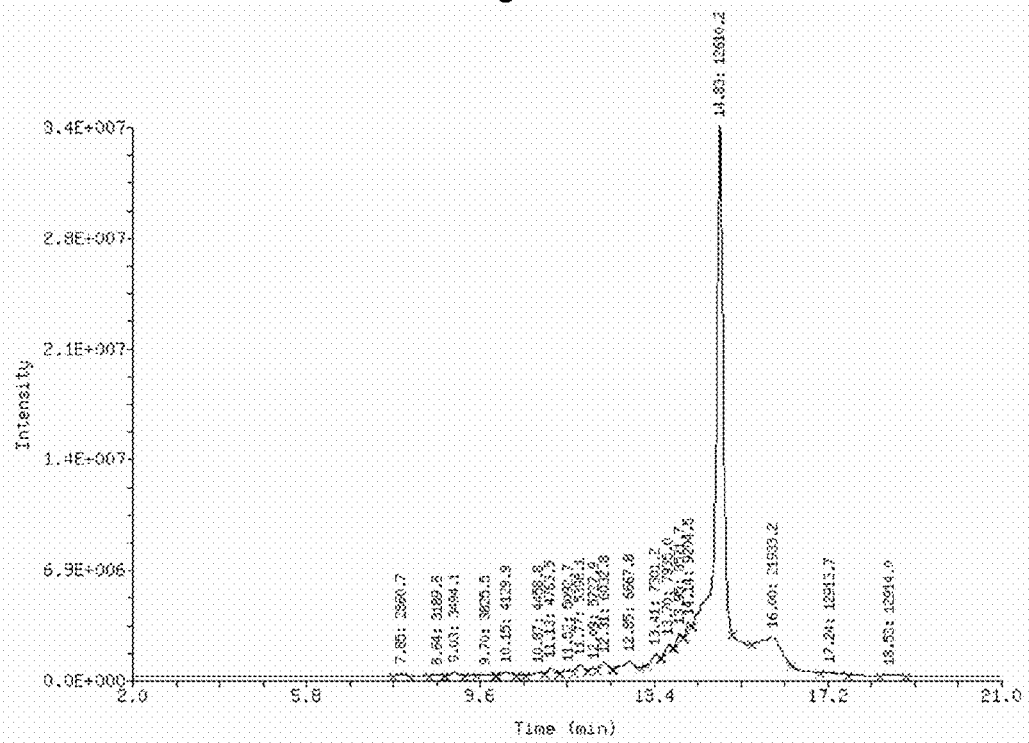
FIG. 74 illustrates a HPLC separation of the REP 2055 magnesium chelate/pegylated interferon α-2a composition using the oligo method described herein (see Example IV).
Figure 75:
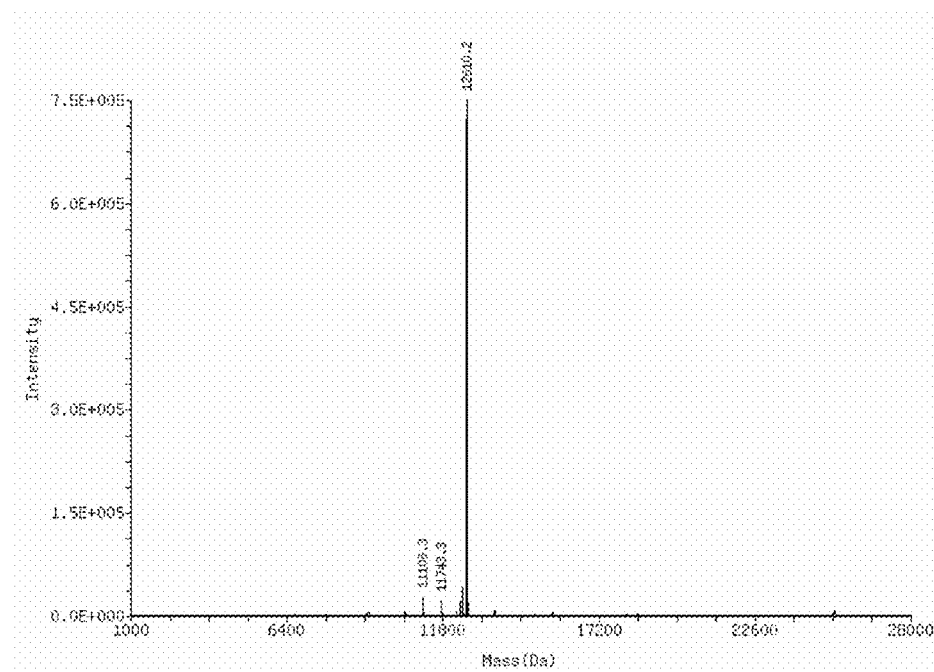
FIG. 75 illustrates an ESI-MS analysis of oligonucleotide content in REP 2055 magnesium chelate/pegylated interferon α-2a composition from the HPLC peak at 14.83 min in FIG. 74. The observed mass of the primary species is 12610.2 Da, identifying it as REP 2055 (expected m.wt.=12612.5 Da).
Figure 76:
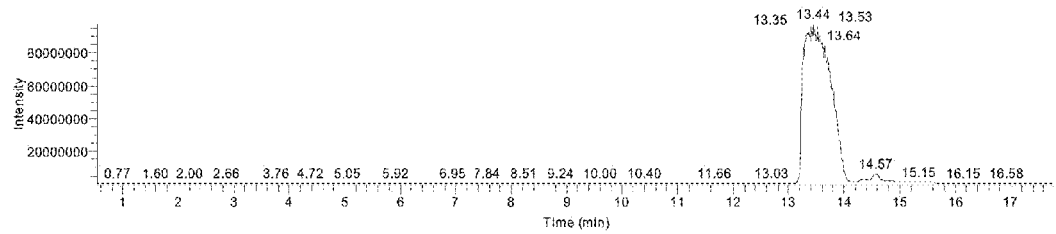
FIG. 76 illustrates a HPLC separation of the REP 2055 magnesium chelate/pegylated interferon α-2a composition using protein method 2 described herein (see Example IV).
Figure 77:
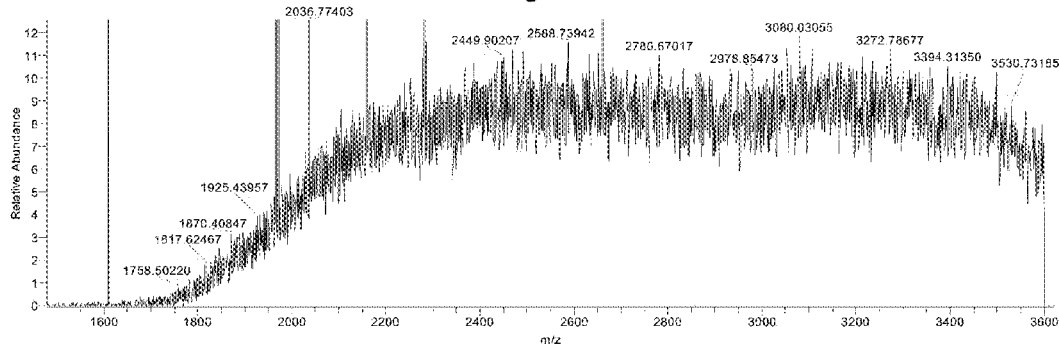
FIG. 77 illustrates an ESI-MS analysis of peptide content in REP 2055 magnesium chelate/pegylated interferon α-2a composition from the HPLC peak at 13.44 min in FIG. 76.
Figure 78:
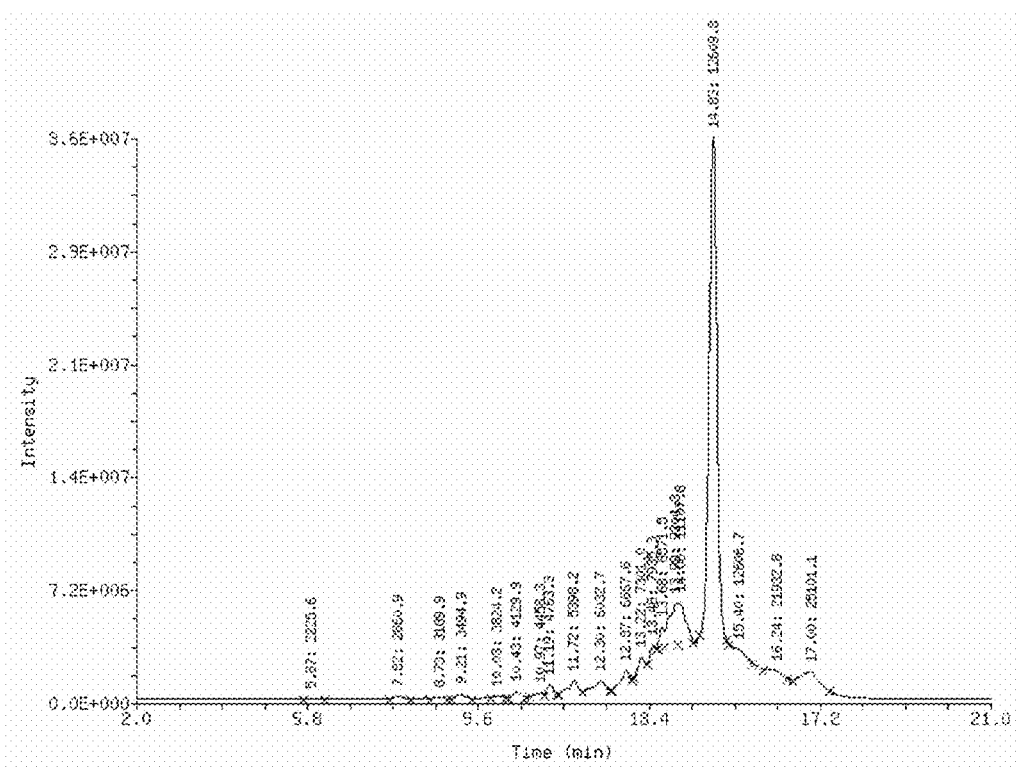
FIG. 78 illustrates a HPLC separation of the REP 2055 mixed calcium-magnesium chelate/pegylated interferon α-2a composition using the oligo method described herein (see Example IV).
Figure 79:
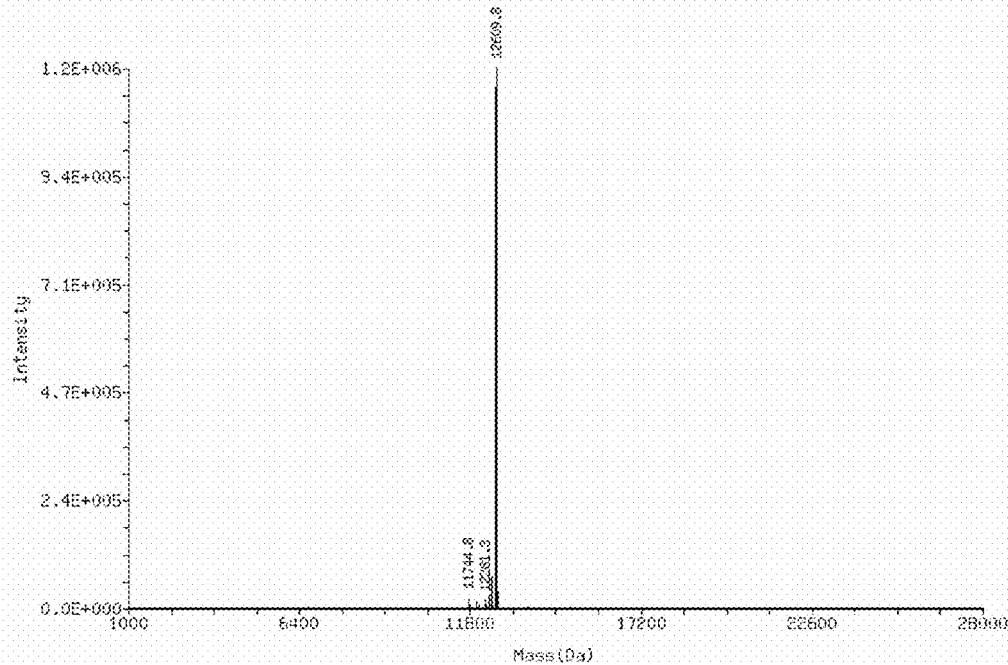
FIG. 79 illustrates an ESI-MS analysis of oligonucleotide content in REP 2055 mixed calcium-magnesium chelate/pegylated interferon α-2a composition from the HPLC peak at 14.83 min in FIG. 78. The observed mass of the primary species is 12609.8 Da, identifying it as REP 2055 (expected m.wt.=12612.5 Da).
Figure 80:
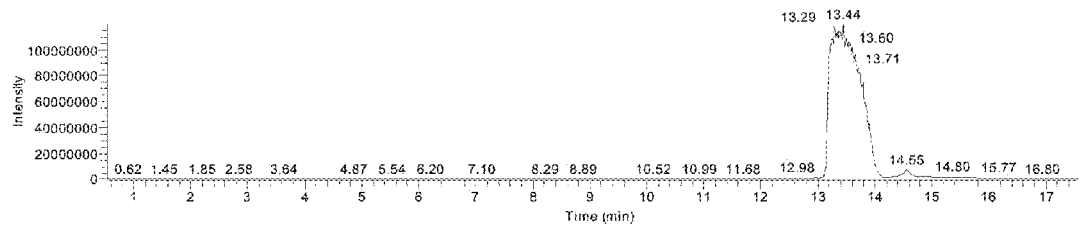
FIG. 80 illustrates a HPLC separation of the REP 2055 mixed calcium-magnesium chelate/pegylated interferon α-2a composition using protein method 2 described herein (see Example IV).
Figure 81:
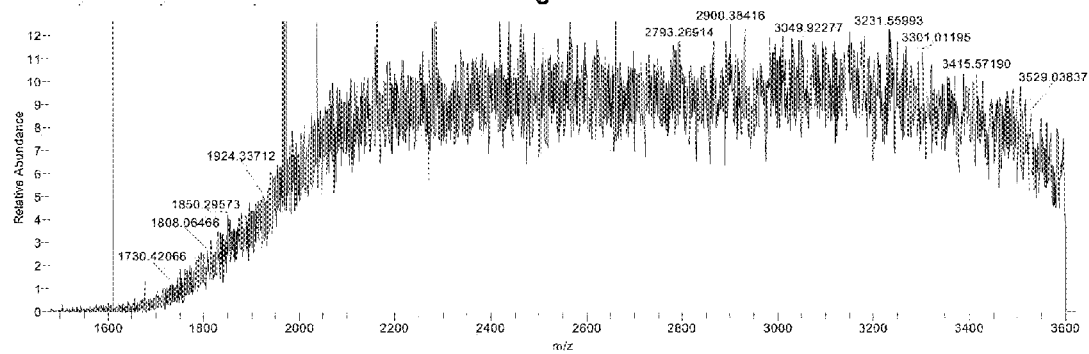
FIG. 81 illustrates an ESI-MS analysis of peptide content in REP 2055 mixed calcium-magnesium chelate/pegylated interferon α-2a composition from the HPLC peak at 13.44 min in FIG. 80.
Figure 82:
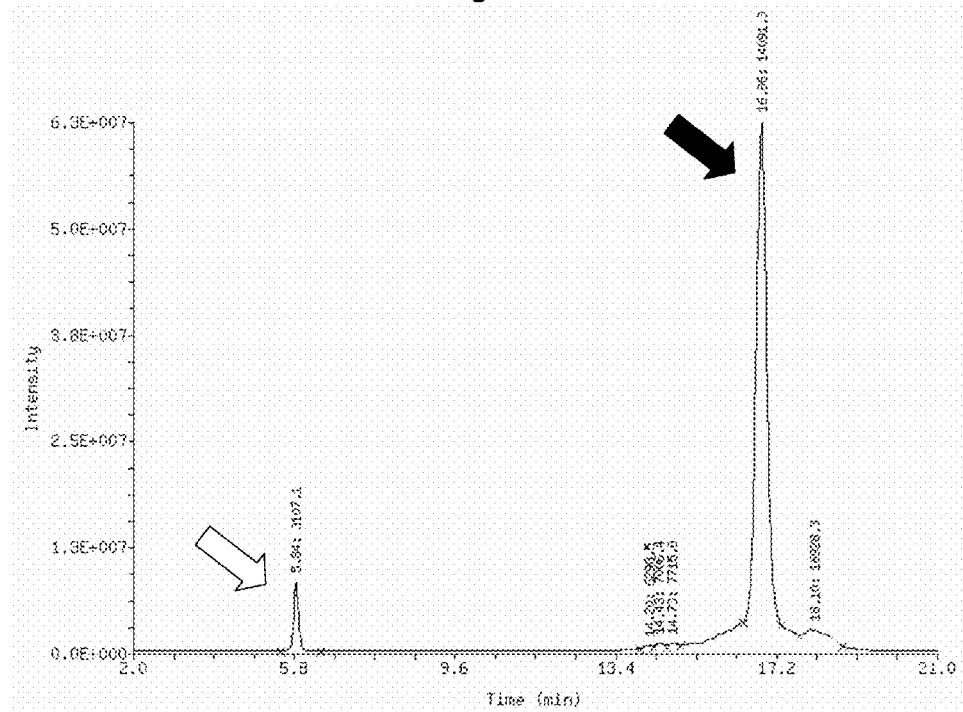
FIG. 82 illustrates a HPLC separation of the REP 2139 magnesium chelate/thymosin α1 composition using the oligo method described herein (see Example IV). The peak eluting at 5.84 min corresponds to thymosin α1 (white arrow) and the peak eluting at 16.86 min corresponds to the full length REP 2139 (black arrow).
Figure 83:
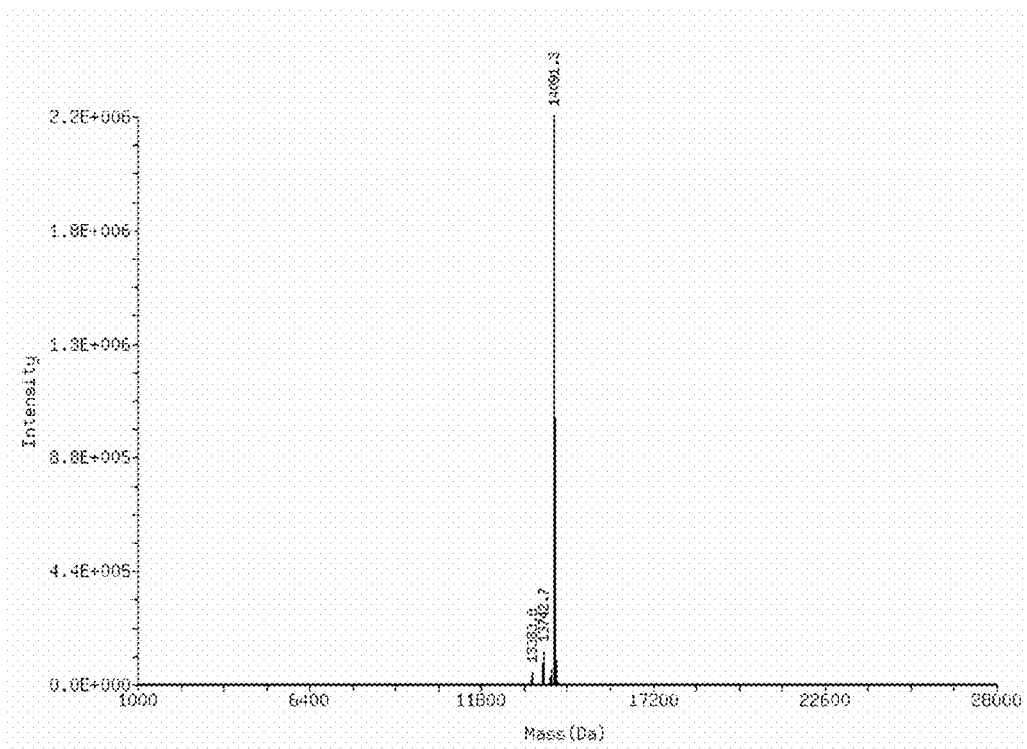
FIG. 83 illustrates an ESI-MS analysis of oligonucleotide content in REP 2139 magnesium chelate/thymosin α1 composition from the HPLC peak at 16.86 min in FIG. 82. The observed mass of the primary species is 14091.3 Da, identifying it as REP 2139 (expected m.wt.=14094.6 Da).
Figure 84:
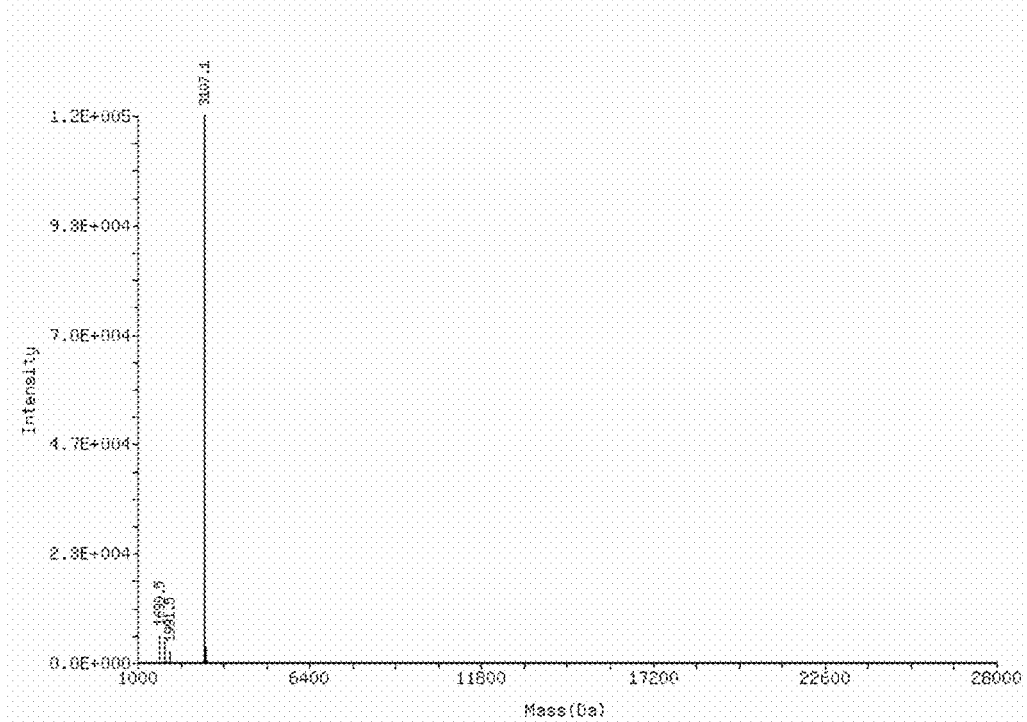
FIG. 84 illustrates an ESI-MS analysis of peptide content in REP 2139 magnesium chelate/thymosin α1 composition from the HPLC peak at 5.84 min in FIG. 82. The observed mass of the primary species is 3107.1 Da, identifying it as thymosin α1 (expected m.wt.=3108 Da).
Figure 85:
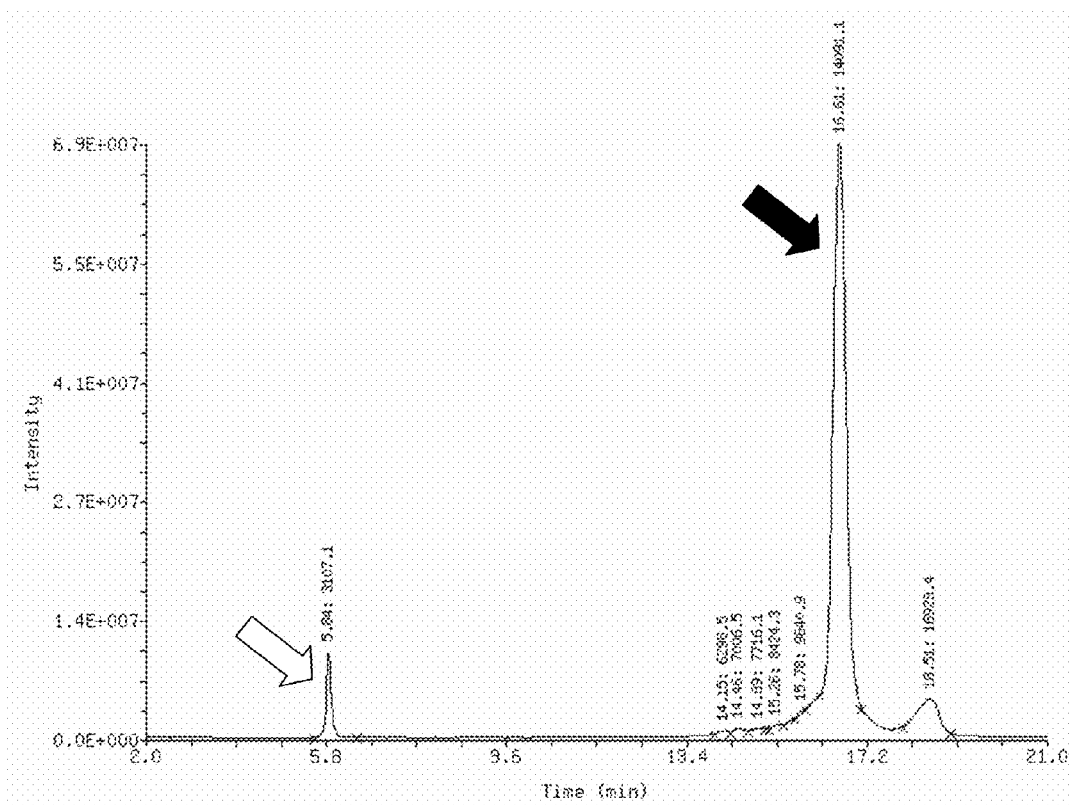
FIG. 85 illustrates a HPLC separation of the REP 2139 mixed calcium-magnesium chelate/thymosin α1 composition using the oligo method described herein (see Example IV). The peak eluting at 5.84 min corresponds to thymosin α1 (white arrow) and the peak eluting at 16.61 min corresponds to the full length REP 2139 (black arrow).
Figure 86:
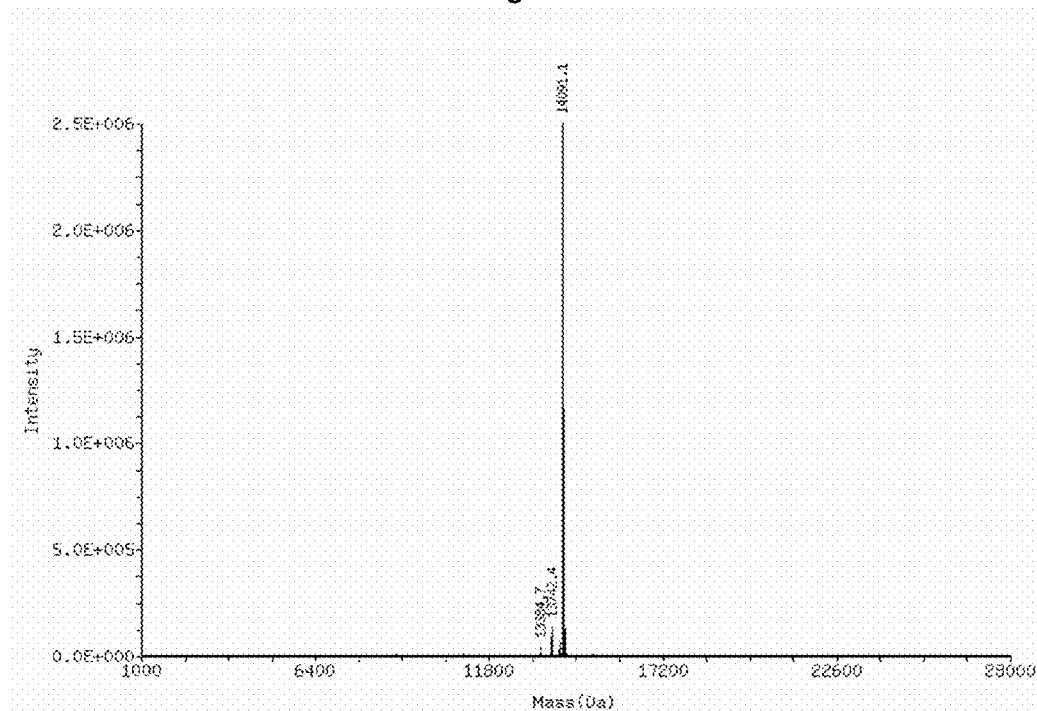
FIG. 86 illustrates an ESI-MS analysis of oligonucleotide content in REP 2139 mixed calcium-magnesium chelate/thymosin α1 composition from the HPLC peak at 16.61 min in FIG. 85. The observed mass of the primary species is 14091.1 Da, identifying it as REP 2139 (expected m.wt.=14094.6 Da).
Figure 87:
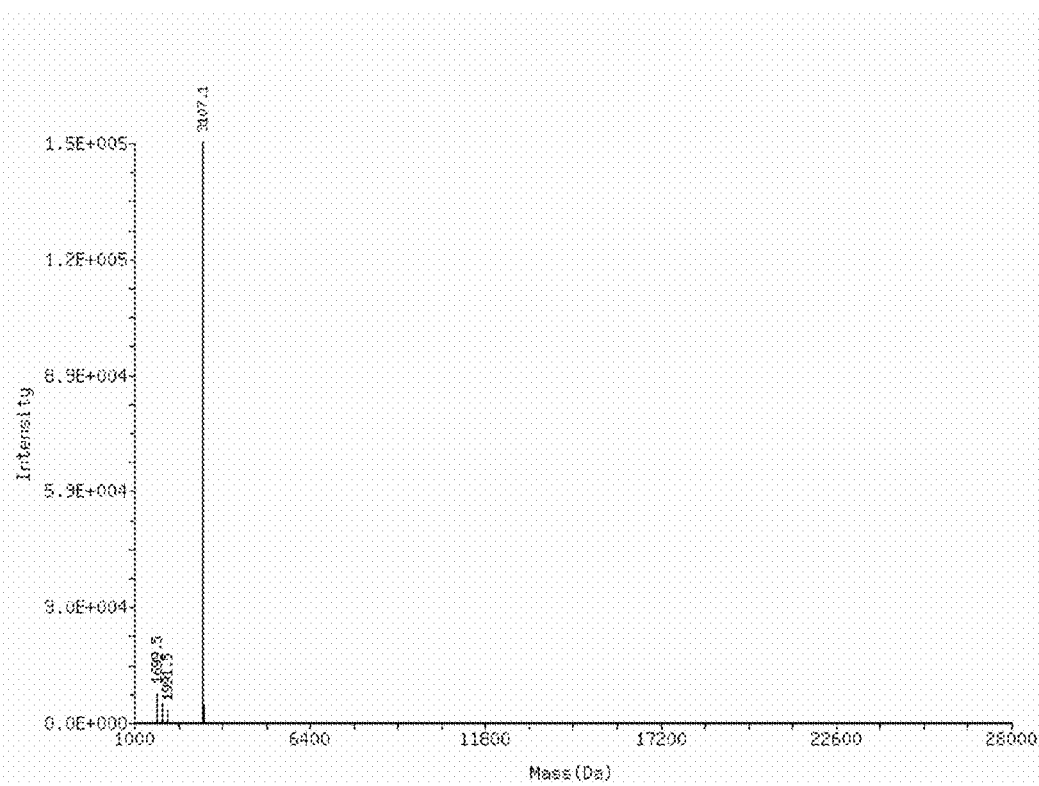
FIG. 87 illustrates an ESI-MS analysis of peptide content in REP 2139 mixed calcium magnesium chelate/thymosin α1 composition from the HPLC peak at 5.84 min in FIG. 85. The observed mass of the primary species is 3107.1 Da, identifying it as thymosin α1 (expected m.wt.=3108 Da).
Figure 88:
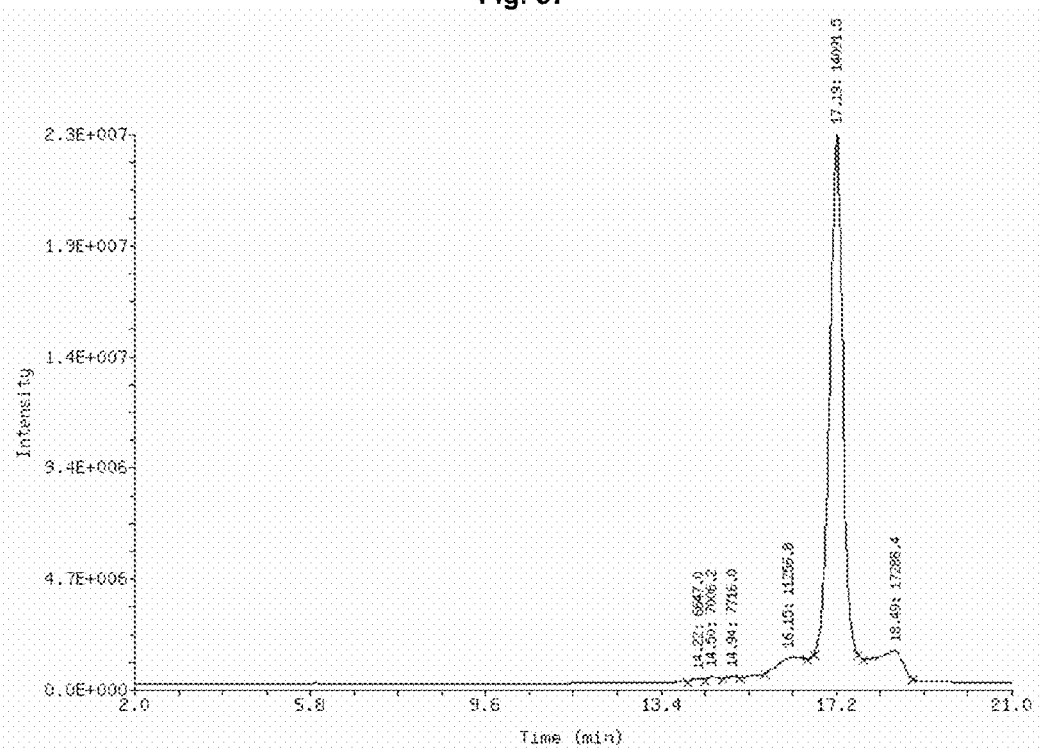
FIG. 88 illustrates a HPLC separation of the REP 2139 magnesium chelate/pegylated interferon α-2a composition using the oligo method described herein (see Example IV).
Figure 89:
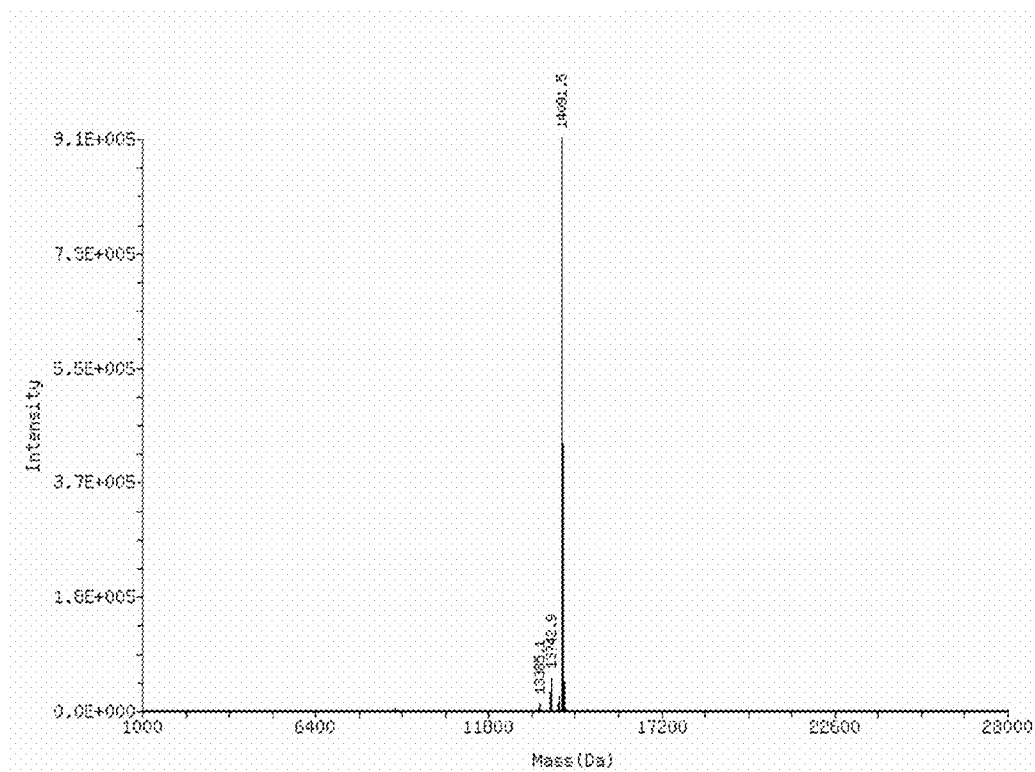
FIG. 89 illustrates an ESI-MS analysis of oligonucleotide content in REP 2139 magnesium chelate/pegylated interferon α-2a composition from the HPLC peak at 17.19 min in FIG. 88. The observed mass of the primary species is 14091.5 Da, identifying it as REP 2139 (expected m.wt.=14094.6 Da).
Figure 90:
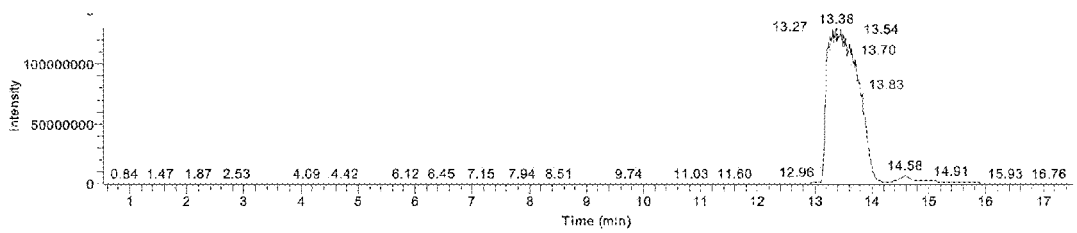
FIG. 90 illustrates a HPLC separation of the REP 2139 magnesium chelate/pegylated interferon α-2a composition using protein method 2 described herein (see Example IV).
Figure 91:
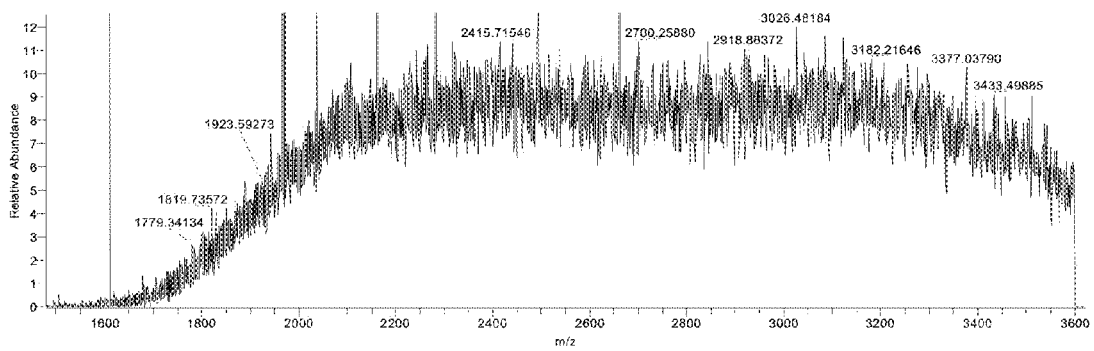
FIG. 91 illustrates an ESI-MS analysis of peptide content in REP 2139 magnesium chelate/pegylated interferon α-2a composition from the HPLC peak at 13.38 min in FIG. 90.
Figure 92:
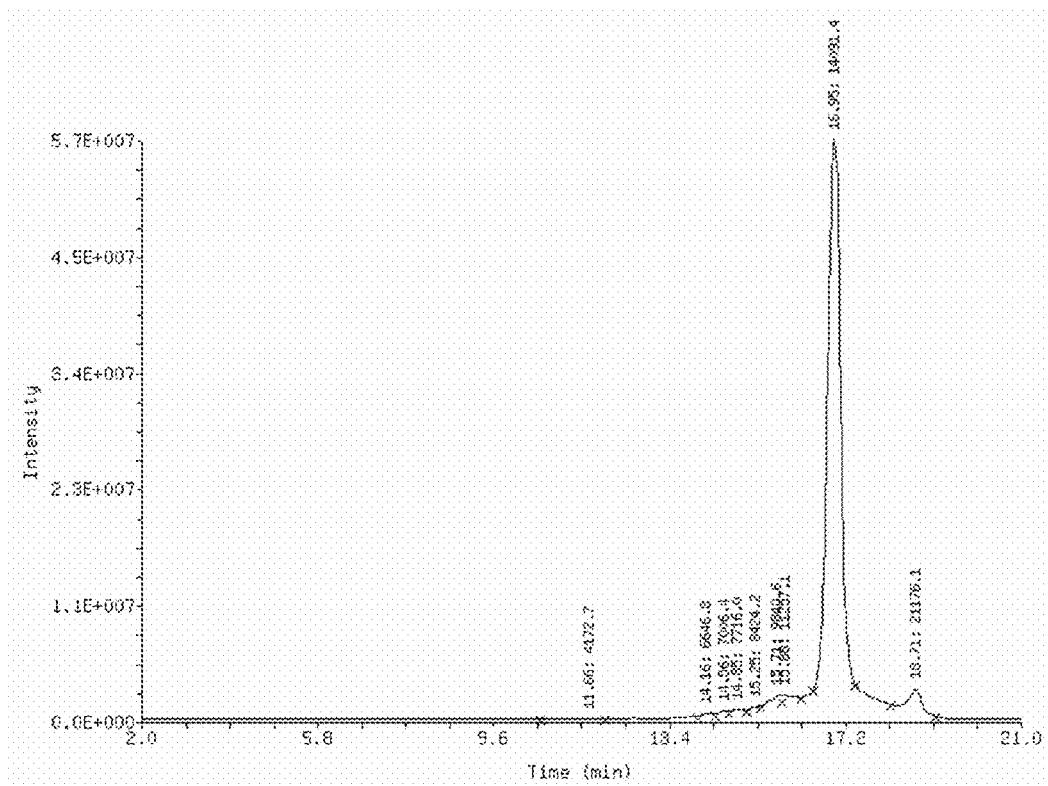
FIG. 92 illustrates a HPLC separation of the REP 2139 mixed calcium-magnesium chelate/pegylated interferon α-2a composition using the oligo method described herein (see Example IV).
Figure 93:
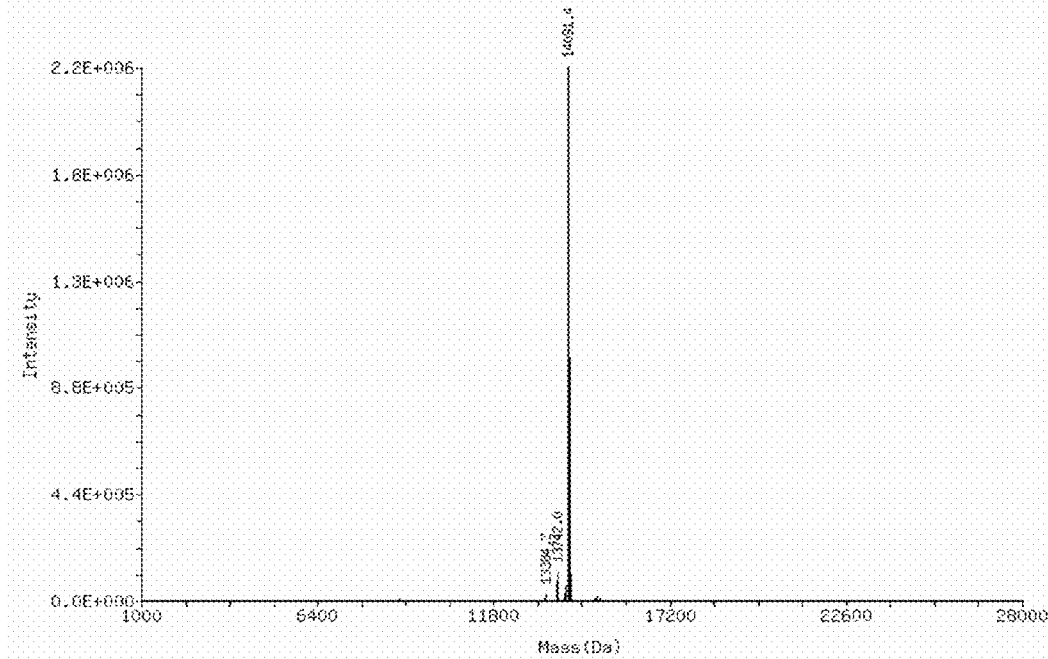
FIG. 93 illustrates an ESI-MS analysis of oligonucleotide content in REP 2139 mixed calcium-magnesium chelate/ pegylated interferon α-2a composition from the HPLC peak at 16.95 min in FIG. 92. The observed mass of the primary species is 14091.4 Da, identifying it as REP 2139 (expected m.wt.=14094.6 Da).
Figure 94:
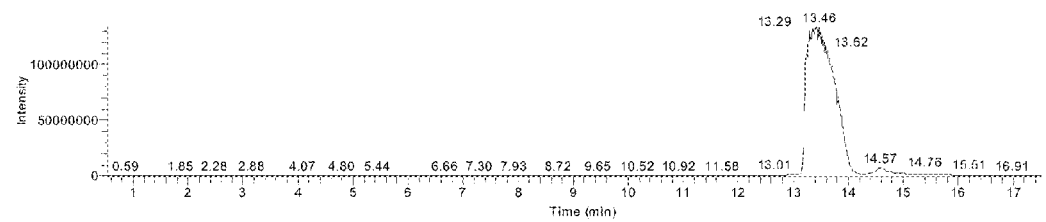
FIG. 94 illustrates a HPLC separation of the REP 2139 mixed calcium-magnesium chelate/pegylated interferon α-2a composition using protein method 2 described herein (see Example IV).

LC-MS analysis of ON content of all compositions demonstrated that the ONs present in these compositions corresponded with their expected purity: minor amounts of incomplete ON synthesis products were observed in HPLC analyses using the oligo method for REP 2055 (FIGS. 5, 24, 40 56, 68, 71, 74 and 78), REP 2057 (FIGS. 9, 27 and 44) and REP 2148 (FIGS. 17, 33, 52 and 64) but were absent in the case of REP 2139 (FIGS. 13, 30, 48, 60, 82, 85, 88 and 92). In all cases, ESI-MS of the lead (primary) ON peaks correlated almost perfectly with the expected molecular weights of REP 2055, REP 2057, REP 2139 and REP 2148. For REP 2006, ESI-MS of the lead peak produced a broadly distributed peak in the 12612-13092 Da range, consistent with its degenerate nature (FIGS. 22 and 37).

For the analysis of compositions containing interferon α-2b, HPLC chromatograms run using protein method 1 showed a large, poorly resolved peaks consistent with the presence of more than one polypeptide in these compositions (FIGS. 7, 11, 15 and 19) but the lead peak resolved into two distinct mass species correlating almost exactly to the expected molecular weights for interferon α-2b and human albumin (FIGS. 8, 12, 16 and 20).

For compositions containing thymosin α1, HPLC chromatograms obtained from oligo method 1 were able to capture a second prominent peak in the same separation with a much smaller retention time than the (primary) ON peak (FIGS. 21, 24, 27, 30, 33, 68, 71, 82 and 85) due to the relatively low molecular weight of this polypeptide. In all cases, ESI-MS of this secondary peak was correlated almost exactly with the expected molecular weight of thymosin α1 (FIGS. 23, 26, 29, 32, 35, 70, 73, 84 and 87).

For compositions containing pegylated interferon α-2a, LC-MS analysis is greatly complicated by the presence of the pegylated conjugate, which generates numerous ion species which make correct deconvolution of the mass spectrum for any pegylated polypeptide very difficult. However, using protein method 2, HPLC data from compositions containing pegylated interferon α-2a all showed similar prominent peaks consistent with the retention times expected for a pegylated polypeptide (FIGS. 38, 42, 46, 50, 54, 76, 80, 90 and 94). ESI-MS analyses of these peaks in all cases showed a similar group of pegylation related signals from m/z 600-100- and 1500-3600 consistent with the presence of a pegylated protein (FIGS. 39, 43, 47, 51, 55, 77, 81, 91 and 95).

A portion of all the oligonucleotide chelate—polypeptide compositions prepared in Example III were also subjected to calcium and or magnesium determination by inductively coupled plasma optical emission spectroscopy (ICP-OES). The calcium and magnesium determinations for each composition analyzed are presented in Table 3.

TABLE 3

Metal determination of ON chelate complex-polypeptide compositions.

| ON present (as chelate) | Polypeptide present | Metal content (% of total mass as determined by ICP-OES) | |
| --- | --- | --- | --- |
| | | Calcium | Magnesium |
| REP 2006 | thymosin α1 | 0.107% | not present |
| REP 2006 | pegylated interferon α-2a | 0.0991% | not present |
| REP 2055 | interferon α-2b | 0.0242% | not present |
| REP 2055 | thymosin α1 | 0.0393% | not present |
| REP 2055 | pegylated interferon α-2a | 0.0448% | not present |
| REP 2055 | interferon λ1 | 0.0515% | not present |
| REP 2057 | interferon α-2b | 0.0987% | not present |
| REP 2057 | thymosin α1 | 0.101% | not present |
| REP 2057 | pegylated interferon α-2a | 0.114% | not present |
| REP 2139 | interferon α-2b | 0.0953% | not present |
| REP 2139 | thymosin α1 | 0.0922% | not present |
| REP 2139 | pegylated interferon α-2a | 0.104% | not present |
| REP 2139 | interferon λ1 | 0.0959% | not present |
| REP 2148 | interferon α-2b | 0.0615% | not present |
| REP 2148 | thymosin α1 | 0.061% | not present |
| REP 2148 | pegylated interferon α-2a | 0.0641% | not present |
| REP 2148 | interferon λ1 | 0.065% | not present |
| REP 2055 | thymosin α1 | not present | 0.0199% |
| REP 2055 | thymosin α1 | 0.0248% | 0.00959% |
| REP 2055 | pegylated interferon α-2a | not present | 0.0181% |
| REP 2055 | pegylated interferon α-2a | 0.0244% | 0.00938% |
| REP 2139 | thymosin α1 | not present | 0.0361% |
| REP 2139 | thymosin α1 | 0.0453% | 0.0175% |
| REP 2139 | pegylated interferon α-2a | not present | 0.0340% |
| REP 2139 | pegylated interferon α-2a | 0.0482% | 0.0184% |

The results from Examples III and IV demonstrate the following:
1. Compositions containing ON chelate complexes comprising calcium, magnesium or mixed calcium/magnesium and polypeptides or pegylated polypeptides can be prepared which are suitable for parenteral administration.
2. Neither the ON nor the polypeptide or pegylated polypeptide in these compositions in question undergoes any detectable chemical change, as evidenced by the almost perfect correlation between observed and theoretical molecular weights for REP 2055, REP 2057, REP 2139, REP 2148, interferon α-2b, thymosin α1 and interferon λ1.
3. In the case of compositions containing pegylated interferon α-2a, ONs are not altered, and polypeptide alterations (if any existed) could not be detected.

From these results, the following can also be inferred:
1. REP 2006 is a fully degenerate ON and as such is a prototypic model for the physiochemical properties common to all ONs. As such, any ON which can be formulated as a chelate complex would be compatible with these polypeptides or pegylated polypeptides in solution.
2. REP 2006, REP 2055, REP 2057 and REP 2148 are DNA while REP 2139 is RNA. Therefore, any RNA or DNA or RNA/DNA hydrid ON can be used in the preparation of compositions containing ON chelate complexes and polypeptides.
3. REP 2006, REP 2055 and REP 2057 have unmodified riboses while REP 2139 has each ribose 2' O methylated. Therefore, any 2' ribose modification will be compatible with the preparation of compositions containing ON chelate complexes and polypeptides.
4. REP 2139 and REP 2148 comprise each cytosine further modified as 5' methylcytosine. As such, ONs containing modified bases can be used in the preparation of compositions containing ON chelate complexes and polypeptides or pegylated polypeptides.
5. Compositions comprising an ON chelate complex and a polypeptide or a pegylated polypeptide will be compatible with any pharmaceutically acceptable divalent metal cation such as calcium and/or magnesium.
6. The four polypeptides used in the preparation of compositions span widely divergent structures: thymosin α1 is a small synthetic polypeptide, interferon α-2b and interferon λ1 are large recombinant polypeptides and pegylated interferon α-2a is a large recombinant peptide with a large, complex pegylated conjugate. Therefore, compositions comprising ON chelate complexes and polypeptides can be successfully prepared using a wide range of polypeptides from small synthetic polypeptides to large recombinant polypeptides with complex conjugates like polyethylene glycol. Likely the only limitation is that the polypeptide in question should be soluble in aqueous solutions. Additionally, the use of BSA as a carrier protein in the Intron A (used as a source of interferon α-2b) did not interfere with the stability of the compositions prepared with this polypeptide formulation.
7. As described above, pegylation is well known in the art to improve the tolerability and pharmacokinetic behavior of polypeptides and numerous pegylated polypeptides are currently in use as approved medications (see above). Therefore, the demonstration that the compositions described herein can tolerate well the presence of a pegylated peptide and the utility of combining an ON chelate complex and a pegylated peptide for improved antiviral response and in human patients (see example VI below) provides clear teaching to any skilled in the art that any polypeptide envisaged herein as part of the compositions described can also be present as a pegylated polypeptide. For example, thymosin α1 can be pegylated, interferon α-2b can be pegylated (a pegylated version of interferon α-2b, Peg-Intron™ is currently an approved medication), and interferon λ1 can be pegylated (a pegylated version of interferon λ1 is currently in clinical development as an antiviral agent).

EXAMPLE V

NAPs Inhibit the Transit of HBsAg Out of Cells

The hepatitis B surface antigen (HBsAg) has been shown to block many aspects of the immune response to HBV infection (Cheng et al., J. Hepatology 43: 465-471; Moucari et al., Hepatology 49: 1151-1157; Vanlandschoot et al., J. Gen. Virol. 83: 1281-1289; Woltman et al., PloS One 6: e15324; Wu et al., Hepatology 49: 1132-1140 and Xu et al., Mol. Immunology. 46: 2640-2646). Therefore, elimination of circulating HBsAg may be a critical factor in allowing restoration of immunocompetence in patients with chronic hepatitis B infection. An efficient method for eliminating HBsAg in the circulation is to prevent the formation and or release of SVPs from infected cells (SVPs are the major carrier of HBsAg in the blood). The morphogenesis and intracellular transit of SVPs can be modeled in vitro in BHK-21 cells by expressing the small form of the HBsAg protein (sHBsAg) which is the form specifically enriched in SVPs. This model system is considered to be a surrogate model for the morphogenesis and transit of HBV SVPs in human patients (Patient et al., J. Virology 81: 3842-3851). Owing to the critical role of serum HBsAg in allowing chronicity of HBV infection, the ability of compounds to block the formation of SVPs or their intracellular transit in this model demonstrates their antiviral activity against HBV.

Various NAP compounds were tested in sHBsAg-expressing BHK-21 cells including the fully degenerate phosphorothioated NAPs REP 2006 and REP 2107 (2107 also having all riboses with the 2'O methyl modification), a non-phosphorothioated, fully 2' O methylated degenerate NAP (REP 2086) as well as the NAPs consisting of a poly AC sequence: REP 2055 (SEQ ID NO: 2) and REP 2148 (SEQ ID NO: 11). These NAPs were introduced into BHK-21 cells via electroporation at the same time as the template RNA for sHBsAg expression using electroporation. Activity in the BHK model system was assessed by visualizing the location of HBsAg protein inside the BHK-21 cells by immunofluorescence microscopy. Compounds were judged to be active if HBsAg was restricted to the perinuclear space and prevented from transiting to the periphery of the cell (secretion). The activity of the various NAP compounds are summarized in Table 4 below.

TABLE 4

Effect of various NAPs on HBsAg transit in BHK-21 cells

| NAP | HBsAg retained in the perinuclear space | HBsAg transit to cellular periphery |
| --- | --- | --- |
| control (no NAP present) | – | ++++ |
| REP 2006 | ++++ | – |
| REP 2107 | +++ | + |
| REP 2086 | – | ++++ |
| REP 2055 (SEQ ID NO: 2) | ++++ | – |
| REP 2148 (SEQ ID NO: 11) | ++++ | – |

– = effect not observed
+ to ++++ = marginal to complete effect observed

The results with treatment of sHBsAg expressing BHK-21 cells with REP 2006 and REP 2107 demonstrate the ability to NAPs to block the transit of sHBsAg in a sequence independent fashion. The lack of activity with REP 2086 demonstrates that this activity is strictly dependent on the presence of phosphorothioation. Moreover, this ability was retained in the presence of 2' ribose modification (in REP 2107) and base modification (5' methylcytosine in the case of REP 2148). Additionally, REP 2107, REP 2055 and REP 2139 are known to be completely devoid of any immunostimulatory activity and were comparably active to REP 2006. Also the defined sequence of poly AC (REP 2055 and REP 2148) was comparable active to the degenerate sequence (REP 2006 and REP 2107)

These results show that within the context of a degenerate sequence and sequences containing repeats of AC (and therefore also CA) and other sequences also comprising repeats of alternate purine/pyrimidine nucleotides (such as TG and GT or UG and GU) and comprising 2' ribose modifications or base modifications or comprising both 2' ribose modifications and base modifications (see REP 2139 in example VI), phosphorothioated NAPs will be expected to be able to block the formation of and intracellular transit and secretion of SVPs from infected cells at oligonucleotide lengths from 20-120 nucleotides as described in U.S. Pat. Nos. 8,008,269, 8,008,270 and 8,067,385.

EXAMPLE VI

Combination Therapy for the Treatment of Chronic Hepatitis B in Human Patients REP 2055 is a simple sodium salt of a phosphorothioated ON (SED ID NO: 2). REP 2139-Ca is the calcium chelate complex of the phosphorothioate oligonucleotide REP 2139 (SEQ ID NO: 18) prepared in normal saline using a ratio of 30 mg of $CaCl_2$ for every 100 mg of oligonucleotide present. REP 2055 and REP 2139 are NAPs and this family of compounds are broad spectrum antiviral compounds effective against enveloped viruses (Bernstein et al., 2008, Antimicrobial Agents and Chemotherapy, 52: 2727-2733; Cardin et al., 2009, Virology Journal, 6: 214; Guzman et al., 2007, Antiviral Therapy, 12: 1147-1156; Lee et al., 2008, Virology, 372: 107-117; Matsumura et al., 2009, Gastroenterology, 137: 673-681; Vaillant et al., 2006, Antimicrobial Agents and Chemotherapy, 50: 1393-1401 and U.S. Pat. Nos. 8,008, 269B, 8,008,270 and 8,067,385). Chelate complexes do not affect the bioactivity of NAPs or other ON species and thus formulation of REP 2139 as a calcium chelate complex has no effect on its antiviral activity. The only required NAP modification for antiviral activity is phosphorothioation of each linkage in the ON. Additional modifications including 2' ribose modifications (such as 2' O methylation) and base modifications (such as 5' methylcytosine and 4' thiouracil) have negligible effect on the antiviral activity of NAPs but can be used to optimize tolerability in human patients.

Pegylated interferon α-2a is sold under the trademark Pegasys™ by Roche Inc. (Basel, Switzerland) and is approved for the treatment of chronic HBV infection. Thymosin α1 is sold under the trademark Zadaxin™ by Sci-Clone Pharmaceuticals (Foster City, Calif., U.S.A.) and is also approved for the treatment of chronic HBV infection in many Asian countries.

To examine if the antiviral effect of NAP treatment combined with immunotherapy (stimulation of the adaptive and innate immune responses) could improve antiviral response in patients with chronic HBV infection, patients underwent monotherapy with REP 2055 and combination therapy with REP 2139-Ca and either thymosin α1 (Zadaxin™—given as a 1.6 mg subcutaneous injection twice weekly) or pegylated interferon α-2a (Pegasys™—given as a 180 μg subcutaneous injection once weekly) to their ongoing NAP regimen.

Both REP 2055 and REP 2139-Ca, when used in monotherapy are equally active in blocking the release of HBsAg which is the therapeutic mechanism of action of all NAPs against HBV infection in general. REP 2055 and REP 2139-Ca, when given in comparable monotherapy regimens, achieved HBsAg clearance in the serum of HBV infected patients in 7/8 and 9/12 patients respectively and the clearance of serum HBsAg was comparable with both drugs (see Table 5), which shows the comparable antiviral activity of these NAPs when given as sodium salts or as chelate complexes.

TABLE 5

REP 2055 and REP 2139-Ca effectively and comparably clear serum HBsAg in patients with chronic HBV infection.

| NAP | Responder patient | Pretreatment serum HBsAg (mIU/ml*) | Serum HBsAg on treatment (mIU/ml*) |
|---|---|---|---|
| REP 2055 | 1 | 934 | 0.25 |
| | 2 | 1885.4 | 0.38 |
| | 3 | 384.1 | 0 |
| | 4 | 126645.07 | 0.03 |
| | 5 | 158180 | 0 |
| | 6 | 36996.00 | 7 |
| | 7 | 4762.5 | 50.6 |
| REP 2139-Ca | 1 | 70050 | 0.19 |
| | 2 | 13400 | 0 |
| | 3 | 3654.3 | 0.34 |
| | 4 | 47689.7 | 180.44 |
| | 5 | 107659.6 | 32.15 |
| | 6 | 58937.87 | 9.91 |
| | 7 | 17988.99 | 29.21 |
| | 8 | 125000 | 0.01 |
| | 9 | 1288.56 | 0.02 |

*as determined by the Abbott Architect™ quantitative test for HBsAg

Interferon based treatment typically leads to 25% of patients achieving control of their HBV infection after treatment is stopped (serum HBV DNA <500 copies/ml; Mourcari et al., 2009, Hepatology 49: 1151-1157) and thymosin α1 treatment is generally considered to have comparable effect (Yang et al., 2008 Antiviral Research 77: 136-141).

REP 2055 monotherapy lead to the achievement of control of HBV infection (serum HBV DNA <500 copies/ml) after treatment was stopped in 3/7 of patients (43%). REP 2139-Ca treatment, which has the identical effect to REP 2055 in clearing serum HBsAg, when given in monotherapy) combined with either thymosin α1 or pegylated interferon α-2a led to the establishment of virologic control in 8/9 patients (89%) with HBV infection (see Table 6).

TABLE 6

Achievement of sustained virological response (SVR) with NAP monotherapy or combined NAP/immunotherapy.

| NAP | Responder patient | Immunotherapy | SVR at 12 weeks post treatment* |
|---|---|---|---|
| REP 2055 | 1 | none | YES |
| | 2 | | NO |
| | 3 | | YES |
| | 4 | | NO |
| | 5 | | YES |
| | 6 | | NO |
| | 7 | | NO |
| REP 2139-Ca | 1 | Zadaxin ™ | YES |
| | 2 | Zadaxin ™ | YES |
| | 3 | Zadaxin ™ | YES |
| | 4 | Zadaxin ™/ Pegasys ™ | YES |
| | 5 | Zadaxin ™/ Pegasys ™ | YES |
| | 6 | Pegasys ™ | YES |
| | 7 | Pegasys ™ | NO |
| | 8 | Pegasys ™ | YES |
| | 9 | Pegasys ™ | YES |

*serum HBV DNA <500 copies/ml

These results demonstrate that the combined effect of an antiviral ON chelate complex (in this example REP 2139-Ca) and an antiviral polypeptide (in this example pegylated interferon α-2a or thymosin α1) can lead to an improvement in the off treatment control of HBV infection in human patients and further demonstrates the utility of combined treatment with a ON chelate complex and polypeptide or pegylated polypeptide in a patient with a viral infection.

Compositions comprised of an antiviral ON chelate complex and an antiviral polypeptide would be desirable as they would improve the overall antiviral response in patients with a viral infection (including HBV infection) by providing both agents simultaneously (the utility of which is disclosed in the current example).

The antiviral ON chelate in the above described composition can include any antiviral ON as described above and in the case of HBV could specifically include REP 2055 (SEQ ID NO: 3, REP 2139 (SEQ ID NO: 18), REP 2148 (SEQ ID NO: 11) or any other NAP compound which blocks the transit of HBsAg as described above.

The polypeptide in the above described composition can include any antiviral polypeptide or pegylated antiviral polypeptide and in the case of HBV could specifically include interferon α-2b, pegylated interferon α-2b, pegylated interferon α-2a, thymosin α1, interferon λ1 or pegylated interferon λ1.

A similar beneficial effect with the combination treatments described above could be realized not only in HBV infection but also in other viral infections such as hepatitis C, influenza, RSV and other viruses which could respond to the effect of an antiviral ON or an antiviral polypeptide or pegylated polypeptide. Although NAPs are used in the present example, such improvements in antiviral outcomes in human patients could be achieved with other antiviral ONs acting by sequence dependent mechanisms formulated as chelate complexes when combined with antiviral polypeptides or pegylated polypeptides. These effects would be also more broadly effective in other viral infections with the right combination of antiviral oligonucleotide chelate complex and antiviral polypeptide. For instance, NAPs are broadly active against many other enveloped viruses such as hepatitis C, influenza, respiratory syncytial virus and cytomegalovirus and therefore NAP chelate complexes, in combination with the appropriate antiviral polypeptide (which could be thymosin α1 or pegylated interferon α-2a but might also be another antiviral polypeptide better suited to a particular viral infection) would be expected to produce a much better antiviral response in the infected subject than with either compound in monotherapy. In another instance, the chelate complex of miravirsen (SEQ ID NO: 7) could be combined with an interferon (pegylated or not) to improve the antiviral response in patients with hepatitis C infection.

The beneficial effects demonstrated with NAP chelate complexes and thymosin α1 or pegylated interferon α-2a would also be expected to occur with ON chelate complexes of other classes of oligonucleotides such as antisense or sRNA or miRNA or aptamer ONs developed against a particular viral infection or immunostimulatory oligonucleotides. Therefore, the method of combining an ON chelate complex derived from any of these ON classes with an appropriate antiviral polypeptide would be expected to be of therapeutic use in a wide variety of viral infections which demonstrated responses to the antiviral oligonucleotide (either as a sodium salt or a chelate complex) or antiviral polypeptide or pegylated polypeptide in monotherapy.

In view of the above examples, it could now be envisaged that two or more antiviral ON chelate complexes (e.g. containing a NAP and an antisense ON or containing a NAP and an antiviral siRNA) could be combined with one or more antiviral polypeptides or pegylated polypeptides (e.g. pegylated interferon α-2a and thymosin α1 or thymosin α1 and pegylated interferon λ1), either in the same formulation or in multiple formulations to be administered via the same or different routes.

In the above example, REP 2139-Ca was administered by intravenous infusion and pegylated interferon α-2a or thymosin α1 were administered by subcutaneous administration. Based on the teachings of the above example, one skilled in the art would now be able to readily predict that the ON chelate complex and polypeptide could be given simultaneously in the same formulation (such as those that have been disclosed in examples 3 and 4 above) either by subcutaneous injection or intravenous infusion and would be predicted to have the same beneficial effect as when either agent was administered separately (either by the same or different routes of administration).

The beneficial effects of the combination treatment as described herein with an ON chelate complex and an antiviral polypeptide or pegylated polypeptide in the antiviral setting as described herein clearly predicts similar beneficial effects of combination treatment with ON chelates and polypeptides or pegylated polypeptides in therapeutic settings where both these agents have some measure of activity in monotherapy. For example, an antisense ON targeting a gene involved in cancer (which therefore has an anti-cancer activity), could be formulated as an ON chelate complex as described herein and further combined with an immunotherapeutic agent known to have some measure of anti-cancer activity when normally used in monotherapy. Such therapeutic settings could include cancer, multiple sclerosis, and Alzheimer's disease.

What is claimed is:

1. A pharmaceutical composition comprising an oligonucleotide (ON) chelate complex, consisting of two or more ONs linked intermolecularly by a divalent cation, and at least one of:

Thymosin α1;
Any α-interferon or pegylated derivatives thereof;
Any β-interferon or pegylated derivatives thereof;
Any γ-interferon or pegylated derivatives thereof;
Any λ-interferon or pegylated derivatives thereof;
Interferon α-2a or α-2b or α-N3;
Interferon β-1a or β-1b;
Interferon γ-1b;
Interferon λ1 or λ2 or λ3;

Pegylated interferon α-2a or α-2b or λ1 or λ2 or λ3;
Myrcludex B;
Any antiviral cytokine or pegylated derivatives thereof; and
Thymic protein A.

2. A pharmaceutical composition comprising an antiviral ON chelate complex, consisting of two or more antiviral ONs linked intermolecularly by a divalent cation, and at least one antiviral of:
Thymosin α1;
Any α-interferon or pegylated derivatives thereof;
Any β-interferon or pegylated derivatives thereof;
Any γ-interferon or pegylated derivatives thereof;
Any λ-interferon or pegylated derivatives thereof;
Interferon α-2a or α-2b or α-N3;
Interferon β-1a or β-1b;
Interferon γ-1b;
Interferon λ1 or λ2 or λ3;
Pegylated interferon α-2a or α-2b or λ1 or λ2 or λ3;
Myrcludex B;
Any antiviral cytokine or peqylated derivatives thereof; and
Thymic protein A.

3. The pharmaceutical composition of claim 1 or 2, wherein said divalent metal cation is calcium.

4. The pharmaceutical composition of claim 1 or 2, wherein said divalent metal cation is magnesium.

5. The pharmaceutical composition of claim 1 or 2, wherein said divalent metal cation is iron (2+), manganese, copper or zinc.

6. The pharmaceutical composition of claim 1 or 2, wherein said divalent cation is comprised of two or more different divalent metal cations.

7. The pharmaceutical composition of claim 1 or 2, wherein said divalent cation is comprised of calcium and magnesium.

8. The pharmaceutical composition of claim 1 or 2, wherein said ON chelate complex comprises at least one double stranded ON.

9. The pharmaceutical composition of claim 1 or 2, wherein said ON chelate complex comprises at least one ON with at least one phosphorothioate linkage.

10. The pharmaceutical composition of claim 1 or 2, wherein said ON chelate complex comprises at least one fully phosphorothioated ON.

11. The pharmaceutical composition of claim 1 or 2, wherein said ON chelate complex comprises at least one ON with one 2' modified ribose.

12. The pharmaceutical composition of claim 1 or 2, wherein said ON chelate complex comprises at least one ON which has each ribose 2' O-methylated.

13. The pharmaceutical composition of claim 1 or 2, wherein said ON chelate complex comprises at least one ON comprising at least one 5'methylcytosine.

14. The pharmaceutical composition of claim 1 or 2, wherein said ON chelate complex comprises at least one ON in which each cytosine is further 5'methylcytosine.

15. The pharmaceutical composition of claim 1 or 2, wherein said ON chelate complex comprises at least one ON in which every ribose is 2' O-methylated and in which each cytosine is further 5'methylcytosine.

16. The pharmaceutical composition of claim 1 or 2, wherein said ON chelate complex comprises an oligonucleotide selected from SEQ ID NOs: 1-6 and 10-18.

17. The pharmaceutical composition of claim 1 or 2, wherein said ON chelate complex comprises an oligonucleotide selected from SEQ ID NOs: 7-9.

18. The pharmaceutical composition of claim 1 or 2, formulated for subcutaneous administration.

19. The pharmaceutical composition of claim 1 or 2, formulated for intravenous infusion.

20. The pharmaceutical composition of claim 1 or 2, formulated for at least one of the following routes of administration: aerosol inhalation, intraocular, oral ingestion, enteric, intramuscular injection, intraperitoneal injection, intrathecal injection, intrathecal infusion, intratracheal, intravenous injection and topically.

21. The pharmaceutical composition of claim 1 or 2, wherein said ON chelate complex comprises at least one ON consisting of SEQ ID NO: 2.

22. The pharmaceutical composition of claim 1 or 2, wherein said ON chelate complex comprises at least one ON consisting of SEQ ID NO: 11.

23. The pharmaceutical composition of claim 1 or 2, wherein said wherein said ON chelate complex comprises at least one ON consisting of SEQ ID NO: 18.

24. The pharmaceutical composition of claim 1 or 2, further comprising one or more of the following: entecavir, tenofovir disoproxil fumarate, telbuvidine, adefovir dipivoxil, lamivudine, ribavirin, telaprevir, boceprevir, GS-7977, tegobuvir, zanamivir, oseltamivir, ganciclovir, foscarnet, acyclovir, zidovudine, abacavir, lopinavir, ritonavir or efavirenz.

25. The pharmaceutical composition of claim 1 or 2, further comprising a carrier.

26. A pharmaceutical composition comprising an ON chelate complex comprising an oligonucleotide consisting of SEQ ID NO: 3, and pegylated interferon α-2a.

27. A pharmaceutical composition comprising an ON chelate complex consisting of two or more ONs linked intermolecularly by a divalent cation, comprising at least one oligonucleotide consisting of SEQ ID NO: 18, and pegylated interferon α-2a.

28. A pharmaceutical composition comprising an ON chelate complex comprising an oligonucleotide consisting of SEQ ID NO: 11, and pegylated interferon α-2a.

29. A pharmaceutical composition comprising an ON chelate complex comprising an oligonucleotide consisting of SEQ ID NO: 3, and thymosin α1.

30. A pharmaceutical composition comprising an ON chelate complex comprising an oligonucleotide consisting of SEQ ID NO: 18, and thymosin α1.

31. A pharmaceutical composition comprising an ON chelate complex comprising an oligonucleotide consisting of SEQ ID NO: 11, and thymosin α1.

32. A pharmaceutical composition comprising an ON chelate complex comprising an oligonucleotide consisting of SEQ ID NO: 2, and interferon α-2b.

33. A pharmaceutical composition comprising an ON chelate complex consisting of two or more ONs linked intermolecularly by a divalent cation, comprising at least one oligonucleotide consisting of SEQ ID NO: 18, and interferon α-2b.

34. A pharmaceutical composition comprising an ON chelate complex comprising an oligonucleotide consisting of SEQ ID NO: 11, and interferon α-2b.

35. A pharmaceutical composition comprising an ON chelate complex comprising an oligonucleotide consisting of SEQ ID NO: 3, and pegylated thymosin α1.

36. A pharmaceutical composition comprising an ON chelate complex comprising an oligonucleotide consisting of SEQ ID NO: 18, and pegylated thymosin α1.

37. A pharmaceutical composition comprising an ON chelate complex comprising an oligonucleotide consisting of SEQ ID NO: 11, and pegylated thymosin α1.

38. A pharmaceutical composition comprising an ON chelate complex comprising an oligonucleotide consisting of SEQ ID NO: 3, and pegylated interferon α-2b.

39. A pharmaceutical composition comprising an ON chelate complex consisting of two or more ONs linked intermolecularly by a divalent cation, comprising an oligonucleotide consisting of SEQ ID NO: 18, and pegylated interferon α-2b.

40. A pharmaceutical composition comprising an ON chelate complex comprising an oligonucleotide consisting of SEQ ID NO: 11, and pegylated interferon α-2b.

41. A pharmaceutical composition comprising an ON chelate complex comprising an oligonucleotide consisting of SEQ ID NO: 3, and interferon λ1.

42. A pharmaceutical composition comprising an ON chelate complex comprising an oligonucleotide consisting of SEQ ID NO: 18, and interferon λ1.

43. A pharmaceutical composition comprising an ON chelate complex comprising an oligonucleotide consisting of SEQ ID NO: 11, and interferon λ1.

44. A pharmaceutical composition comprising an ON chelate complex comprising an oligonucleotide consisting of SEQ ID NO: 3, and pegylated interferon λ1.

45. A pharmaceutical composition comprising an ON chelate complex comprising an oligonucleotide consisting of SEQ ID NO: 18, and pegylated interferon λ1.

46. A pharmaceutical composition comprising an ON chelate complex comprising an oligonucleotide consisting of SEQ ID NO: 11, and pegylated interferon λ1.

\* \* \* \* \*

UNITED STATES PATENT AND TRADEMARK OFFICE
CERTIFICATE OF CORRECTION

PATENT NO.       : 9,492,506 B2                                Page 1 of 1
APPLICATION NO.  : 13/896510
DATED            : November 15, 2016
INVENTOR(S)      : Michel Bazinet et al.

It is certified that error appears in the above-identified patent and that said Letters Patent is hereby corrected as shown below:

In the Claims

In Claim 26, Column 44, Line 29 should read:
--of SEQ ID NO: 2, and pegylated interferon α-2a.--

In Claim 29, Column 44, Line 39 should read:
--of SEQ ID NO: 2, and thymosin α1.--

In Claim 35, Column 44, Line 58 should read:
--of SEQ ID NO: 2, and pegylated thymosin α1.--

In Claim 38, Column 44, Line 67 should read:
--of SEQ ID NO: 2, and pegylated interferon α-2b.--

In Claim 41, Column 45, Line 11 should read:
--of SEQ ID NO: 2, and interferon λ1.--

In Claim 44, Column 45, Line 20 should read:
--of SEQ ID NO: 2, and pegylated interferon λ1.--

Signed and Sealed this
Seventh Day of March, 2017

Michelle K. Lee
*Director of the United States Patent and Trademark Office*